US012758281B2

(12) United States Patent
Hollis et al.

(10) Patent No.: US 12,758,281 B2
(45) Date of Patent: Oct. 13, 2026

(54) MODULAR BONE IMPLANT DEVICES AND MEANS OF INSERTION

(71) Applicant: CROSSROADS EXTREMITY SYSTEMS, LLC, Memphis, TN (US)

(72) Inventors: Michael Chad Hollis, Collierville, TN (US); Daniel Sayger, Southaven, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 380 days.

(21) Appl. No.: 18/263,426

(22) PCT Filed: Jan. 27, 2022

(86) PCT No.: PCT/US2022/014112

§ 371 (c)(1),
(2) Date: Jul. 28, 2023

(87) PCT Pub. No.: WO2022/165047

PCT Pub. Date: Aug. 4, 2022

(65) Prior Publication Data

US 2025/0000557 A1 Jan. 2, 2025

Related U.S. Application Data

(60) Provisional application No. 63/244,943, filed on Sep. 16, 2021, provisional application No. 63/143,675, filed on Jan. 29, 2021.

(51) Int. Cl.
*A61B 17/80* (2006.01)
*A61B 17/00* (2006.01)
(Continued)

(52) U.S. Cl.
CPC ...... *A61B 17/8061* (2013.01); *A61B 17/0642* (2013.01); *A61B 17/1775* (2016.11);
(Continued)

(58) Field of Classification Search
CPC . A61B 17/0642; A61B 17/17; A61B 17/1775; A61B 17/686; A61B 17/8061;
(Continued)

(56) References Cited

U.S. PATENT DOCUMENTS

2018/0296257 A1* 10/2018 Penzimer ........... A61B 17/1775
2019/0358039 A1 11/2019 Ducharme et al.
(Continued)

FOREIGN PATENT DOCUMENTS

WO 2019/227103 A1 11/2019

*Primary Examiner* — Marcela I. Shirsat

(57) ABSTRACT

A modular bone fixation implant can include a bone plate, a post insert, a staple, and a bone screw. The bone plate includes a post aperture extending through a first end, a screw aperture extending through a second end, and a staple aperture at an intermediate location. Expandable arms disposed radially about the post axis include outward-facing bone engaging features which are forced outward to anchor the bone plate within a bone when the post insert is inserted through the post aperture. The post insert can comprise a polymer penetrable by screws such that the interior body of the post insert can serve as an anchor point for bone screws inserted laterally from a variety of angles, forming a modularly customizable implant for the midfoot or other bones.

6 Claims, 50 Drawing Sheets

(51) Int. Cl.

| | |
|---|---|
| ***A61B 17/064*** | (2006.01) |
| ***A61B 17/17*** | (2006.01) |
| ***A61B 17/68*** | (2006.01) |
| ***A61B 17/84*** | (2006.01) |
| ***A61B 17/86*** | (2006.01) |
| ***A61B 17/92*** | (2006.01) |

(52) U.S. Cl.

CPC ............ *A61B 17/809* (2013.01); *A61B 17/86* (2013.01); *A61B 17/92* (2013.01); *A61B 2017/00477* (2013.01); *A61B 17/064* (2013.01); *A61B 2017/0647* (2013.01); *A61B 17/686* (2013.01); *A61B 17/8004* (2013.01); *A61B 17/8052* (2013.01); *A61B 17/8057* (2013.01); *A61B 17/846* (2013.01); *A61B 17/866* (2013.01)

(58) Field of Classification Search

CPC ....... A61B 17/80; A61B 17/809; A61B 17/86; A61B 17/8625; A61B 17/863; A61B 17/8635; A61B 17/866; A61B 17/92; A61B 17/846; A61B 17/8695; A61B 17/8004; A61B 17/8052; A61B 17/8057; A61B 17/84; A61B 17/064; A61B 2017/564; A61B 2017/00477; A61B 2017/0647; A61B 2017/8655

USPC ... 606/71, 86 R, 87, 96, 280, 281, 282, 286, 606/297, 300, 75, 329, 86 B, 902, 915

See application file for complete search history.

(56) References Cited

U.S. PATENT DOCUMENTS

| | | | | |
|---|---|---|---|---|
| 2020/0305940 | A1 * | 10/2020 | Hollis .................. | A61B 17/808 |
| 2020/0383711 | A1 | 12/2020 | Hollis et al. | |

* cited by examiner

MODULAR BONE IMPLANT DEVICES AND MEANS OF INSERTION

CROSS-REFERENCE TO RELATED APPLICATIONS

This application is the National Stage Application of International Patent Application No. PCT/US2022/014112, filed Jan. 27, 2022, which claims the benefit of U.S. Provisional Application Ser. No. 63/143,675, filed Jan. 29, 2021, titled MODULAR BONE IMPLANT DEVICES AND MEANS OF INSERTION, and U.S. Provisional Application Ser. No. 63/244,943, filed Sep. 16, 2021, titled MODULAR BONE IMPLANT DEVICES AND MEANS OF INSERTION, both of which are incorporated by reference herein in their entirety and for all purposes.

FIELD

The present disclosure relates to medical devices and more particularly to bone fixation devices and systems.

BACKGROUND

Implantable devices such as staples, bone screws, bone plates, and the like, are typically used in surgical bone fixation procedures. Many existing implants such as staples may only allow for fixation between two points, or between a limited number and fixed arrangement of points. Other existing implants, such as bone plates or the like, may provide for fixation at a larger number of points in a fixed orientation due to the rigidity of constituent materials. Such implants may be undesirable for internal fixation in locations such as the midfoot, other portions of the foot, and/or other locations in which several relatively small bones are to be fixed or where variation in skeletal geometry between patients is common.

SUMMARY

Example embodiments described herein have innovative features, no single one of which is indispensable or solely responsible for their desirable attributes. Without limiting the scope of the claims, some of the advantageous features will now be summarized.

In a first aspect, a modular bone fixation system comprises a bone plate, a post insert, a staple, and a bone screw. The bone plate comprises a first end having a post aperture extending therethrough; a plurality of tabs adjacent to and circumferentially spaced about the post aperture, each of the plurality of tabs extending from a bottom surface of the bone plate and having one or more bone engaging features thereon, wherein the plurality of tabs are configured to extend into a first hole within a first bone; a second end having a screw aperture extending therethrough; and a staple aperture extending through the bone plate at an intermediate location between the first end the second end. The post insert comprises a body sized and shaped to fit within the post aperture and a head configured to seat against the bone plate around at least a portion of the post aperture, wherein when positioned within the post aperture, the body of the post insert forces the plurality of tabs outward such that the one or more bone engaging features grip the first bone. The staple comprises a bridge, a bone engaging member extending from a first end of the bridge, and a post engaging member extending from a second end of the bridge opposite the first end, the bone engaging member configured to extend through the staple aperture and seat within a second hole within a second bone to exert a compressive force between the first bone and the second bone. The bone screw is configured to extend through the screw aperture and seat within the second bone.

In some embodiments, the modular bone fixation system further comprises at least one lateral screw configured to seat at least partially within a third bone and the first bone, at least a portion of the at least one lateral screw being configured to seat within the post insert to fix the third bone relative to the post insert.

In some embodiments, the body of the post insert comprises a polymeric material penetrable by a screw.

In some embodiments, the post insert further comprises an axial aperture extending through the head and at least a portion of the body.

In some embodiments, the post engaging member is configured to seat within the axial aperture of the post insert.

In some embodiments, the head of the post insert comprises a cutaway sized and shaped to receive at least a portion of the bridge of the staple component therein.

In some embodiments, the first and second bones each comprise one of a cuneiform bone, a metatarsal, a cuboid bone, or a navicular bone.

In a second aspect, a modular implant kit comprises a bone plate, a post insert, a staple, a bone screw, and a plurality of lateral bone screws. The bone plate comprises a first end having a post aperture extending therethrough; a plurality of tabs adjacent to and circumferentially spaced about the post aperture, each of the plurality of tabs extending from a bottom surface of the bone plate and having one or more bone engaging features thereon; a second end having a screw aperture extending therethrough; and a staple aperture extending through the bone plate at an intermediate location between the first end the second end. The post insert comprises a polymeric body sized and shaped to fit within the post aperture and a head configured to seat against the bone plate around at least a portion of the post aperture, wherein insertion of the body of the post insert through the post aperture forces the plurality of tabs outward to grip a bone. The staple comprises a bridge, a bone engaging member extending from a first end of the bridge, and a post engaging member extending from a second end of the bridge opposite the first end. The bone screw has a shaft sized and shaped to fit within the screw aperture and a head larger than the screw aperture. The plurality of lateral bone screws have tips configured to penetrate the polymeric body of the post insert.

In some embodiments, the modular implant kit further comprises a drill guide for establishing entry paths for the lateral bone screws. The drill guide comprises an anchoring arm removably coupleable with the post insert; a cannula having a lumen therethrough defining a cannula axis of the drill guide; and a mechanical linkage movably coupling the cannula to the anchoring arm, wherein the mechanical linkage constrains motion of the cannula such that, when the anchoring arm is coupled with the post insert, the cannula is movable to a plurality of orientations in which the cannula axis intersects the polymeric body of the post insert.

In some embodiments, the cannula is coupled to the mechanical linkage by a cannula guide, the cannula being slidably disposed within the cannula guide.

In some embodiments, the cannula guide comprises a slit in a side thereof, the slit sized to accommodate a wire therethrough.

In some embodiments, the anchoring arm is slidably disposed within an anchoring assembly, the anchoring assembly configured to seat in a fixed orientation relative to the post insert.

In some embodiments, the anchoring assembly is configured to retain the anchoring arm at a plurality of predetermined vertical positions to define a plurality of non-intersecting drilling trajectories.

In some embodiments, the post insert may further comprise an axial aperture extending through the head and at least a portion of the body.

In some embodiments, the post engaging member of the staple may be sized and shaped to seat within the axial aperture of the post insert.

In some embodiments, the modular implant kit further comprises a second staple or a second bone screw, at least a portion of the second staple or the second bone screw comprising a polymer penetrable by the tips of the plurality of lateral bone screws.

In some embodiments, wherein the head of the post insert comprises a cutaway sized and shaped to receive at least a portion of the bridge of the staple component therein.

In some embodiments, the modular implant kit further comprises a post inserter, the post inserter comprising a shaft having a post engaging end configured to releasably secure the post insert; and a sleeve at least partially surrounding the shaft, the sleeve having a bone plate engaging end configured to seat against the post aperture of the bone plate.

In some embodiments, the post engaging end of the shaft comprises a tab configured to retain the post insert in a fixed rotational orientation relative to the shaft.

In some embodiments, the bone plate engaging end of the sleeve is configured to retain the sleeve in a fixed rotational orientation relative to the bone plate, and wherein the sleeve retains the shaft in a fixed rotational orientation relative to the sleeve.

In some embodiments, the post engaging end comprises one or more resilient arms having protrusions thereon, the protrusions configured to create a friction fit within an aperture of the post insert.

In some embodiments, the modular implant kit further comprises a post extraction tool, the post extraction tool comprising a shaft comprising a distal portion and an intermediate portion, the distal portion having first external screw threads thereon configured to engage with internal screw threads of a threaded aperture of the post insert, the intermediate portion having second external screw threads thereon; and a sleeve comprising a threaded aperture at a proximal end thereof, the threaded aperture having internal screw threads configured to engage with the second external screw threads on the intermediate portion of the shaft.

In some embodiments, the sleeve further comprises an distal cavity at a distal end thereof, the distal cavity sized to accommodate at least a portion of the post insert therein.

In a third aspect, a method for internal fixation of one or more bones using a modular bone implant comprises placing a bone plate at a first location proximate a first hole pre-drilled in a first bone, the bone plate comprising a post aperture at a first end thereof and a plurality of expandable tabs extending from a bottom surface of the bone plate at locations circumferentially spaced about the post aperture, such that the plurality of expandable tabs extend into the first hole; inserting a polymeric body of a post insert through the post aperture and into the first hole between the expandable tabs, wherein inserting the polymeric body of the post insert between the expandable tabs forces the expandable tabs outward such that outward-facing bone engaging features on the expandable tabs grip the first bone; and driving a lateral bone screw through a second bone and into the polymeric body to fix the second bone to the first bone.

In some embodiments, the bone plate further comprises a staple aperture at an intermediate location along the bone plate and the post insert comprises an axial aperture extending therethrough, the method further comprising inserting a first leg of a staple into a third bone through the staple aperture and inserting a second leg of the staple into the axial aperture of the post insert such that the staple fixes the third bone to the first bone.

In some embodiments, the bone plate further comprises a screw aperture at a second end opposite the first end, the method further comprising, after driving the lateral bone screw, driving a vertical bone screw through the screw aperture into the third bone.

In some embodiments, the method further comprises, prior to driving the lateral bone screw, inserting a guide wire along a screw path for the lateral bone screw using a drill guide coupled to the post insert, the drill guide defining a range of selectable screw paths intersecting the polymeric body of the post insert. The guide wire may define an entry point for the lateral bone screw into the post insert.

In some embodiments, the lateral bone screw is a cannulated screw comprising a cannula extending therethrough, the method further comprising removing the guide wire from the screw path after driving the lateral bone screw.

In some embodiments, the drill guide is adjustable along a central axis of the bone plate to define a plurality of non-intersecting screw paths, the method further comprising driving a second lateral bone screw through the second bone or a third bone and into the polymeric body to fix the second bone or the third bone to the first bone.

In some embodiments, the method further comprises driving a second lateral bone screw through a third or fourth bone and into the polymeric body to fix the third bone to the first bone.

In some embodiments, the first and second bones each comprise one of a cuneiform bone, a metatarsal, a cuboid bone, or a navicular bone.

In some embodiments, inserting the polymeric body of the post insert comprises coupling the post insert to a shaft of a post inserter, the post inserter further comprising a sleeve disposed about the shaft; moving the shaft in a first direction relative to the sleeve to withdraw the post insert to a position at least partially within the sleeve; seating the shaft against the bone plate proximate the post aperture; moving the shaft in a second direction opposite the first direction relative to the sleeve to push the polymeric body of the post insert through the post aperture and into the first hole; and moving the shaft in the first direction to decouple the shaft from the post insert.

In some embodiments, the method further comprises extracting the post insert from the first bone, wherein extracting the post insert comprises coupling a shaft of a post extraction tool to the post insert by engaging external screw threads of a distal end of the shaft with internal screw threads of an aperture of the post insert; rotating a sleeve of the post extraction tool about the shaft, the sleeve comprising a threaded aperture having internal screw threads engaged with external screw threads of an intermediate portion of the shaft, to move the sleeve along the shaft until the sleeve abuts the bone plate; and further rotating the sleeve to move the shaft linearly within the sleeve such that the post insert is draw at least partially out of the first hole.

In a fourth aspect, a modular bone fixation system comprises a cap, a post insert, and at least one lateral screw. The cap comprises a collar having a post aperture extending therethrough and a plurality of tabs adjacent to and circumferentially spaced about the post aperture, each of the plurality of tabs extending from a bottom surface of the bone plate and having one or more bone engaging features thereon, wherein the plurality of tabs are configured to extend into a first hole within a first bone. The post insert comprises a body sized and shaped to fit within the post aperture and a head configured to seat against the collar around at least a portion of the post aperture, wherein when positioned within the post aperture, the body of the post insert forces the plurality of tabs outward such that the one or more bone engaging features grip the first bone. The at least one lateral screw is configured to seat at least partially within a second bone and the first bone, at least a portion of the at least one lateral screw being configured to seat within the post insert to fix the second bone relative to the post insert.

In some embodiments, the body of the post insert comprises a polymeric material penetrable by a screw.

In some embodiments, the post insert further comprises an axial aperture extending through the head and at least a portion of the body.

In some embodiments, the first and second bones each comprise one of a cuneiform bone, a metatarsal, a cuboid bone, or a navicular bone.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

DETAILED DESCRIPTION

Figure 1A:
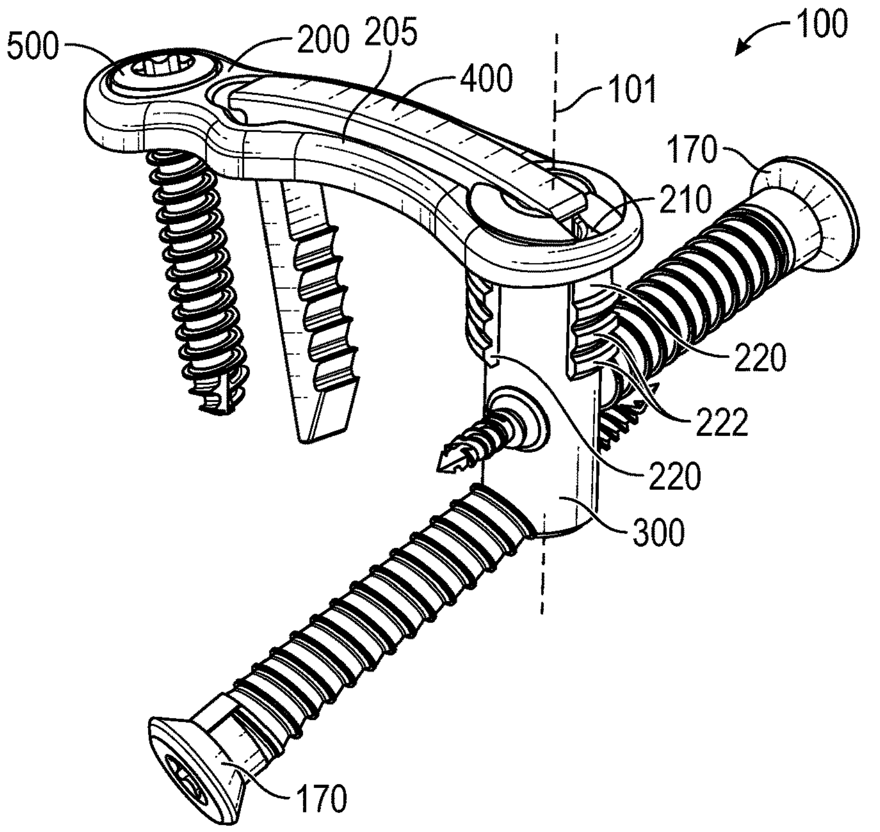
FIGS. 1A-1E depict a modular bone implant device including an example combination of modular components.

The following description is directed to certain implementations for the purpose of describing the innovative aspects of this disclosure. However, a person having ordinary skill in the art will readily recognize that the teachings herein can be applied in a multitude of different ways.

Generally described, the systems, devices, and methods described herein provide a modular bone implant device that can be customized to suit individual implant placement locations. The modular bone implant device may be provided in a kit and can include a plurality of optional and/or interchangeable implant components that may be selected, positioned, and secured at the time of placement. Accordingly, the modular bone implant device may allow a surgeon to perform a procedure such as internal fixation or osteosynthesis more effectively than would be possible with conventional bone implants that are not modular or otherwise customizable.

Among other features, some embodiments of the present technology provide modular implant systems including posts or post inserts configured to be seated within a bone and comprising a material penetrable by a laterally inserted screw. Advantageously, such penetrable materials allow lateral bone screws to be inserted at a variety of selectable trajectories which may be determined after initial placement of the post. In contrast, existing implant systems only allow for placement of lateral screws at pre-determined locations along pre-determined trajectories. Thus, the present technology can provide greater implant adaptability which may be especially desirable in regions of variable skeletal geometry such as the midfoot.

The embodiments described herein can be manufactured from a number of different materials or combinations of materials. Nitinol, for example, possess material properties, such as shape memory and/or super elasticity that may provide the inherent properties to allow an embodiment to have multiple configurations with or without an external mechanical manipulation. Stainless steel and/or titanium also have desirable material properties for the embodiments described herein. Stainless steel and/or titanium may not possess shape memory or super elasticity, but may possess the mechanical properties for embodiments that may benefit from mechanical manipulation to achieve multiple configurations. Still other materials such as PEEK (polyether ether ketone), UHMWPE (ultra-high-molecular-weight polyethylene), or other polymers may also possess material properties beneficial for the embodiments described herein. A combination of materials may also be preferred. For example, a combination of nitinol and titanium (e.g., a nitinol plate with titanium screws) may be the materials of choice for some embodiments. In another example, certain components or portions thereof may comprise a polymeric material in order to permit screws or other components to be secured therein. Those skilled in the art are aware of the typical materials and combinations of materials applicable to the current technology.

Figure 1B:
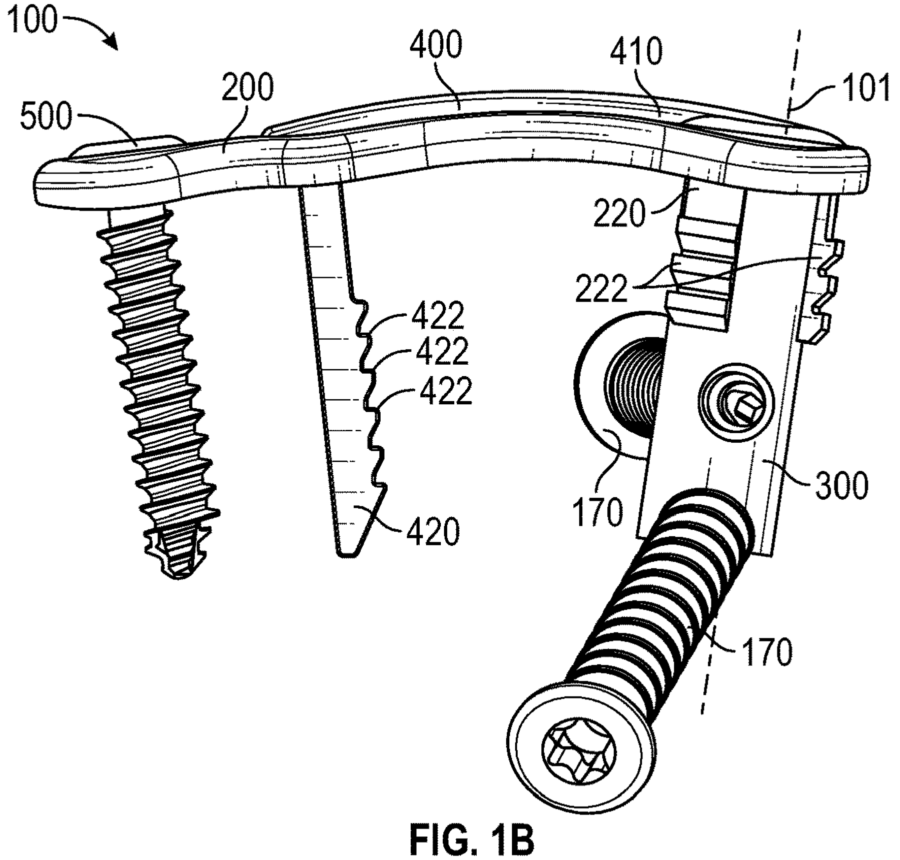
Figure 1C:
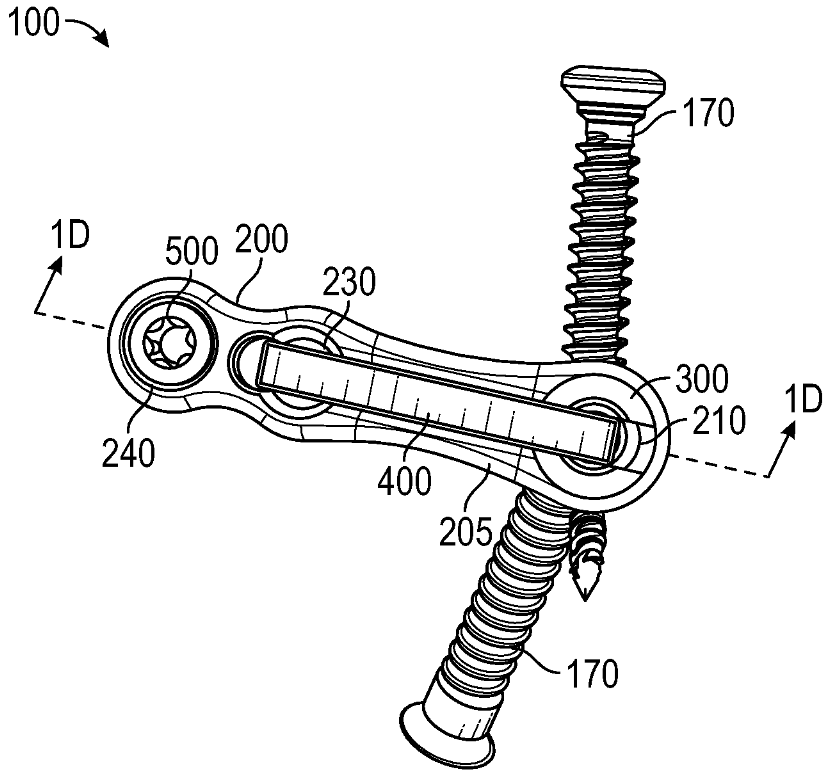
Figure 1D:
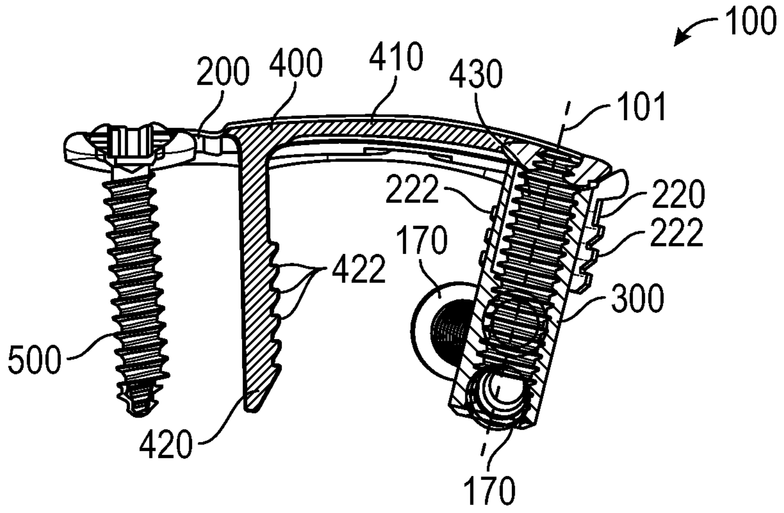
Figure 1E:
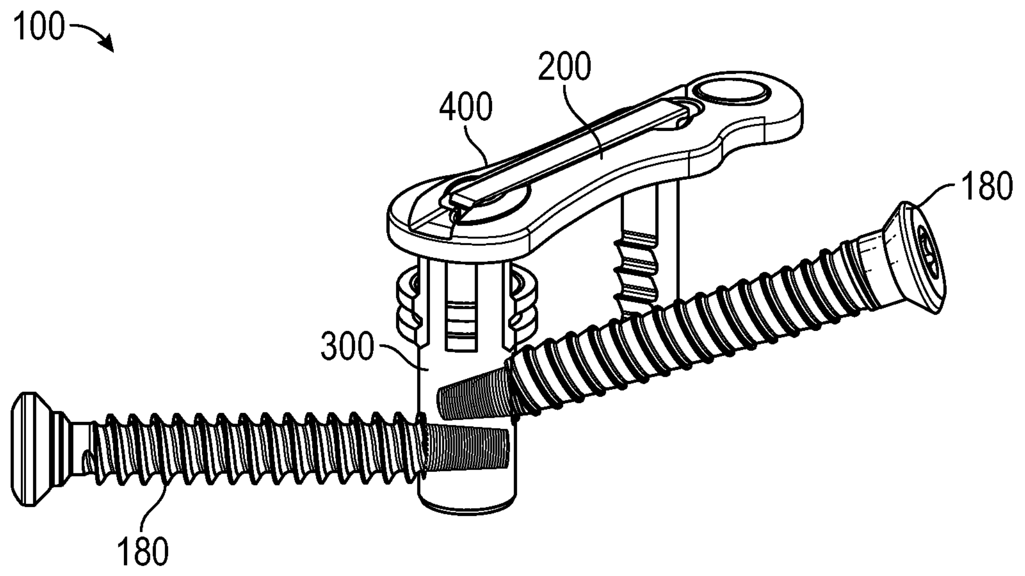

FIGS. 1A-1E illustrate example embodiments of an assembled implant 100 including various modular components described herein. FIG. 1A is a top perspective view of the implant 100 in a first configuration including a bone plate component 200, a post insert component 300, a staple component 400, a bone screw component 500, and a plurality of solid lateral screws 170. FIG. 1B is a side view of the implant 100 in the first configuration. FIG. 1C is a top view of the implant 100 in the first configuration. FIG. 1D is a cross-sectional view taken along line 1D-1D in FIG. 1C, illustrating internal components of the implant 100 in the first configuration. FIG. 1E depicts the implant 100 in alternative configuration including cannulated lateral screws 180.

The bone plate component 200 generally includes a body 205, a post aperture 210, expandable tabs 220, a staple aperture 230, and a screw aperture 240. In some embodiments, the bone plate component 200 comprises a metal or metal alloy such as stainless steel, titanium, nitinol, etc., a polymer such as PEEK, or other suitable material. In some embodiments, such as those in which the bone plate component 200 and the post insert component 300 both comprise a polymer, the bone plate component 200 and the post insert component 300 may be formed (e.g., molded or shaped) as a single contiguous component. The post insert component 300 may serve as a central post defining a central axis 101 of the implant 100, and is disposed within the post aperture 210, between the expandable tabs 220. As will be described in greater detail below, the presence of the post insert component 300 within the post aperture 210 causes the expandable tabs 220 to move outward from the central axis 101 such that the expandable tabs 220 further secure the plate to the bone and bone engaging features 222 of the expandable tabs 220 engage with surrounding bone to prevent withdrawal of the expandable tabs 220 from the bone. The bone plate component 200 is described in greater detail with reference to FIGS. 2A-2D.

The post insert component 300 can further serve as an anchor for additional fixation elements such as solid lateral screws 170 or cannulated lateral screws 180 (FIG. 1E). In some embodiments, the post insert component comprises a polymeric material, such as PEEK, UHMWPE, or other suitable polymer, so as to provide suitable structural rigidity while being penetrable by the tip of a screw. The solid lateral screws 170 and/or cannulated lateral screws 180 may include a tip segment having a diameter smaller than the main shaft of the screws to aid insertion of the screws into the post insert component 300. Additionally, the post insert component 300 may be at least partially hollow, as shown in FIG. 1D, to receive a post engaging member 430 of the stable component 400 therein. The post insert component 300 is described in greater detail with reference to FIGS. 3A-3C.

The staple component 400 includes a bridge 410 extending outward from the post insert component 300, a bone engaging member 420 extending from the bridge 410 at an end of the bridge 410 distal from the post insert component 300, and a post engaging member 430 extending from the bridge 410 at an end of the bridge 410 proximal to the post insert component 300. Bone engaging features 422 on an inward-facing side of the bone engaging member 420 are provided to prevent the bone engaging member 420 from withdrawing from a bone after the staple component 400 is placed. The post engaging member 430 of the staple component 400 seats within the post insert component 300 to secure the staple component 400 to the post insert component 300. Any compression applied by the post engaging member 430 is applied to the bone indirectly through the body of the post insert component 300. The compression loading is thus distributed along the length of the relatively broader post insert component 300, advantageously reducing the probability of failure in locations with poor bone quality. The staple component 400 may comprises a metal or metal alloy, such as stainless steel, titanium, nitinol, or any other suitable metallic or non-metallic material. In some embodiments, at least a portion of the bone engaging member 420 may comprise a polymeric material so as to serve as an anchor for one or more lateral screws. The staple component 400 is described in greater detail with reference to FIGS. 4A-4F.

The bone screw component 500 may be provided to further secure the implant 100 in place. In some embodiments, the bone screw component 500 may be anchored within the same bone or a different bone than the bone in which the bone engaging member 420 of the staple component 400 is seated. The bone screw component 500 may comprises a metal or metal alloy, such as stainless steel, titanium, nitinol, or any other suitable metallic or non-metallic material. In some embodiments, at least a portion of the bone screw component 500 may comprise a polymeric material so as to serve as an anchor for one or more lateral screws. The bone screw component 500 is described in greater detail with reference to FIGS. 5A-5F.

It will be understood that various other combinations and/or arrangements of the components described herein may equally be implemented without departing from the spirit or scope of the present disclosure. For example, the implant 100 may be packaged as an implant kit including one or more bone plate components 200, post insert components 300, staple components 400, bone screw components 500, solid lateral screws 170, and/or cannulated lateral screws 180, or variations thereof. Accordingly, any combination of one, two, three, four, five, six, or more lateral screws 170, 180 may be secured to a single post insert component 300 as appropriate for a particular implant location. Moreover, any number of lateral screws 170, 180 may be secured to other components, such as a polymeric or otherwise penetrable portion of a staple component 450 (FIGS. 4D-4F) or of a bone screw component 550 (FIGS. 5D-5F). Other modular combinations with or without lateral screws 170, 180 may be implemented as well. For example, two post insert components 300 may be connected by a staple component 400, with or without lateral screws 170, 180, to provide a more distributed loading, facilitating the use of a staple component 400 in weak or poor quality bone.

Advantageously, the modular components of the implant 100 may be selectable and orientable in a number of different possible configurations to take advantage of strong points in the skeletal structure to which the implant 100 will be fixed. For example, in some implementations one or more of a group of bones to be fixed may be stronger than other bones of the group of bones. A surgeon may select the strongest bone, or one of several relatively stronger bones, and may locate the post insert component 300 and expandable tabs 220 within the strongest or relatively stronger bone to serve as an anchor point for a fixation construct including the implant 100. The remaining components, such as lateral screws 170, 180, staple components 400, and/or bone screw components 500, when placed in conjunction with the anchor point, reliably fix other (potentially weaker) bones to the relatively strong bone selected as the anchor point.

Figure 2A:
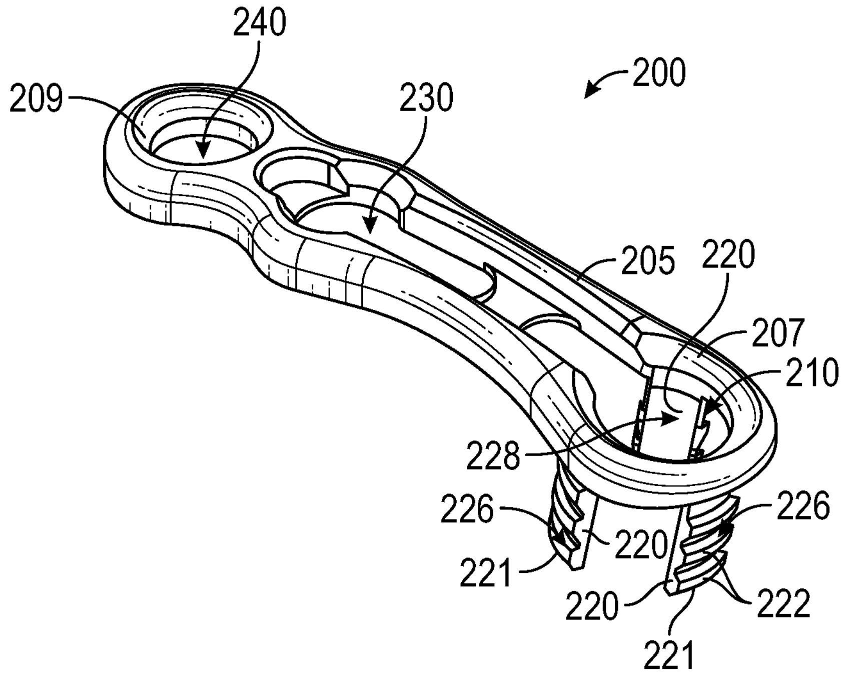
FIGS. 2A-2D depict an example bone plate component of a modular bone implant device.
Figure 2B:
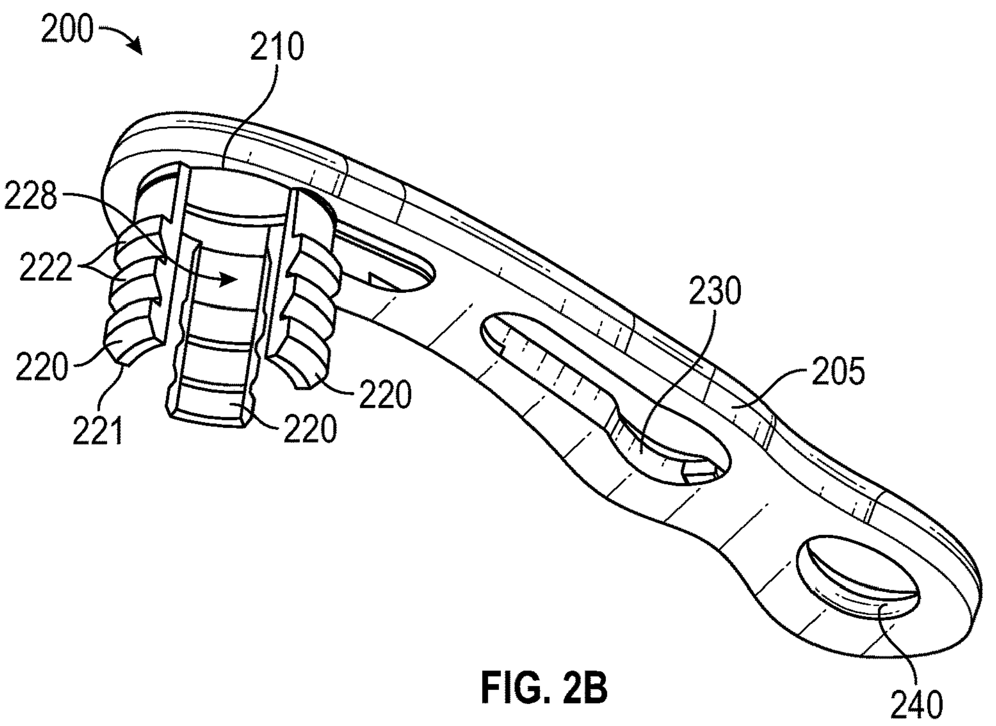
Figure 2C:
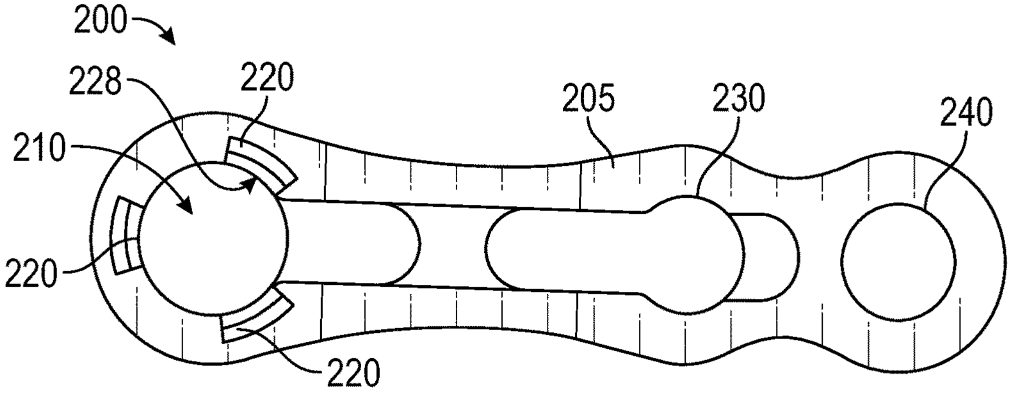
Figure 2D:
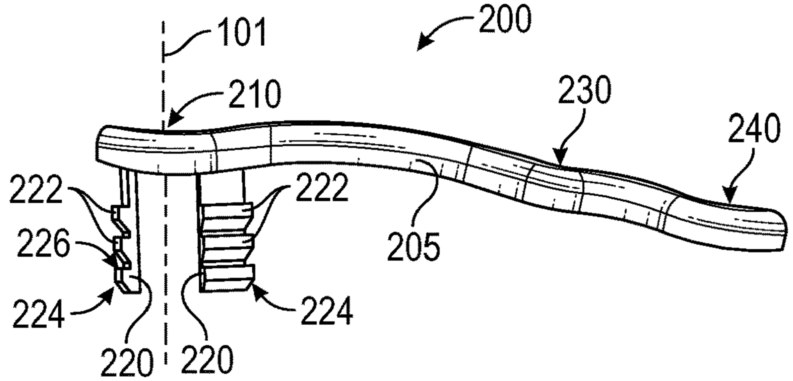

FIGS. 2A-2D depict a bone plate component 200 consistent with the implant 100 of FIGS. 1A-1E. FIGS. 2A and 2B are top and bottom perspective views, respectively, of the bone plate component 200. FIG. 2C is a bottom view of the bone plate component 200. FIG. 2D is a side view of the bone plate component 200.

The bone plate component 200 includes a body 205, a post aperture 210 disposed at a first end of the body 205, expandable tabs 220 disposed about the post aperture 210, a staple aperture 230 disposed in an intermediate portion of the body 205, and a screw aperture 240 disposed at a second end of the body 205 opposite the first end. In some embodiments, the bone plate component 200 may comprise a single formed component such that the expandable tabs 220 are integral to the body 205. The bone plate component 200 may comprise a metal or metal alloy such as stainless steel, titanium, nitinol or other shape memory alloy, or any other suitable material. The bone plate component 200 is configured to be fixed to bone in a desired orientation by the expandable tabs 220, by a staple leg inserted through the staple aperture 230, and/or by a bone screw inserted through the screw aperture 240.

The expandable tabs 220 include outward-facing bone engagement features 222 configured to anchor the bone plate component 200 within a hole such as a pre-drilled hole in a bone. The bone engagement features 222 may include sloped or angled distal surfaces 224 (e.g., in the direction of insertion into a pre-drilled hole) to facilitate insertion of the expandable tabs 220 into the bone. The bone engagement features 222 may further include flat or ridged proximal surfaces 226 (e.g., opposite the direction of insertion or in a pull-out direction) to prevent the expandable tabs 220 from pulling out of the bone after placement of the implant 100. The expandable tabs 220 may be manufactured with an inward bias such that the circular opening generally defined by the distal ends 221 of the expandable tabs 220 has a diameter smaller than the diameter of the post aperture 210 at the level of the body 205. Accordingly, when a post insert such as the post insert component 300 (FIGS. 1A-1E) having a circular profile with a diameter approximately equal to the diameter of the post aperture 210 is inserted along the central axis 101 through the post aperture 210 and between the expandable tabs 220, the exterior surface of the post insert component 300 pushes the distal ends 221 of the expandable tabs 220 outward such that the bone engaging features 222 engage the surrounding bone and the proximal surfaces 226 of the bone engaging features 222 prevent the expandable tabs 220 from backing out of the bone. In some embodiments, the post insert component 300 and post aperture 210 may have complementary non-circular profiles, such as an elliptical profile or a polygonal profile such as a square or triangular profile, to provide anti-rotational properties and/or to provide enhanced engagement with lateral screws. The expandable tabs 220 may be arranged in an array near the post aperture 210 such that the expandable tabs 220 may interact with the post insert component 300 upon insertion. The inner surfaces 228 of the expandable tabs 220 may be smooth to accommodate insertion of the post insert component 300. In other embodiments, the inner surfaces 228 of the expandable tabs 220 may have textured features (e.g., sawtooth or similar textures) that facilitate insertion of an insert with relatively little force but require relatively greater force to remove the insert, thus further promoting insert retention. A bevel 207 may surround the post aperture 210 to accommodate a complementary profile of the head of a post insert component. Similarly, a bevel 209 may surround the screw aperture 240 to accommodate a complementary profile of the head of a bone screw component.

Figure 3C:
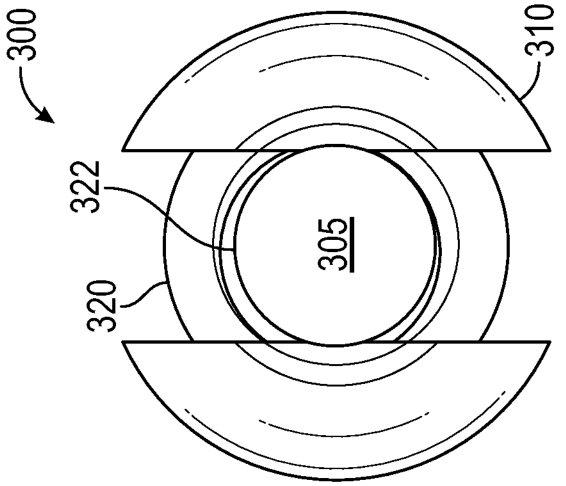
FIGS. 3A-3C depict an example post insert component of a modular bone implant device.
Figure 3B:
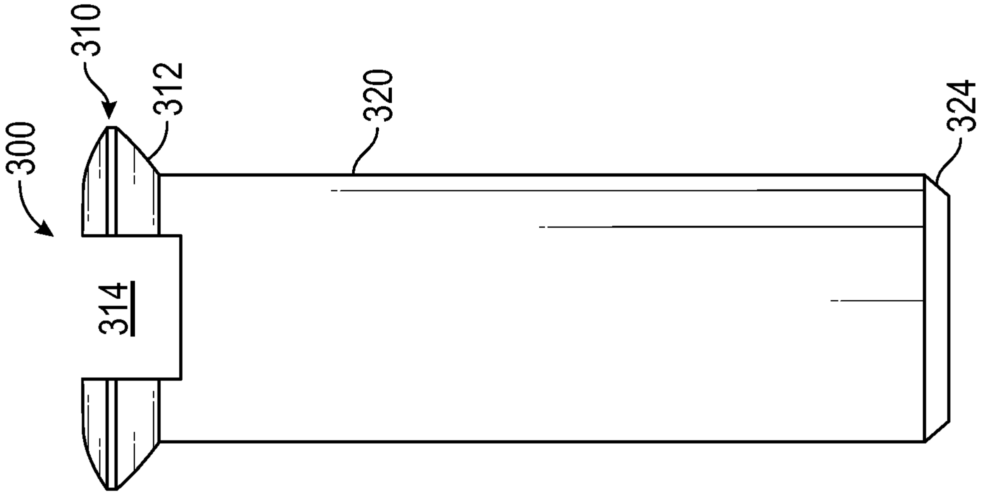
Figure 3A:
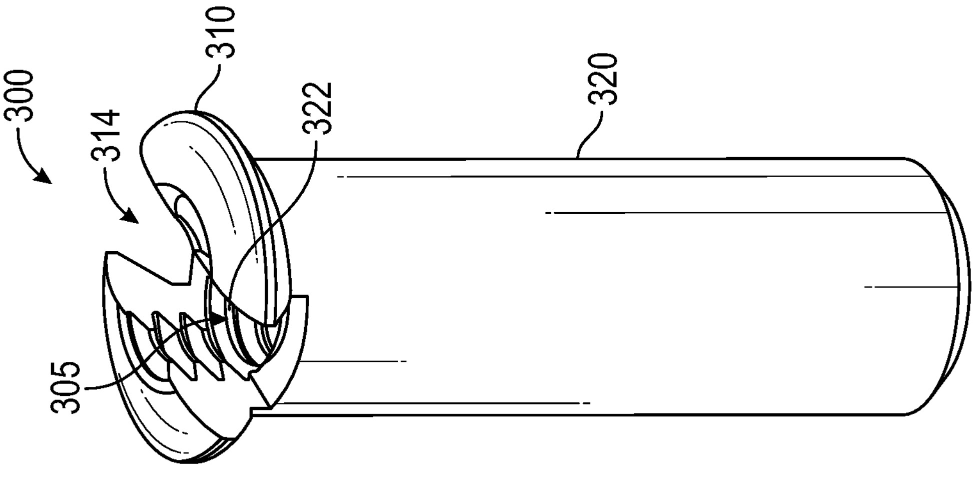

FIGS. 3A-3C depict a post insert component 300 consistent with the implant 100 of FIGS. 1A-1E. FIG. 3A is a top perspective view of the post insert component 300. FIG. 3B is a side view of the post insert component 300. FIG. 3C is a top view of the post insert component 300. The post insert component 300 may comprise a polymeric material, such as PEEK, UHMWPE, or other suitable polymer, so as to provide suitable structural rigidity while being penetrable by the tip of a wire or screw or other fixation element. In some embodiments, the center post 110 may comprise a single integrally formed component.

The post insert component 300 includes a head 310 and a body 320. A central aperture 305 extends through the head 310 and at least a portion of the body 320 to accommodate a structure such as a leg of a staple therein. The head 310 and the body 320 are sized and shaped to be compatible with a corresponding bone plate component 200 (FIGS. 1A-2E). For example, the head 310 may have an outer diameter larger than the diameter of the post aperture 210 of the bone plate component 200, and the body 320 may have an outer diameter approximately equal to or slightly smaller than the diameter of the post aperture 210 such that the head 310 defines a fully inserted position of the post insert component 300 relative to the bone plate component 200. A bevel 312 along the underside of the head 310 may have a complementary shape to the bevel 207 of the bone plate component 200 to facilitate a stable seating of the post insert component 300 along the central axis 101 of the post aperture 210.

The head 310 may further include a cutaway 314 sized and shaped to accommodate a portion of a staple such as staple component 400. For example, as shown in FIGS. 1A-1E, the post insert component 300 may be inserted into the post aperture 210 with a rotational orientation such that the cutaway 314 is oriented along the length of the bone plate component 200. Thus, when the staple component 400 is inserted with the post engaging member 430 seated within the aperture 305 of the post insert component 300, the portion of the bridge 410 adjacent to the post engaging member 430 can be mostly or entirely disposed within the cutaway 314. The cutaway 314 thus provides for a lower height profile of the implant 100 above the surface of the bone.

The body 320 has a generally cylindrical profile. In some embodiments, the body 320 may have other profiles, such as elliptical or polygonal profiles. The profile of the body 320 may be selected to correspond to a post aperture of a post aperture in which the post insert component 300 will be inserted. The interior surface of the aperture 305 extending through the body 320 may include screw threads 322 configured to releasably engage with threads of a post tool for insertion and/or removal of the post insert component 300. A bevel 324 at the distal end of the body 320 may facilitate insertion of the post insert component within a pre-drilled hole in the bone. As will be described in greater detail with reference to FIGS. 10-15, the body 320 may comprise a material penetrable by screws such that the body 320 serves as an anchor point for lateral screws (e.g., as shown in FIGS. 1A-1E).

Figure 3D:
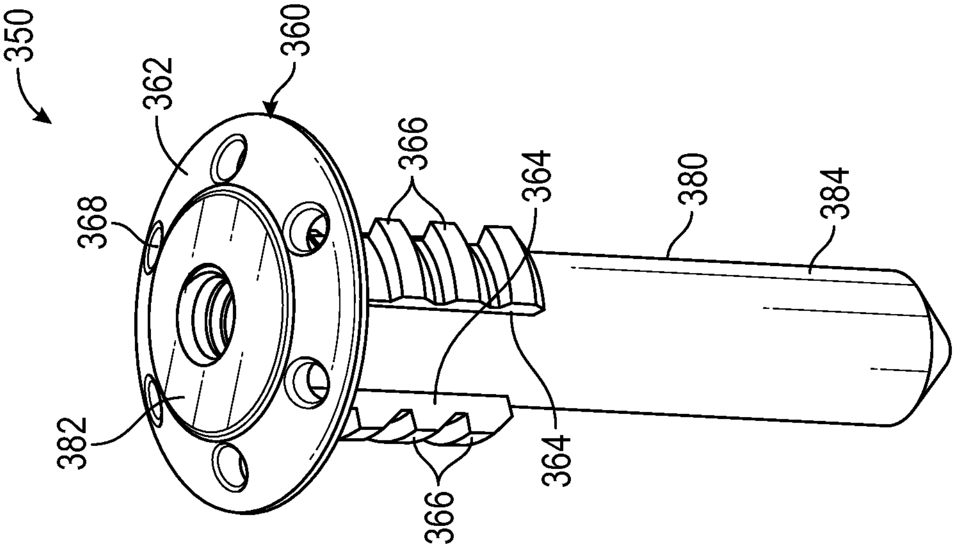
FIGS. 3D-3F depict example post insert and collar components of a modular bone implant device.
Figure 3E:
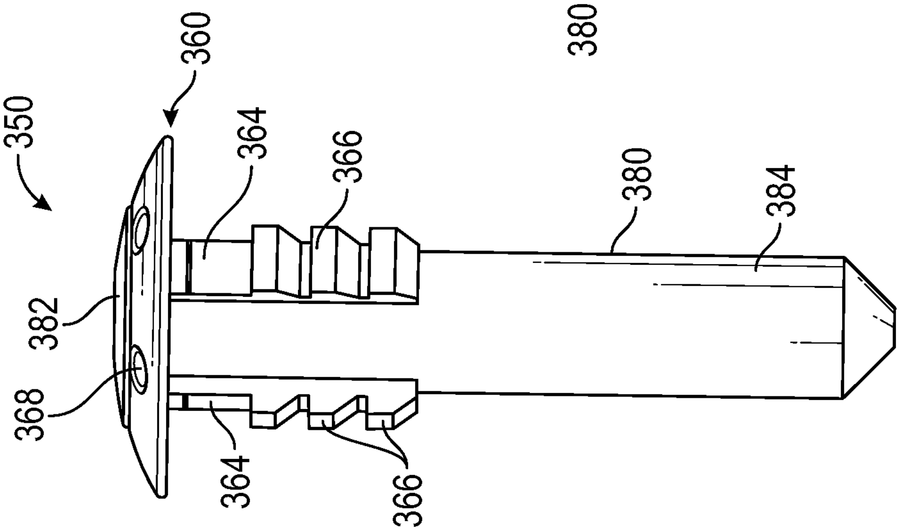
Figure 3F:
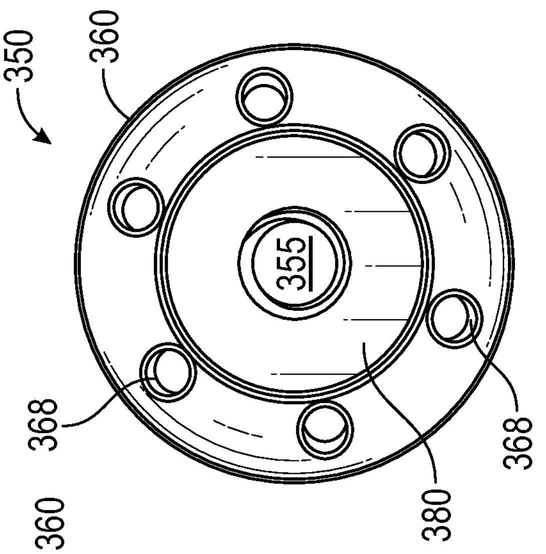

FIGS. 3D-3F depict an alternative embodiment not utilizing a bone plate. In this embodiment, suture anchor component 350 incorporates certain features of the bone plate component 200 and post insert component 300 described herein. FIG. 3D is a top perspective view of the suture anchor component 350. FIG. 3E is a side view of the suture anchor component 350, and FIG. 3F is a top view of the suture anchor component 350. The suture anchor component 350 includes cap 360 and a post insert 380. The cap 360 may comprise a metal or metal alloy such as stainless steel, titanium, nitinol or other shape memory alloy, or any other suitable material. The post insert 380 may comprise a polymeric material, such as PEEK, UHMWPE, or other suitable polymer, so as to provide suitable structural rigidity while being penetrable by the tip of a screw, and may accordingly be used in combination with one or more lateral screws as described elsewhere herein.

The cap 360 is configured to receive the post insert 380 therein, similar to the post aperture 210 of the bone plate component 200. The cap 360 generally comprises a collar 362 and expandable tabs 364 configured similarly to expandable tabs 220 of the bone plate component 200. The expandable tabs 364 may include bone engaging features 366 similar to bone engaging features 222 of the expandable tabs 220. The collar 362 may be fenestrated with suture apertures 368 such that one or more sutures may be anchored to the suture anchor component 350 by inserting the sutures through the suture apertures 368. Insertion of the post insert 380 between the expandable tabs 364 causes the tabs 364 to move outward to anchor the suture anchor component 350 within the bone. An aperture 355 extending through the head 382 and the body 384 of the post insert 380 accommodates an insertion tool and may further accommodate a leg of a staple component 400 inserted therein.

Figure 4A:
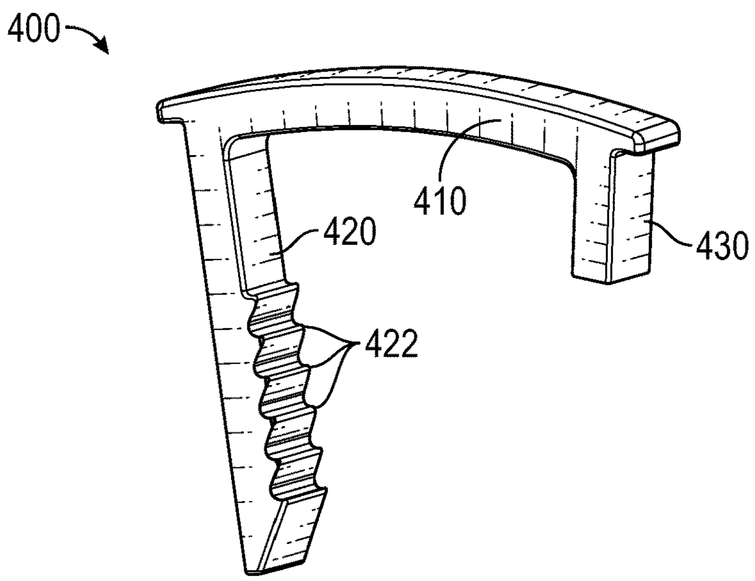
FIGS. 4A-4C depict an example staple component of a modular bone implant device.
Figure 4B:
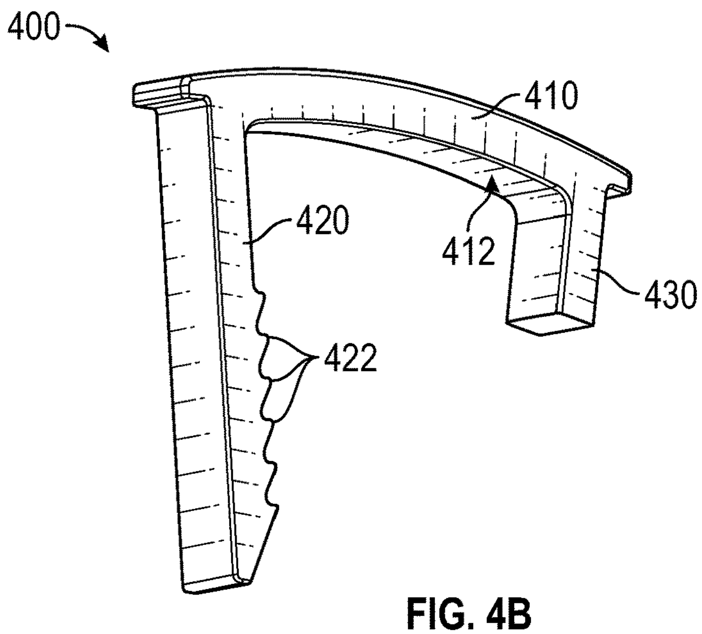
Figure 4C:
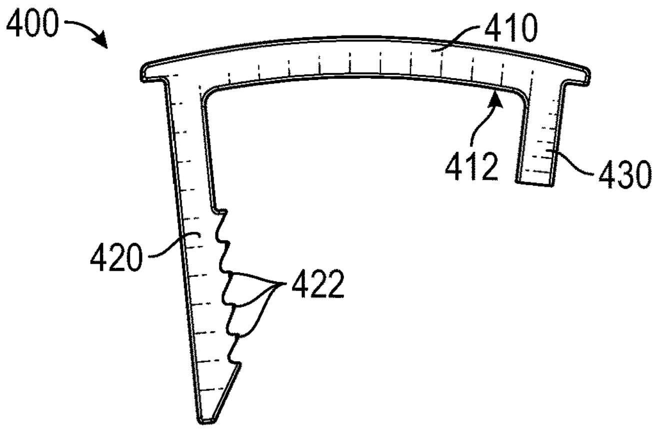

FIGS. 4A-4C depict a staple component 400 consistent with the implant 100 of FIGS. 1A-1E. FIGS. 4A and 4B are top and bottom perspective views, respectively. FIG. 4C is a side view of the staple component 400. The staple component 400 includes a bridge 410, a bone engaging member 420 (for example, a leg) disposed at a first end of the bridge 410, and a post engaging member 430 disposed at a second end of the bridge 410 opposite the bone engaging member 420. In some embodiments, the staple component 400 may comprise a single integrally formed component such that the bone engaging member 420 and the post engaging member 430 are integral to the bridge 410. In some embodiments, the staple component 400 is formed of a shape-memory alloy, such as nitinol.

The bone engaging member 420 includes bone engaging features 422 that improve bone purchase and/or pull-out strength of the staple component 400 from bone or soft tissue. In some embodiments, the post engaging member 430 may include similar features to the bone engaging features 422 to prevent pull-out. In the context of the implant 100 of FIGS. 1A-1E, the staple component 400 may be inserted after the post insert component 300 is inserted. A hole may be pre-drilled into the bone at the location of the staple aperture 230 of the bone plate component 200, either before or after placement of the bone plate component 200, such that the staple component 400 can be placed by inserting the bone engaging member 420 into the bone through the staple aperture 230 and inserting the post engaging member 430 into the central aperture 305 of the post insert component 300. The staple component 400 may be inserted until the bone-facing side 412 of the bridge abuts the body 205 of the bone plate component 200 and/or until the bridge 410 is at least partially disposed within the cutaway 314 of the head 310 of the post insert component 300. The staple component 400 may then be released.

In some embodiments, the bridge 410 has a curve or arc such that the bone engaging member 420 is biased inward, further improving bone purchase and/or pull-out strength of the staple component 400. In some embodiments, the bridge 410 may be resilient such that the bridge 410 can be bent into a linear configuration for insertion, and released to bias toward the curved configuration when the bone engaging member 420 has been seated within the bone and the post engaging member 430 has been seated within the central aperture 305 of a post insert component 300. In some embodiments, the bone engaging member 420 is substantially perpendicular to the adjacent portion of the bridge 410. When the bridge 410 is in its relaxed curve shape prior to insertion, the bone engaging member 420 forms an angle relative to the center of the bridge 410. In some embodiments, when the bridge 410 is deformed into a substantially linear configuration and the bone engaging member 420 has been seated within the bone and the deformed bridge 410 has been released, the bridge 410 remains deformed due to the presence of bone between the bone engaging member 420 and the post insert component 300, such that a compressive force between the bone engaging member 420 and the post insert component 300 is created. Example staple inserters suitable for inserting staples such as the staple component 400 are described in U.S. patent application Ser. No. 16/820,332, which is incorporated by reference herein.

Figure 4D:
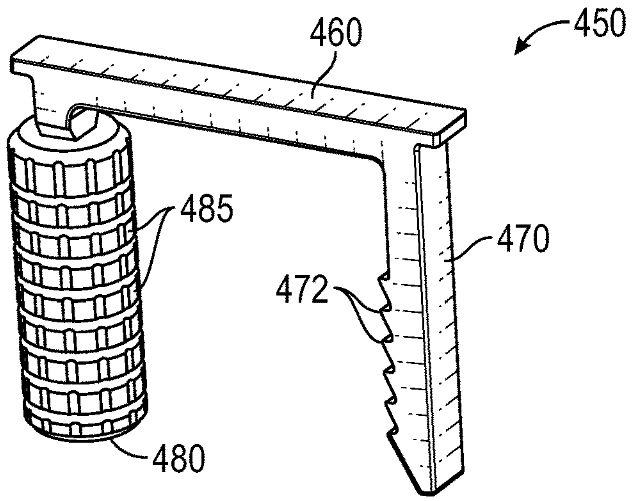
FIGS. 4D-4F depict an alternative example staple component of a modular bone implant device.
Figure 4E:
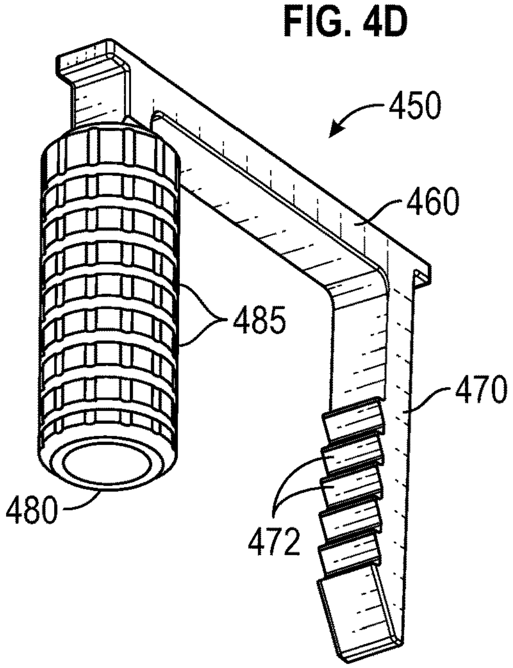
Figure 4F:
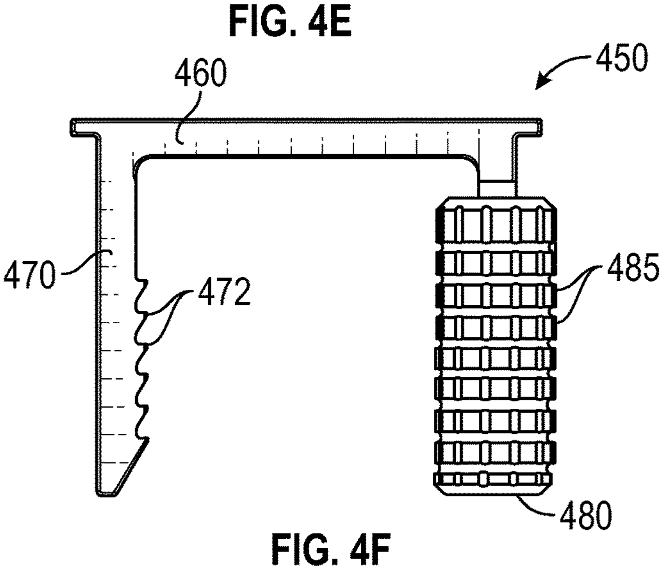

FIGS. 4D-4F depict an alternative embodiment of a staple component 450 not utilizing a bone plate. The staple component 450 generally incorporates the functionality of both the staple component 400 and the post insert component 300 of the implant 100 in a single component. Similar to the staple component 400, the staple component 450 includes a bridge 460 and a bone engaging member 470, including bone engaging features 472, extending from a first end of the bridge 460. The bridge 460 and the bone engaging member 470 may be formed of a shape-memory alloy, such as nitinol. Although the bridge 460 of the staple component 450 is illustrated in a straight configuration, in some embodiments the bridge 460 may be curved and/or deformable for insertion as described above with reference to FIGS. 4A-4C.

A post insert member 480 extends from the bridge 460 at a second end of the bridge 460 opposite the first end. In some embodiments, both legs of the staple component 450 may be post insert members 480. The post insert member 480 may comprise a polymeric material, such as PEEK, UHMWPE, or other suitable polymer, so as to provide suitable structural rigidity while being penetrable by the tip of a screw. In some embodiments, the post insert member 480 may be molded or otherwise assembled to the staple component 450. The post insert member 480 may further include one or more textured features 485 on an exterior surface which may facilitate the insertion of screws, wires or other fixation members into the post insert member 480, such as by preventing the tip of a screw from sliding along the surface of the post insert member 480. The textured features 485 are not limited to the post insert member 480 of the staple component 450, and may similarly be applied to any post insert described herein. For example, the post insert component 300 of FIGS. 3A-3C and/or the post insert 380 of FIGS. 3D-3F may include textures similar to textured features 485.

In the context of an implant such as the implant 100 of FIGS. 1A-1E, holes may be pre-drilled for both the post insert member 480 and the bone engaging member 470. The expandable tabs 220 of the bone plate component 200 may be inserted within the hole pre-drilled for the post insert member 480. The bone plate component 200 may then be secured to the bone by simultaneously inserting the post insert member 480 and the bone engaging member 470 of the staple component 450 into the pre-drilled holes such that the post insert member 480 pushes the expandable tabs 220 outward as described elsewhere herein.

Figure 5A:
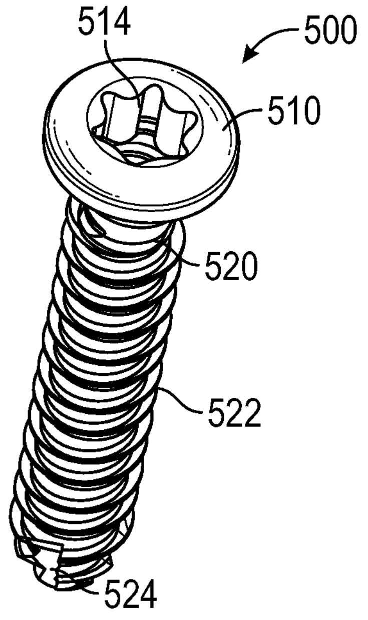
FIGS. 5A-5C depict an example bone screw component of a modular bone implant device.
Figure 5B:
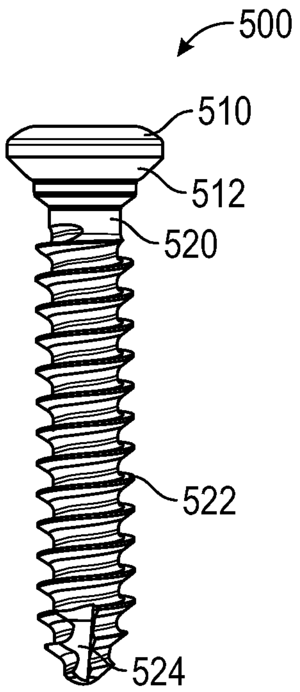
Figure 5C:
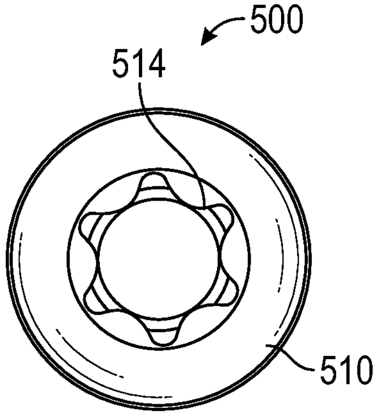
Figure 5D:
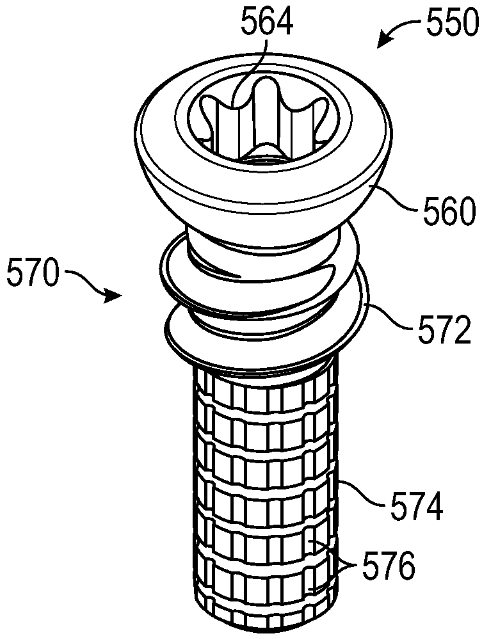
FIGS. 5D-5F depict an alternative example bone screw component of a modular bone implant device.
Figure 5E:
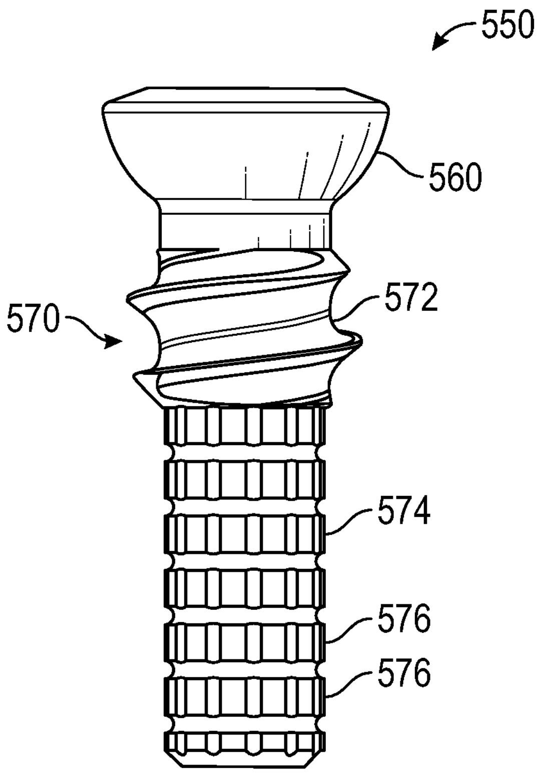
Figure 5F:
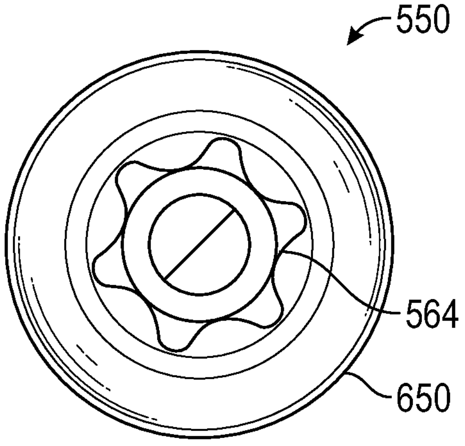

FIGS. 5A-5C depict a bone screw component 500 consistent with the bone screw component 500 of FIGS. 1A-1D. FIG. 5A is a top perspective view of the bone screw component 500. FIGS. 5B and 5C are side and top views of the bone screw component 500. The bone screw component 500 may comprise any suitable metal, alloy, or non-metallic material, such as titanium, stainless steel, or the like.

The bone screw component 500 includes a head 510 and a shaft 520. The shaft 520 includes bone engagement features 522. The bone engagement features 522 may be screw threads and in some embodiments may include flutes 524 extending along a portion of the shaft 520. The flutes 524 may permit the bone screw component 500 to be a self-tapping bone screw to facilitate placement within the bone. A bevel 512 along the underside of the head 510 may have a complementary shape to the bevel 209 of the bone plate component 200 to facilitate a stable seating of the bone screw component 500 within the screw aperture 240. The head 510 further includes a recess 514 shaped to receive a driver. Although the bone screw component 500 of FIGS. 5A-5C includes a hexalobular or six-pointed star-shaped recess (e.g., compatible with an ISO 10664 or Torx driver), the recess 514 may equally be implemented as a slotted, Phillips, hex, or any other screw drive shape. It will be appreciated that any suitable bone fastener other than bone screw component 500 may be used.

FIGS. 5D-5F depict an alternative embodiment of a bone screw component 550 not utilizing a bone plate. FIG. 5D is a top perspective view of the bone screw component 550. FIGS. 5E and 5F are side and top views of the bone screw component 550.

The bone screw component 550 includes a head 560 similar to the head 510 of the bone screw component 500, having a recess 564 shaped to receive a driver. The bone screw component includes a shaft 570 having an upper portion 572 and a lower portion 574. The upper portion 572 is similar to the shaft 520 of the bone screw component 500, including bone engagement features such as screw threads. The head 560 and the upper portion 572 of the shaft 570 may be integrally formed or otherwise assembled (e.g., press fit, slip fit with adhesive, etc.) and may comprise any suitable metal, alloy, or non-metallic material, such as titanium, stainless steel, or the like.

The lower portion 574 of the shaft 570 may comprise a polymer such as any of the polymeric materials suitable for the post insert component 300, post insert 380, or post insert member 480 described elsewhere herein. For example, the lower portion 574 may comprise PEEK, UHMWPE, or other suitable polymer, so as to provide suitable structural rigidity while being penetrable by the tip of a screw. The lower portion 574 may further include one or more textured features 576 on an exterior surface which may facilitate the insertion of screws into the lower portion 574 of the shaft 570, such as by preventing the tip of a screw from sliding along the surface of the lower portion 574.

Figure 6A:
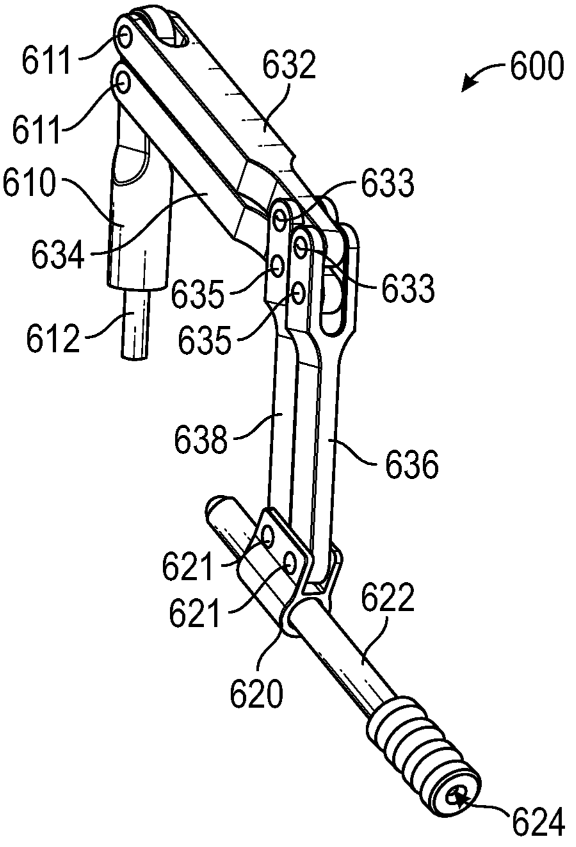
FIGS. 6A-6D depict an example drill guide configured to be used with any of the bone implant devices and components of FIGS. 1A-5F.
Figure 6B:
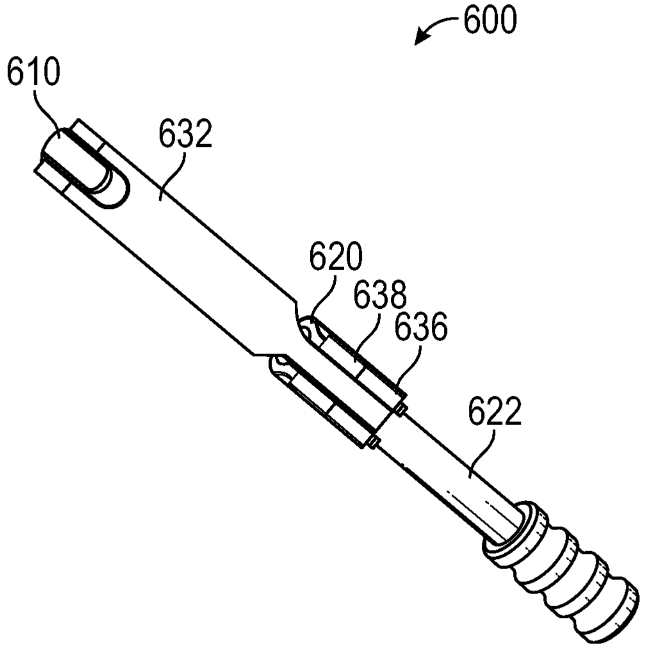
Figure 6C:
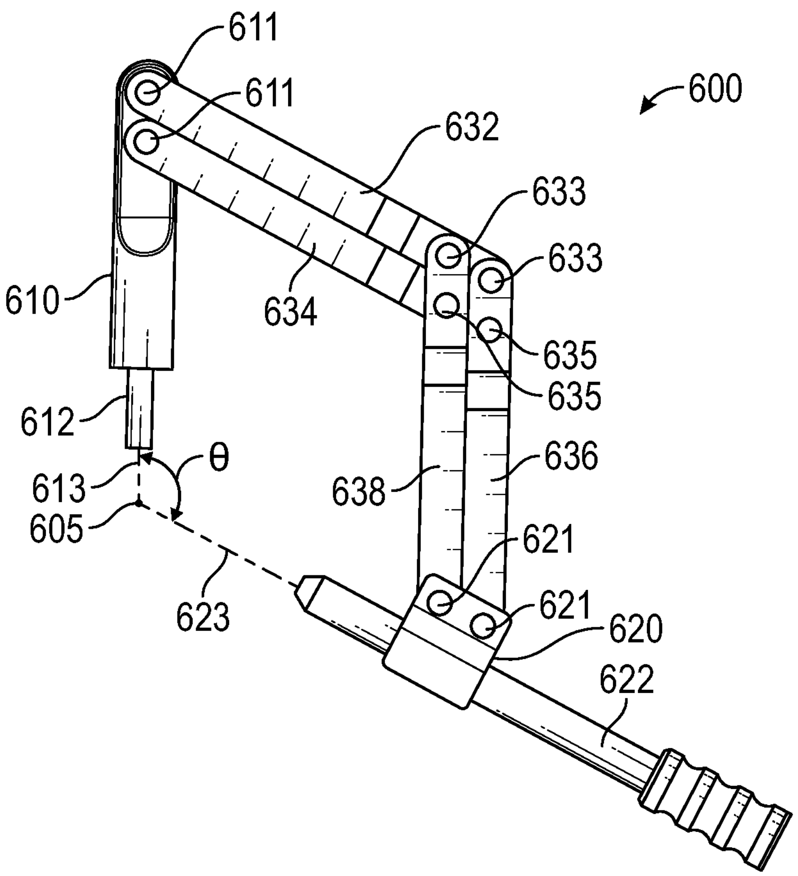
Figure 6D:
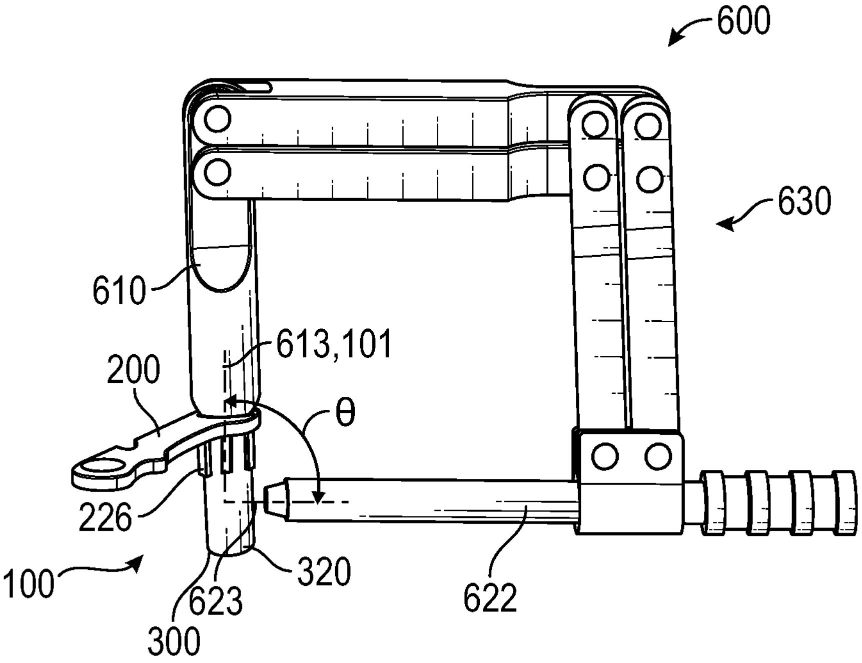

FIGS. 6A-6D depict an example drill guide 600 configured to be used with any of the bone implant devices and components of FIGS. 1A-5F. FIG. 6A is a perspective view of the drill guide 600 in a first angular configuration. FIGS. 6B and 6C are top and side views, respectively, of the drill guide 600 in the first angular configuration. FIG. 6D is a side view of the drill guide 600 coupled to an implant 100 in a second angular configuration illustrating the motion of components of the drill guide 600.

The drill guide 600 includes an anchoring arm 610, a cannula guide 620 for orienting a drill cannula 622, and a linkage 630 including parallel pairs of first linkage arms 632, 634 and second linkage arms 636, 638. Some or all of the components of the drill guide 600 may comprise a suitably rigid material such as a metal or metal alloy (e.g., stainless steel, titanium, or the like) a polymeric material, or other suitable material.

The anchoring arm 610 includes a tip 612 adapted to removably couple to or seat against or within the top of a penetrable post (e.g., the post insert component 300, post insert 380, or post insert member 480) or of a component containing a penetrable portion (e.g., the staple component 450 or the bone screw component 550 described elsewhere herein). The tip 612 as shown in FIGS. 6A-6D has a cylindrical profile suitable for seating within the central aperture 305 of the post insert component 300. The cylindrical profile of the tip 612 may have a diameter approximately equal to or slightly smaller than an inner diameter of the central aperture 305 such that the tip 612 can be stably seated within the central aperture 305 while being rotatable about the central axis 101 (FIGS. 1A, 1B). In other embodiments, the tip 612 may have a different profile which may be suitable sized and shaped to mate with the desired component. The anchoring arm 610 and tip 612 are oriented along an anchoring arm axis 613 (FIG. 6C) which passes through the center of the cylindrical profile. The anchoring arm axis 613 may be coincident with the central axis 101 when the tip 612 is seated within the aperture 305 of a post insert component 300 of the implant 100, as shown in FIG. 6D.

The cannula 622 is slidably disposed within the cannula guide 620. A lumen 624 extends through the length of the cannula 622 along a cannula axis 623. The inner diameter of the lumen 624 can be selected to accommodate a suitable drill, wire, and/or pin (e.g., a K-wire or the like) such that the cannula axis 623 defines an entry path for a drill, wire, or pin inserted through the lumen 624.

The linkage 630 is configured to constrain the motion of the cannula guide 620 such that the cannula axis 623 intersects a post insert component to which the anchoring arm 610 is coupled. The first linkage arms 632, 634 are each rotatably coupled to the anchoring arm 610 at pivot joints 611. The second linkage arms 636, 638 are each rotatably coupled to the first linkage arms 632, 634 at pivot joints 633, 635, respectively. The cannula guide 620 is rotatably coupled to each of the second linkage arms 636, 638 at pivot joints 621.

This configuration of first linkage arms 632, 634 and second linkage arms 636, 638 constrains the motion of the components of the drill guide 600 such that the anchoring arm axis 613, the cannula axis 623, and the two pairs of linkage arms 632, 634 and 636, 638 form a parallelogram. A surgeon may select a desired zenith angle θ between the anchoring arm axis 613 and the cannula axis 623; as the angle θ changes, the linkage 630 causes the other angles of the parallelogram to change in unison such that the parallelogram shape is maintained and the location of the intersection 605 of the anchoring arm axis 613 and the cannula axis 623 remains at a constant position relative to the tip 612 of the anchoring arm 610. In practice, this configuration allows a surgeon to seat the tip 612 within the aperture of a post insert component after the post insert component is placed within a bone, and select a desired lateral screw entry location by moving the cannula 622; the linkage 630 automatically adjusts the zenith angle θ of the cannula axis 623 such that any screw path selected using the drill guide 600 will intersect the post insert component.

Figure 6E:
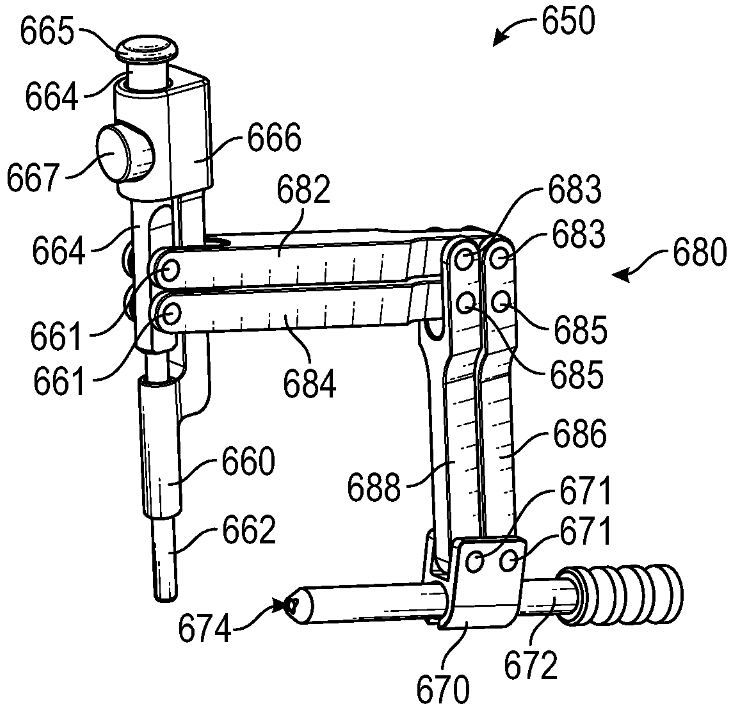
FIGS. 6E-6H depict an alternative example drill guide configured to be used with any of the bone implant devices and components described herein.
Figure 6F:
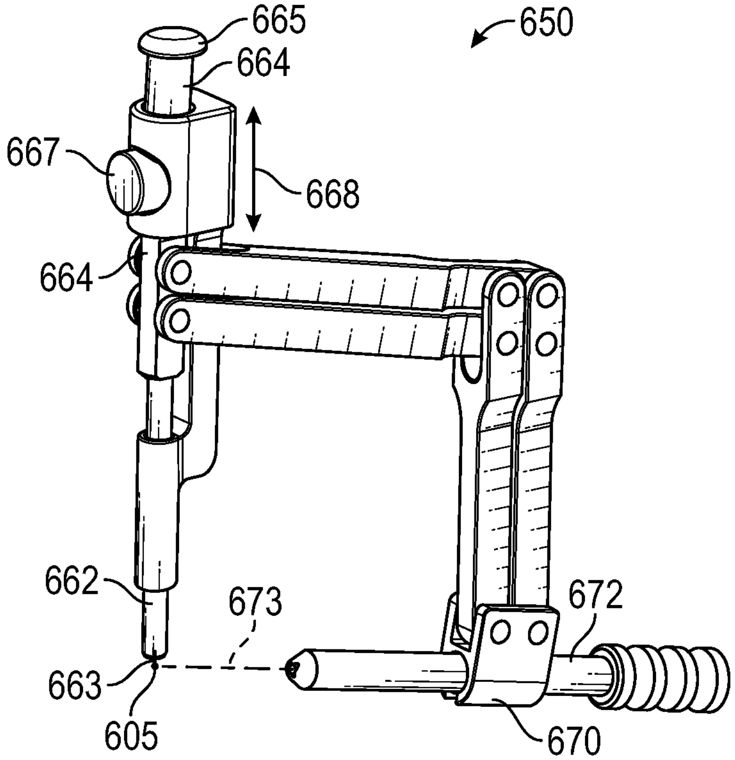
Figure 6G:
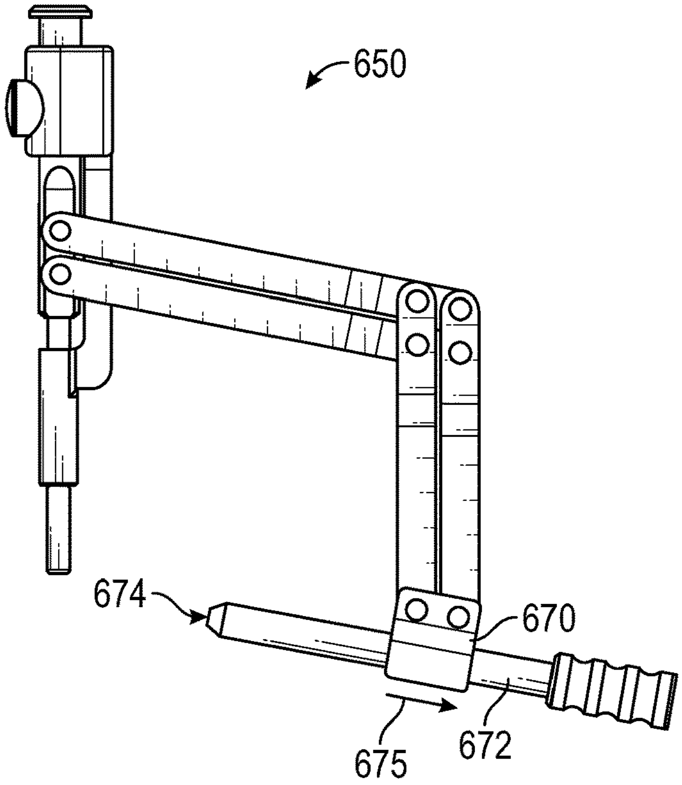
Figure 6H:
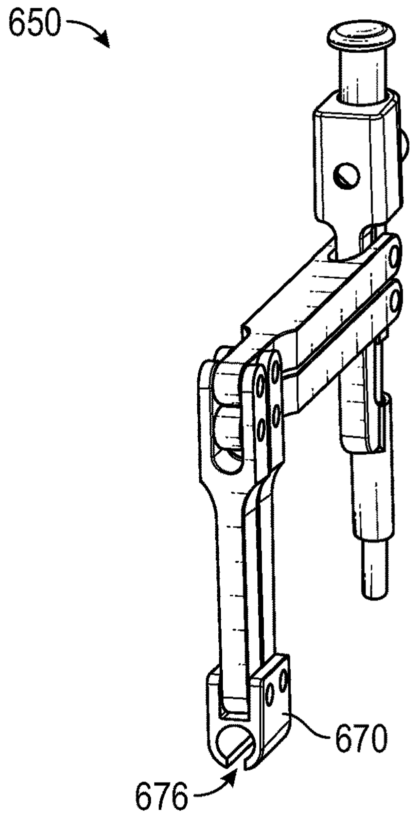

FIGS. 6E-6H depict a further example drill guide 650 configured to be used with any of the bone implant devices and components of FIGS. 1A-5F. As will be described in greater detail, the drill guide 650 provides for electable vertical positions of drilling trajectories, as well as other features which may facilitate the placement of multiple screws into a post insert component 300. FIGS. 6E and 6F are perspective views of the drill guide 650 illustrating the selection of different vertical positions. FIGS. 6G and 6H are side and perspective views, respectively, illustrating features of the drill guide 650 facilitating disengagement from a wire after placement.

The drill guide 650 includes an anchoring assembly 660, a cannula guide 670 for orienting a drill cannula 672, and a linkage 680 including parallel pairs of first linkage arms 682, 684 and second linkage arms 686, 688. Some or all components of the drill guide 650 may comprise a suitably rigid material such as a metal or metal alloy (e.g., stainless steel, titanium, or the like), a polymeric material, or other suitable material.

The anchoring assembly 660 includes an anchoring arm 664 having a tip 662 adapted to removably couple to or seat against or within the top of a penetrable post (e.g., the post insert component 300, post insert component 380, or post insert member 480) or of a component containing a penetrable portion (e.g., the staple component 450 or the bone screw component 550 described elsewhere herein). The tip 662 has a cylindrical profile suitable for seating within the central aperture 305 of the post insert component 300. The cylindrical profile of the tip 662 may have a diameter approximately equal to or slightly smaller than an inner diameter of the central aperture 305 such that the tip 662 can be stably seated within the central aperture 305 while being rotatable about the central axis 101 (FIGS. 1A, 1B). In other embodiments, the tip 622 may have a different profile which may be suitably sized and shaped to mate with the desired component. The anchoring arm 664 is oriented along an anchoring assembly axis 663 (FIG. 6F) which passes through the center of the cylindrical profile. The anchoring assembly axis 663 may be coincident with the central axis 101 when the tip 662 is seated within the aperture 305 of a post component 300 of the implant 100.

The anchoring arm 664 is slidably mounted within the anchoring assembly 660. A collar 666 surrounds the anchoring arm 664 at an upper end opposite the tip 662, such that the anchoring arm 664 can slide vertically along the directions indicated by arrow 668. The linkage 680 coupling the anchoring assembly 660 to the cannula guide 670 connects to the anchoring arm 664 at pivot joints 661. The linkage arms 682, 684, 686, 688 and pivot joints 683, 685, 671 are configured similarly to the linkage arms 632, 634, 636, 638 and pivot joints 633, 635, 621 of the drill guide 600 of FIGS. 6A-6D. The configuration of the linkage arms 682, 684, 686, 688 and pivot joints 683, 685, 671 thus fixes the location of the intersection 605 of the anchoring assembly axis 663 and the cannula axis 673 relative to the tip 662 of the anchoring arm 664. Accordingly, vertical movement of the anchoring arm 664 relative to the anchoring assembly 660, which remains fixed relative to the post insert component 300, changes the distance along the length of the post insert component 300 at which a drill or wire will intersect the post insert component 300 when inserted through the cannula 672.

Motion of the anchoring arm 664 is constrained to a lower limit defined by a cap 665 at an upper end of the anchoring arm 664, and an upper limit defined by linkage arms 682, 684. The collar 666 can include a button 667 configured to engage with the anchoring arm 664 within the collar 666 so as to allow vertical motion of the anchoring arm 664 when the button 667 is depressed and to lock or inhibit motion of the anchoring arm 664 when released. In some embodiments, the anchoring arm 664 and/or the button 667 may include a plurality of detents that allow locking of the position of the anchoring arm 664 at several predetermined positions, or may allow locking of the shaft at any desired position between the upper and lower limits.

The cannula guide 670 of the drill guide 650 is configured to facilitate disengagement from a placed wire. As shown in FIGS. 6G and 6H, the cannula guide 670 includes a slot 676 sized to accommodate movement of a wire, pin, or similarly sized structure therethrough, along a radial direction perpendicular to the cannula 672. After placement of a wire through the lumen 674 of the cannula 672, the drill guide 650 may be disengaged from the wire by sliding the cannula 672 out of the cannula guide 670 along direction 675. The cannula guide 670 may then be moved upward such that the wire passes through the slot 676. In this manner, the drill guide can be moved for placement of a subsequent wire, pin, or the like, without requiring a user to remove the drill guide 650 from the post insert component 300 and slide the cannula guide 670 along the full length of the existing wire for removal. Use of the drill guide 650 is described in greater detail below with reference to FIGS. 21-29.

With reference to FIGS. 7-15, an example internal fixation procedure for placing the implant 100 of FIGS. 1A-1D will be described. Although the procedure of FIGS. 7-15 illustrates placing a particular configuration of the implant 100, it will be understood that the components and steps illustrated and described with reference to FIGS. 7-15 may equally be applied in different sequences and/or with different combinations of components to place the implant 100 in any desired configuration.

Figure 7:
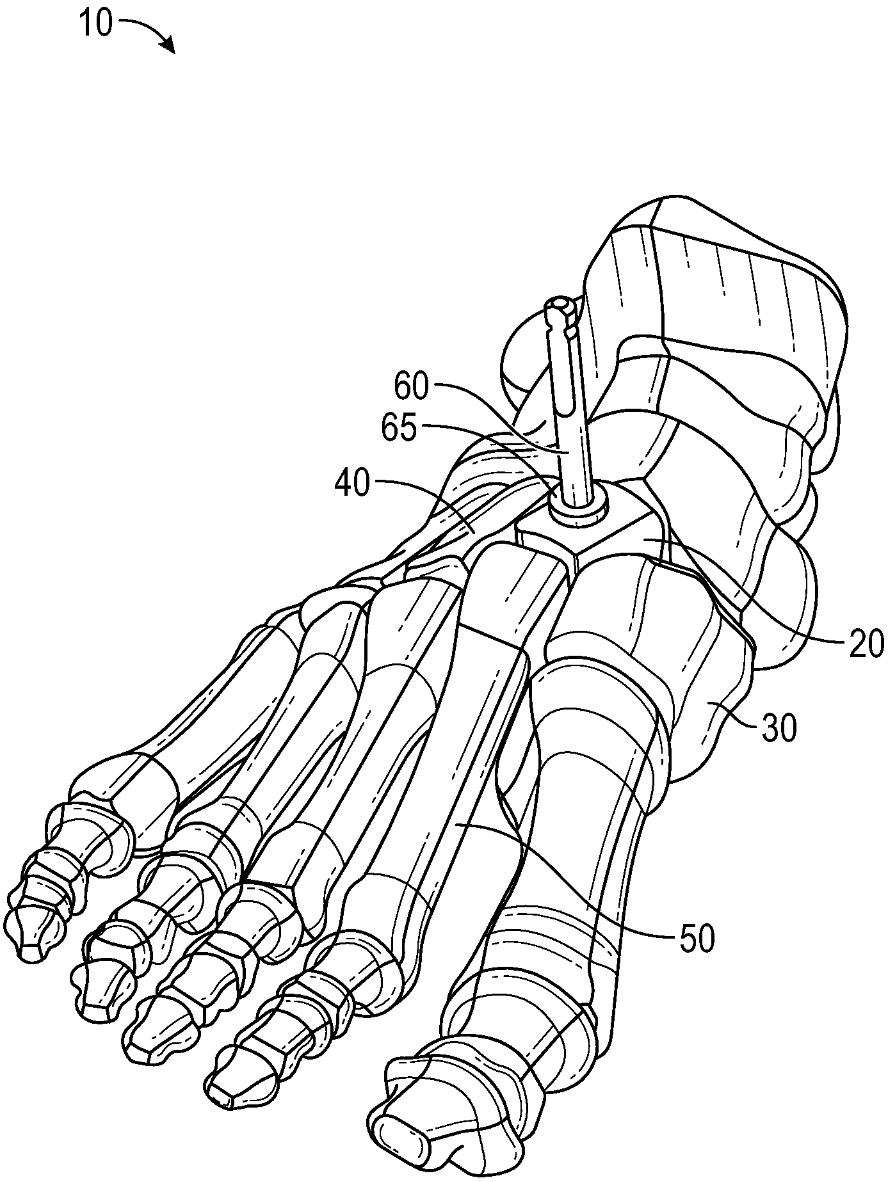
FIGS. 7-15 are perspective views of the bones of a foot, sequentially illustrating an example internal fixation procedure using the example modular bone implant device of FIGS. 1A-1E.

FIG. 7 depicts the bones 10 of an example human foot prior to placement of the implant 100. In the example procedure of FIGS. 7-15, the implant 100 will be placed to stabilize and join an intermediate cuneiform bone 20 to the adjacent medial cuneiform bone 30 and second metatarsal 50. However, various other bones of the foot (e.g., other midfoot bones such as a lateral cuneiform bone 40, cuboid bone, or navicular bone, hindfoot bones such as a talus bone or calcaneus bone, other metatarsals 1008, etc.) or other bones elsewhere in the body may also be joined with using the implant 100. In some implementations, the modular customizability of the implant 100 may make the implant 100 especially well-suited to locations such as the midfoot, where a plurality of small and/or irregular bones may need to be joined, and where there is a relatively high incidence of skeletal geometry variation between different individual implant placement locations.

As shown in FIG. 7, the procedure may begin by determining a location for the central axis 101 where the post insert component 300 (FIGS. 1A-1E) will be placed. The location for the post insert component 300 may be any location along a bone selected to serve as an anchor for the implant. In some embodiments, it may be desirable to select a relatively strong bone and/or the strongest bone of a set of bones that will be fixed using the implant. A hole may then be drilled using a drill bit 60 or shaft having a diameter suitable to accommodate the expandable tabs 220 of a bone plate component 200 prior to expansion. The hole may be drilled to a depth suitable to accommodate the depth of the plug insert component 300 of the implant 100 to be placed. In some embodiments, the drill bit 60 may be designed to correspond to a particular size of post insert component 300 (e.g., may be provided in a kit with other components of the implant 100) and may have a collar 65 configured to prevent the drill bit 60 from drilling into the bone beyond a predetermined depth for the post insert component 300. In the example procedure of FIGS. 7-15, the drill bit 60 is used to drill the appropriately sized hole in the intermediate cuneiform bone 20.

Figure 8:
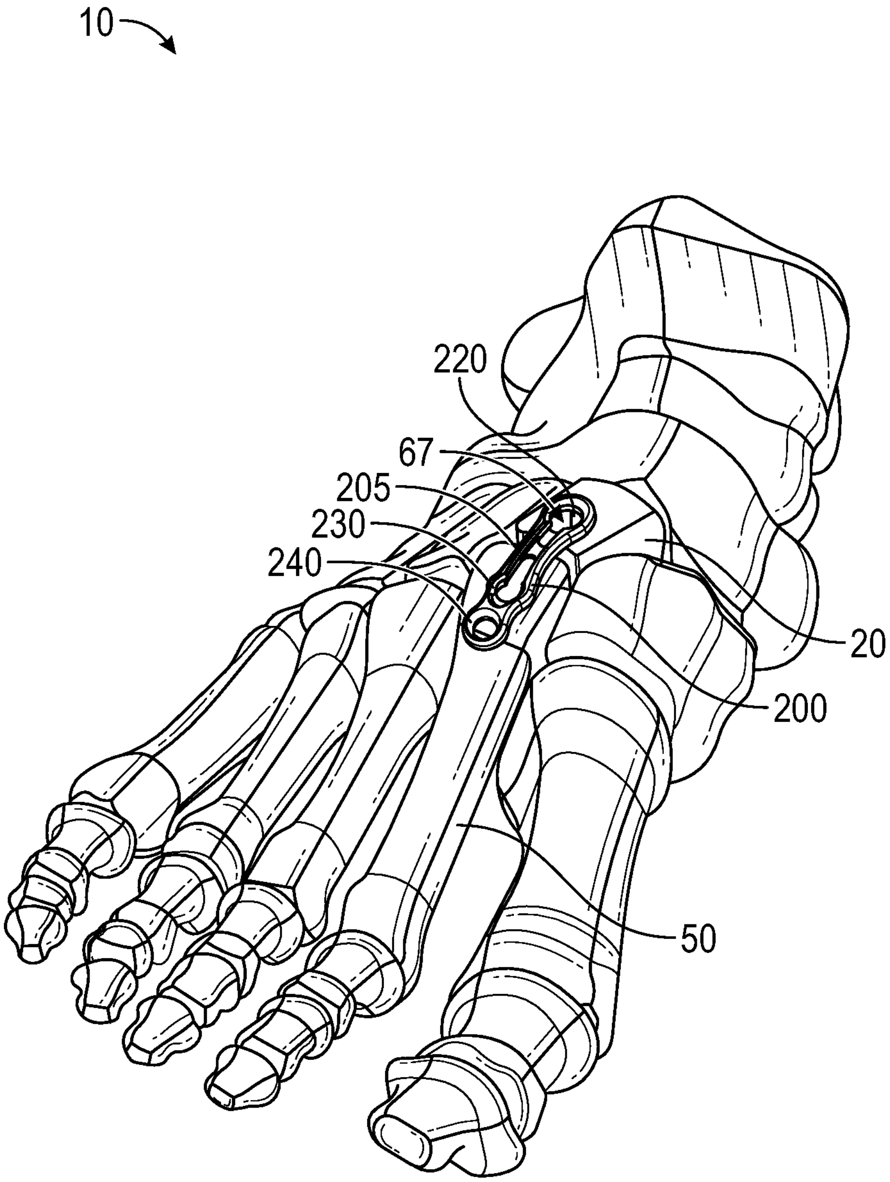

Referring now to FIG. 8, after a hole 67 has been drilled in the intermediate cuneiform bone 20, the bone plate component 200 may be placed onto the midfoot bones such that the expandable tabs 220 are seated within the hole 67. Prior to insertion of a plug insert component 300, the expandable tabs 220 may be rotatable within the hole 67 such that the bone plate component 200 can be rotated into a desired rotational orientation in which the staple aperture and the screw aperture 240 overlie the desired structure where they will be fixed. In the example procedure of FIGS. 7-15, the bone plate component 200 is placed such that the staple aperture 230 and the screw aperture 240 overlie the second metatarsal 50. The expandable tabs 220 may preferably be inserted into the hole 67 until the bone-facing surface of the body 205 of the bone plate component 200 is in contact with the surface of the intermediate cuneiform bone 20.

Figure 9:
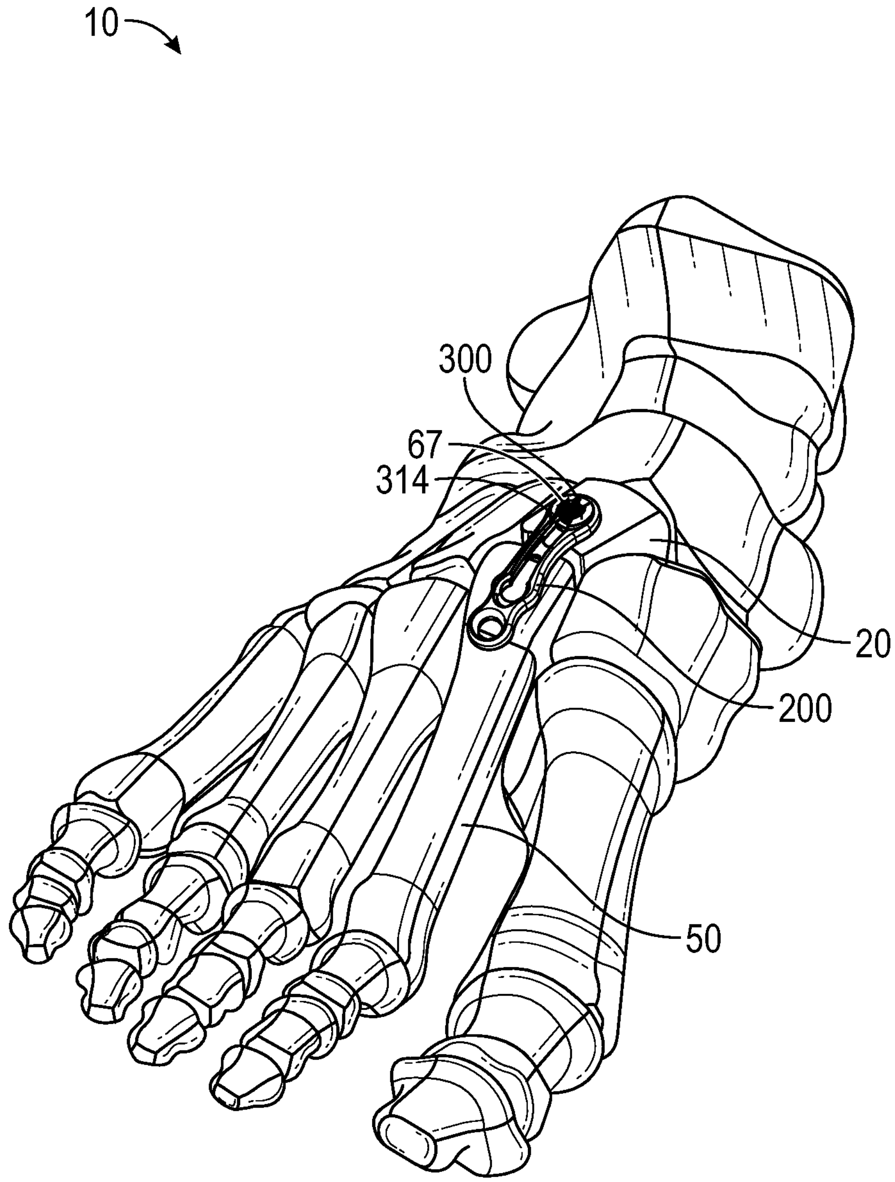

Continuing with reference to FIG. 9, once the bone plate component 200 has been placed in the appropriate rotational orientation relative to the hole 67 and the second metatarsal 50, a post insert component 300 may be placed within the hole 67. In some embodiments, the post insert component 300 may be inserted into the hole 67 by hand or using a post installation tool configured to releasably engage the interior of the aperture 305 (FIGS. 3A-3C) of the post insert component 300. The post insert component 300 may be rotated before, during, and/or after insertion such that the cutaway 314 is aligned with the length of the bone plate component. As the post insert component 300 is inserted to the configuration shown in FIG. 9, the expandable tabs 220 are pressed outward such that the bone engaging features 222 (FIGS. 1A-1D) grip the bone along the interior surface of the hole 67 to secure the bone plate component 200 to the intermediate cuneiform bone 20.

Figure 10:
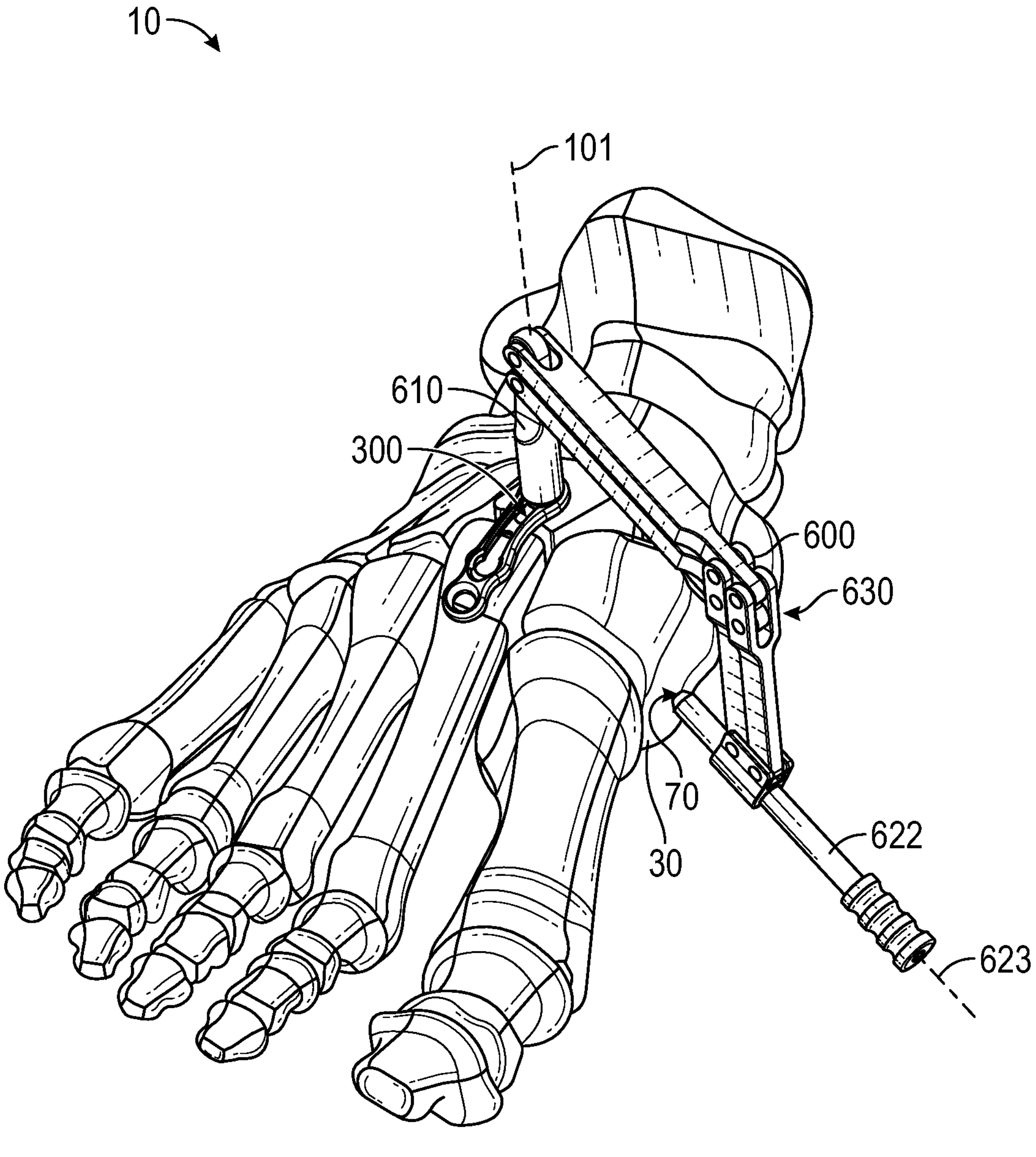

Continuing to FIG. 10, when the post insert component 300 has been placed, a drill guide 600 can be used to establish one or more screw paths targeting the post insert component 300 within the foot bones 10. The anchoring arm 610 can be placed onto the post inset component 300 such that the tip 612 (FIGS. 6A-6C, not visible in FIG. 10) of the anchoring arm 610 is seated within the aperture 305 (FIGS. 3A-3C) of the post insert component 300. The drill guide 600 may then be rotated about the central axis 101 and the cannula 622 can be moved upward or downward to a position in which an inner end of the cannula 622 rests against the surface of the medial cuneiform bone 30 at a desired screw entry location 70. As described above with reference to FIGS. 6A-6D, the linkage 630 of the drill guide 600 automatically adjusts the angle of the cannula axis 623 to define a screw path that targets the body of the post insert component 300 within the intermediate cuneiform bone 20.

Figure 11A:
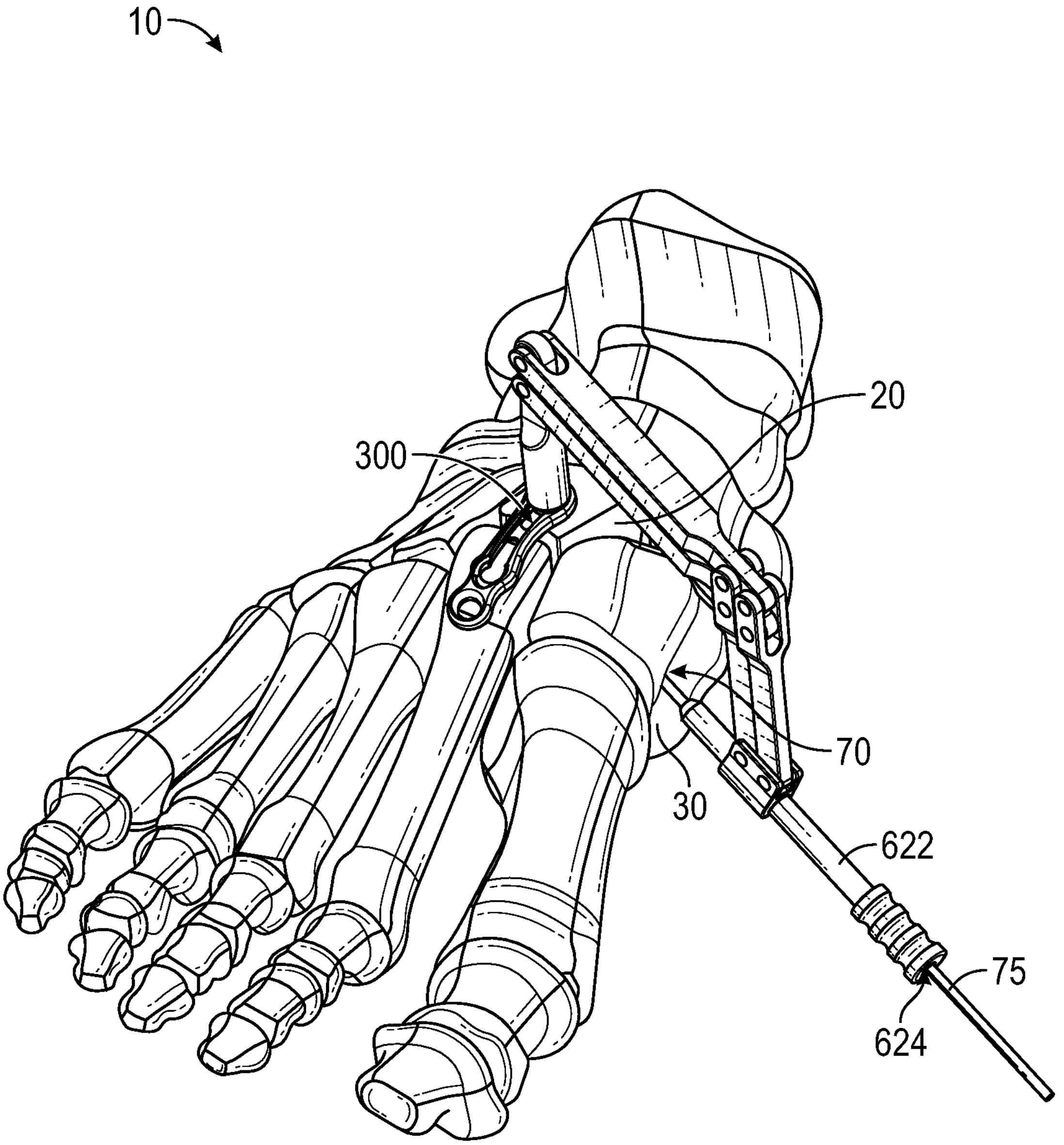
Figure 11B:
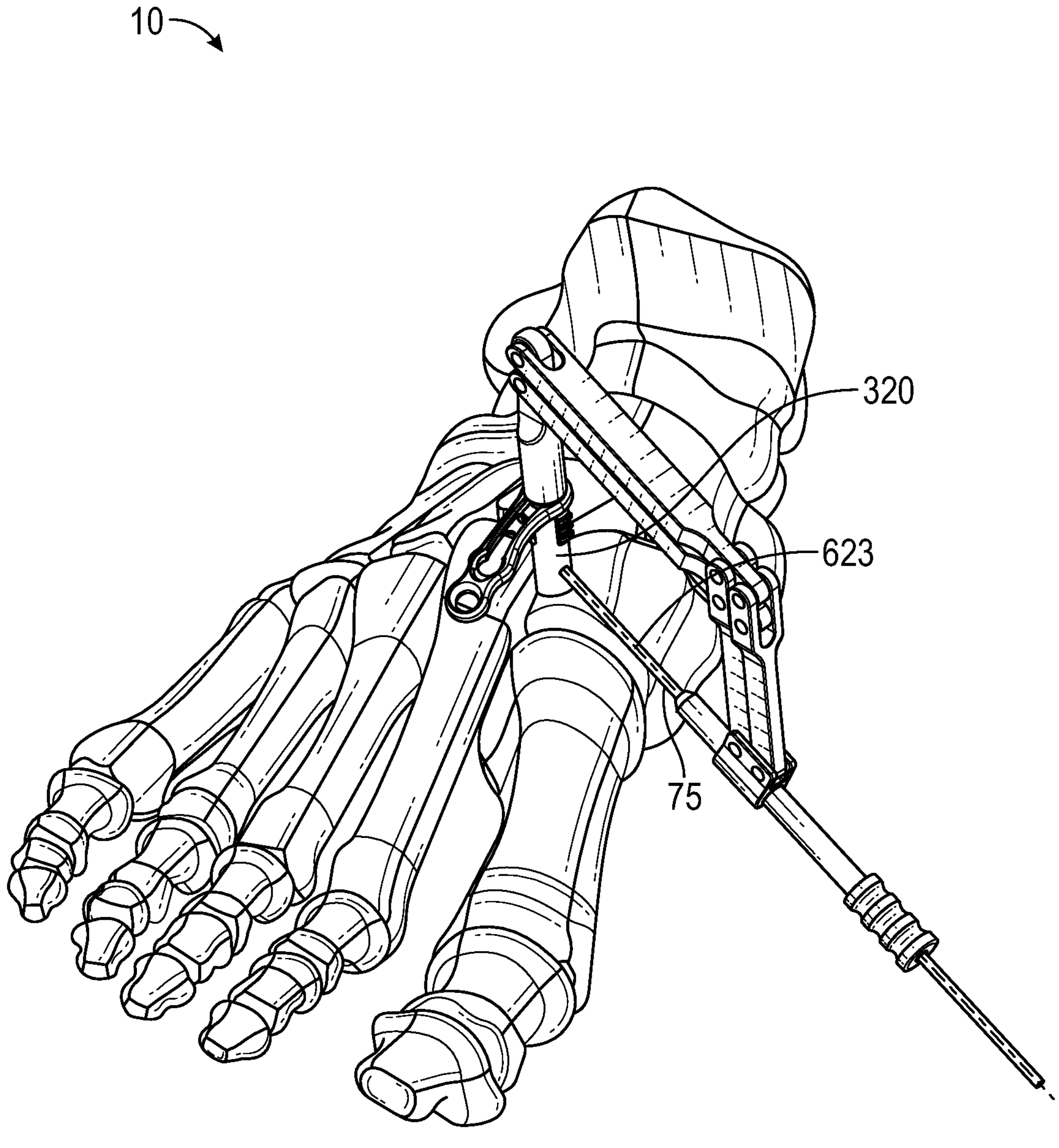

Continuing to FIGS. 11A and 11B, a wire 75, pin, or other guide structure (e.g., a K-wire or the like) is inserted through the lumen 624 of the cannula 622 such that the wire 75 enters the medial cuneiform bone 30 at the screw entry location 70 along the cannula axis 623. In some embodiments, a pilot hole may be pre-drilled for the wire 75, such as by a drill with a drill bit sized to fit through the lumen 624. The wire 75 may be inserted through the medial cuneiform bone 30 and into the intermediate cuneiform bone 20 until the wire 75 abuts or penetrates the body 320 of the post insert component 300. FIG. 11B illustrates the configuration of FIG. 11A, with the intermediate cuneiform bone 20 and the medial cuneiform bone 30 hidden to illustrate the orientation of the wire 75 with respect to the body 320 of the post insert component 300.

Figure 12:
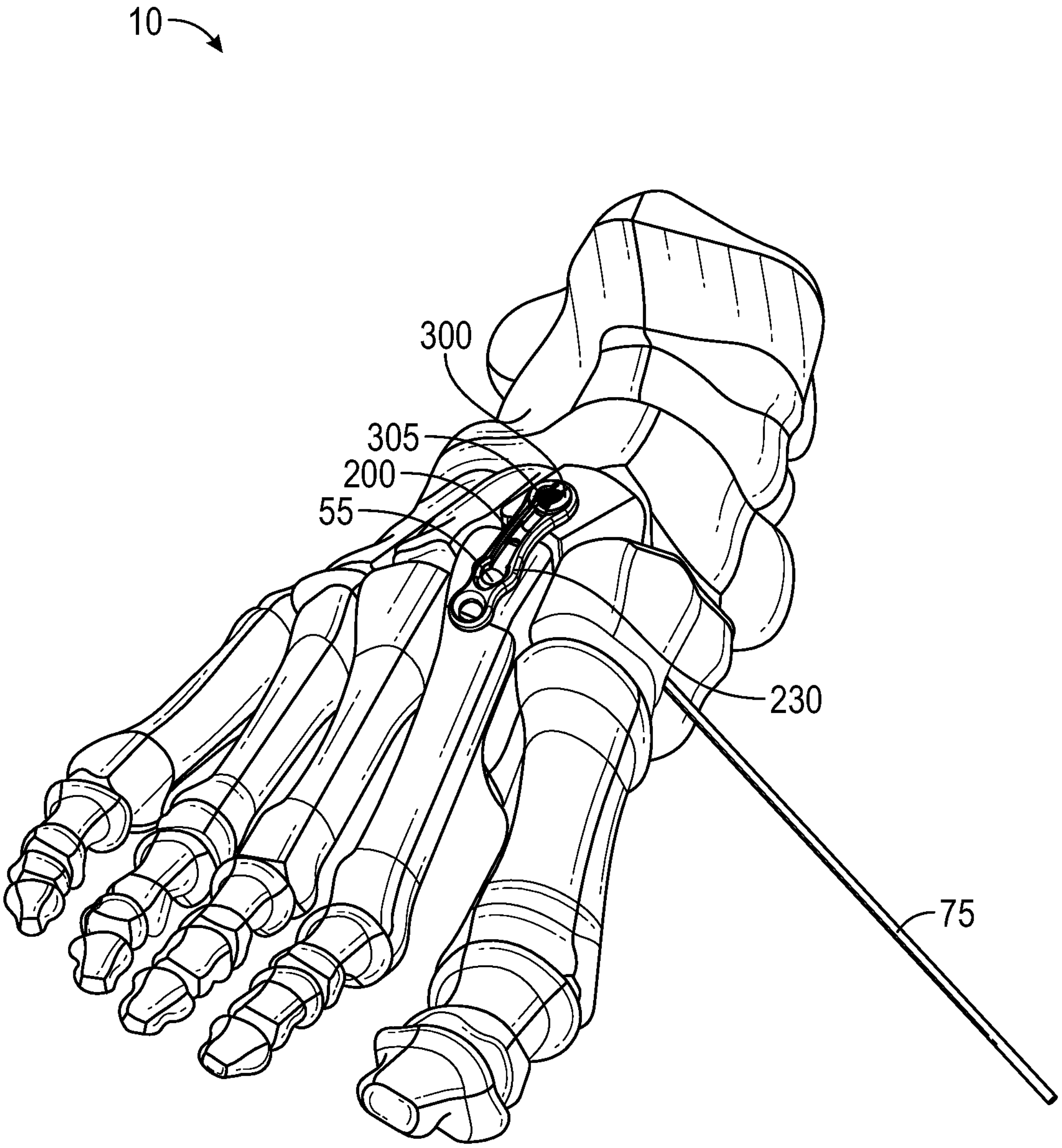

After the insertion of the wire 75 as shown in FIGS. 11A and 11B, the internal fixation procedure continues to FIG. 12, as the drill guide 600 is removed from the post insert component 300. In some embodiments, the drill guide 600 may be removed by withdrawing the tip 612 of the anchoring arm 610 (FIGS. 6A-6D) from the aperture 305 of the post insert component 300, followed by sliding cannula 622 and cannula guide 620 away from the bones 10 of the foot and clear of the wire 75. The wire 75 remains within the medial cuneiform bone 30 and the intermediate cuneiform bone 20 to maintain the screw path for subsequent insertion of a lateral screw. If any additional lateral screws will be inserted, the drill guide 600 may be reused to place one or more additional wires defining additional lateral screw paths targeting the post insert component 300. To facilitate insertion of a staple component, a hole 55 may be drilled into the second metatarsal 50 through the staple aperture 230 of the bone plate component 200 to accommodate the bone engaging member 420 (FIGS. 4A-4C) of the staple component.

Figure 13:
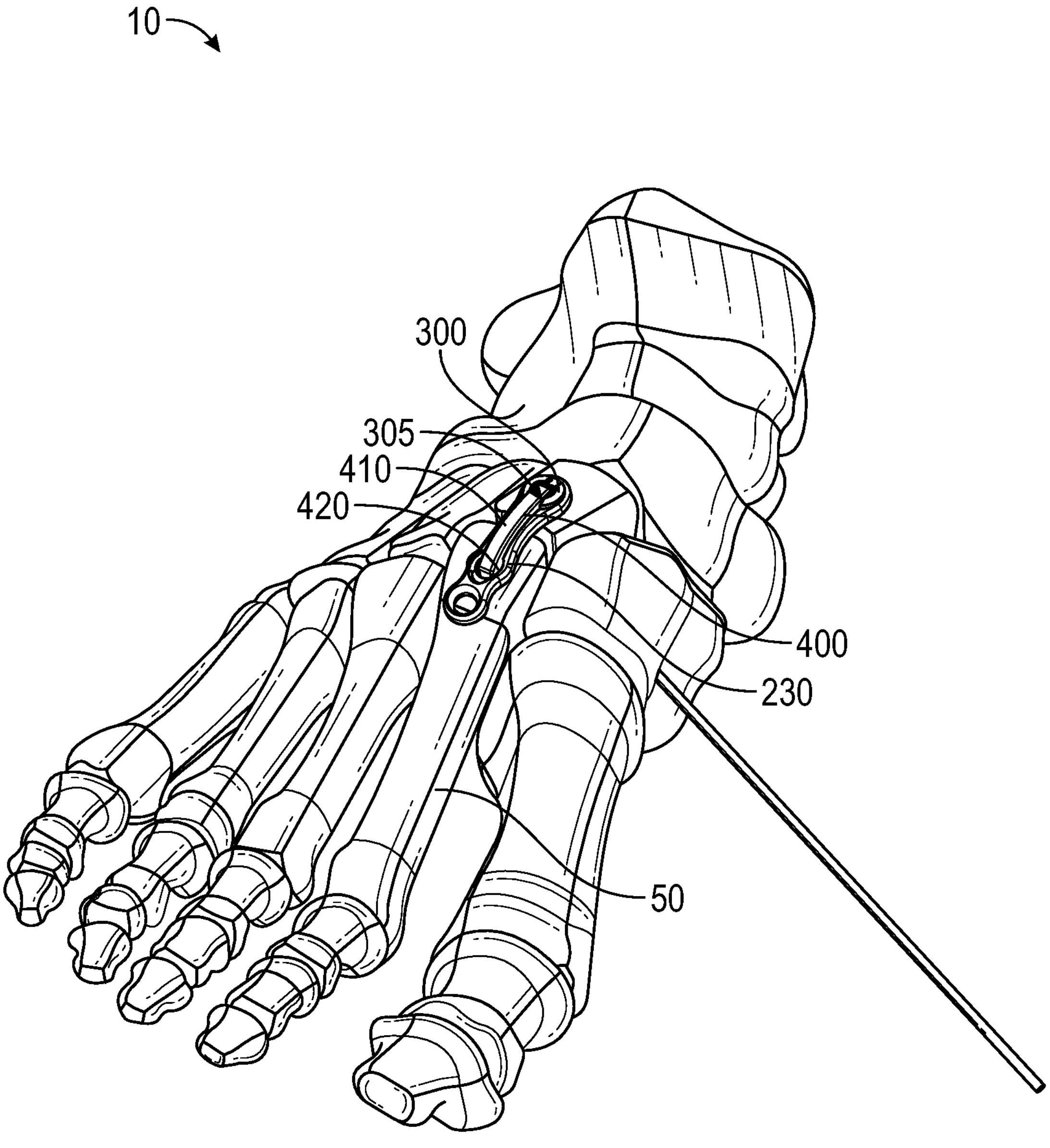

If no additional lateral screws are to be included in the implant, a staple component 400 can be inserted, as shown in FIG. 13, to fix the second metatarsal 50 to the intermediate cuneiform bone 20. The staple component 400 can be placed by simultaneously inserting the bone engaging member 420 through the staple aperture 230 into the hole 55 (FIG. 12) and inserting the post engaging member 430 (FIGS. 4A-4C, not visible in FIG. 13) into the aperture 305 of the post insert component 300. In some embodiments, the staple component 400 may be deformable. If the staple component 400 is deformable, the staple component 400 may be inserted with the bridge 410 of the staple component deformed into a substantially linear configuration, and may be released to create a compressive force holding together the second metatarsal 50 and the intermediate cuneiform bone 20.

Figure 14A:
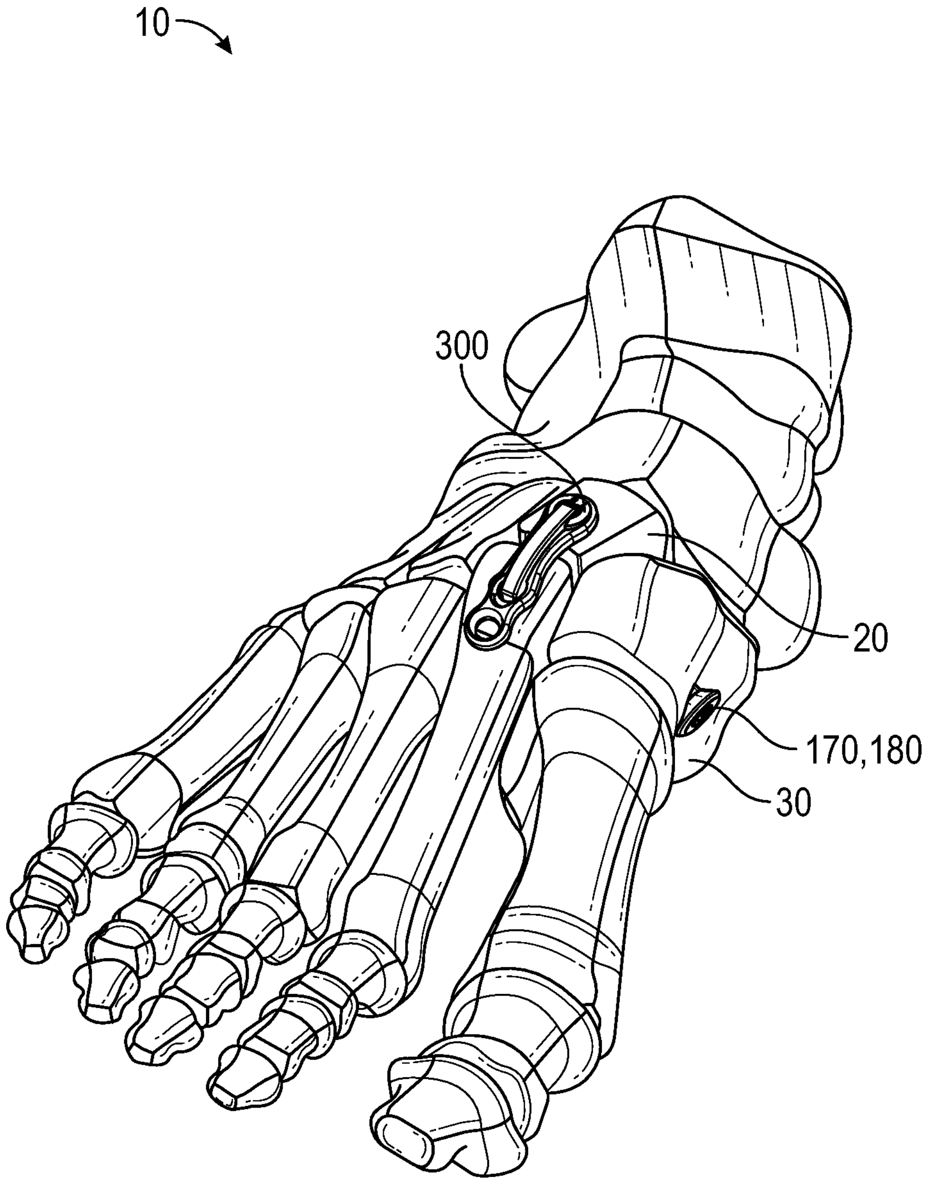
Figure 14B:
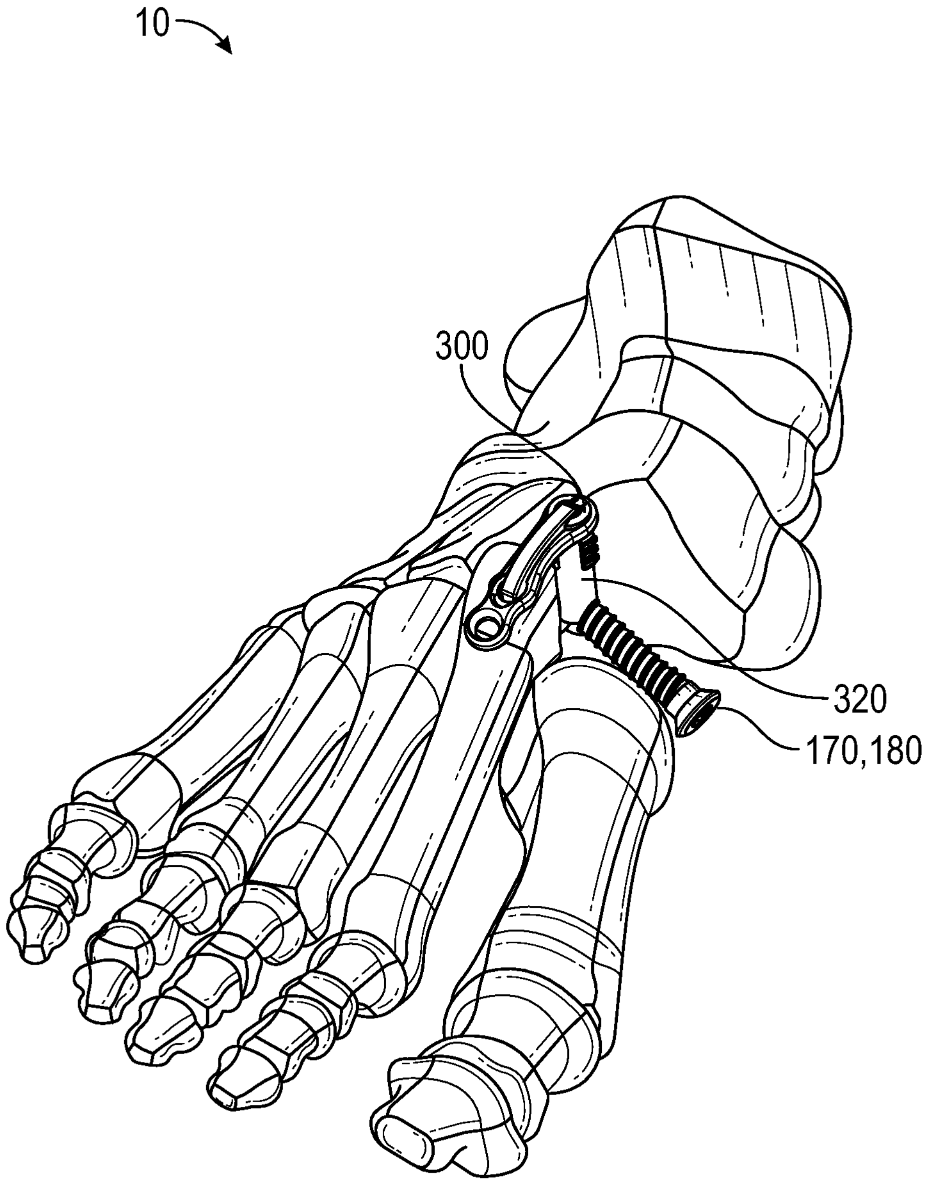

As shown in FIGS. 14A and 14B, after the staple component 400 is placed, lateral screws can be inserted along any screw paths established using the drill guide 600 (as described with reference to FIGS. 10-12). FIG. 14B illustrates the configuration of FIG. 14A, with the intermediate cuneiform bone 20 and the medial cuneiform bone 30 hidden to illustrate the orientation of the solid lateral screw 170 or cannulated lateral screw 180 with respect to the body 320 of the post insert component 300. In the example procedure of FIGS. 7-15, a lateral screw such as a solid lateral screw 170 or a cannulated lateral screw 180 can be driven through the medial cuneiform bone 30 and the intermediate cuneiform bone 20, and into the body 320 of the post insert component 300. The lateral screws may be placed by any suitable method for placing a screw based on an existing guide such as a wire or pin. For example, in some embodiments a cannulated drill bit may be used to drill a pilot hole along the path of the wire, and a solid lateral screw 170 may then be driven into the pilot hole. In other embodiments, a cannulated lateral screw 180 may be driven while the wire remains within the bone.

Figure 15:
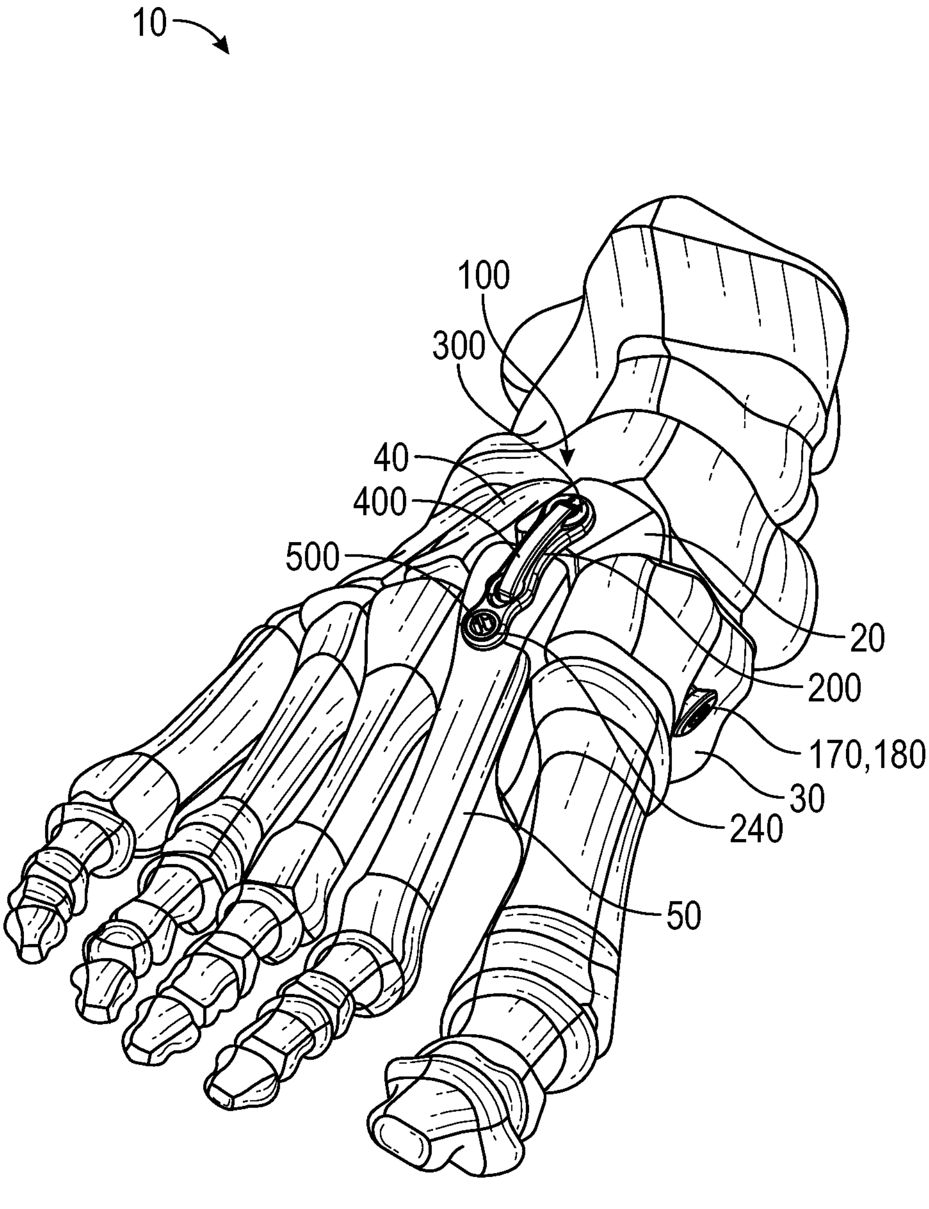

Referring now to FIG. 15, the implant placement procedure of FIGS. 7-15 concludes by inserting a bone screw component 500 into the second metatarsal 50 through the screw aperture 240 of the bone plate component 200 to complete the assembly and placement of the implant 100. The bone screw component 500 may be, for example, the self-tapping bone screw component 500 illustrated in FIGS. 5A-5C. In some embodiments, a pilot hole may be drilled through the screw aperture 240 prior to placement of the bone screw component 500. In the final assembled state shown in FIG. 15, the bone screw component 500 firmly fixes the second metatarsal 50 to the intermediate cuneiform bone 20 through the bone plate component 20 and the compressive force of the staple component 400. The medial cuneiform bone 30 is also securely fixed relative to the intermediate cuneiform bone 20 and the second metatarsal 50 by the lateral screw 170, 180, which is partially seated within the body of the post insert component 300 of the implant 100. Accordingly, the example process of FIGS. 7-15 allows the example implant 100 to be assembled in situ within a midfoot or other skeletal location to provide robust internal fixation customized to the unique geometry or other properties of an individual implant location.

Figure 16C:
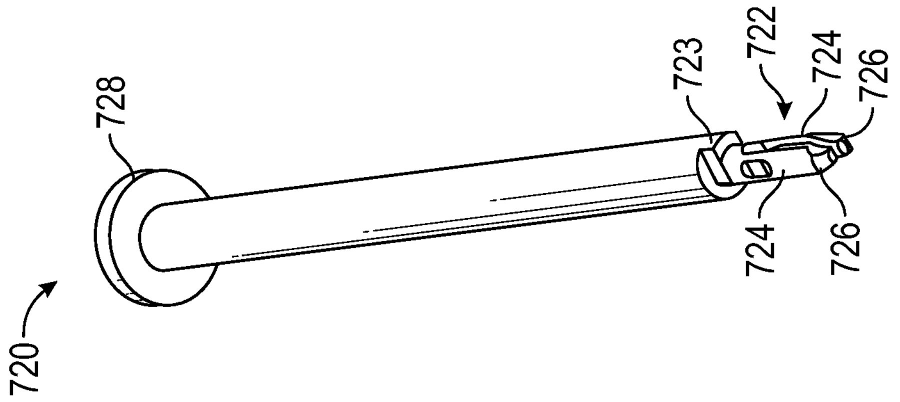
FIGS. 16A-16G depict an example post inserter configured for insertion of post insert components described herein.
Figure 16B:
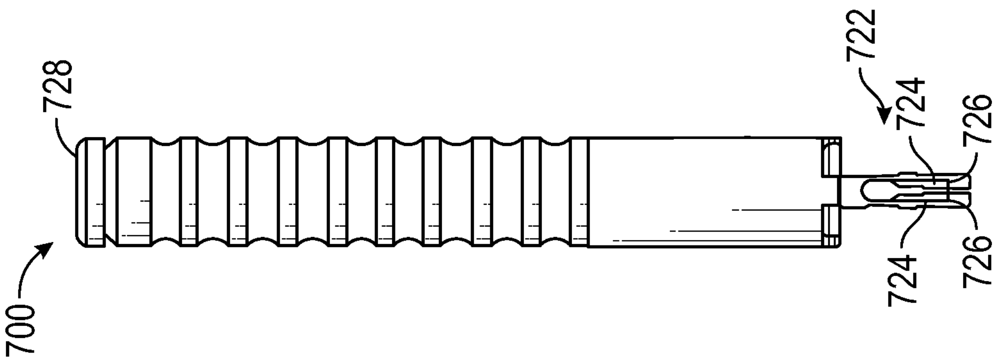
Figure 16A:
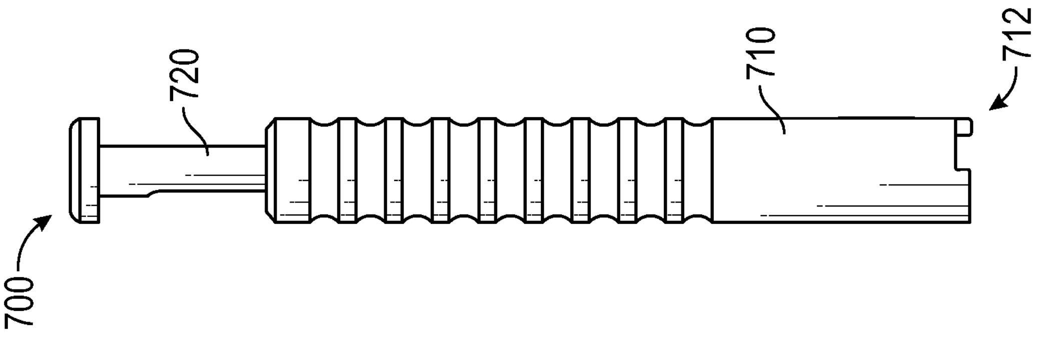
Figure 16D:
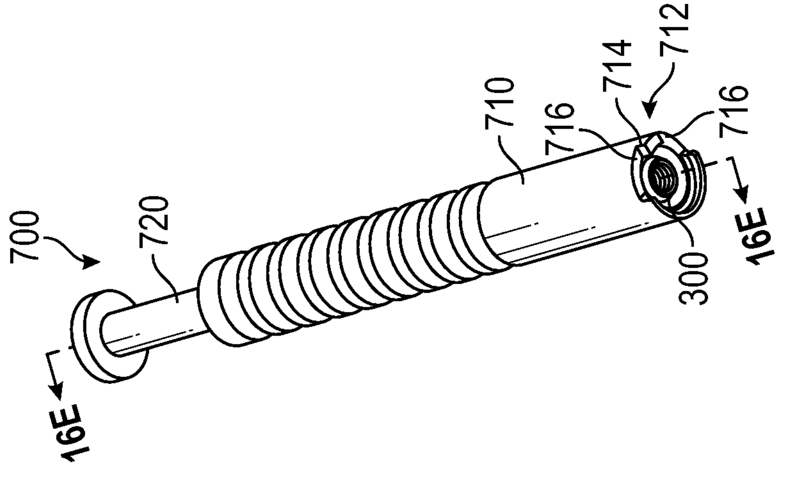
Figure 16E:
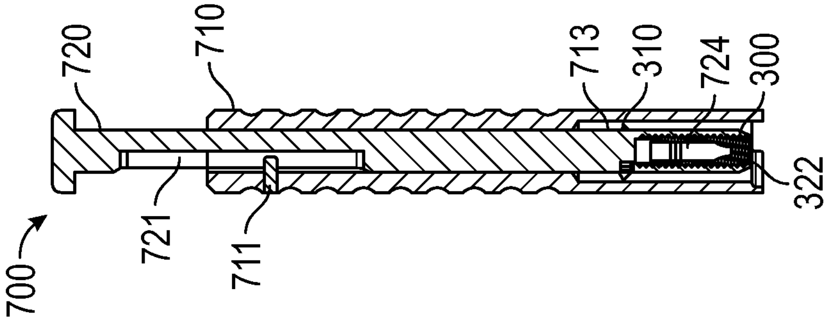
Figure 16F:
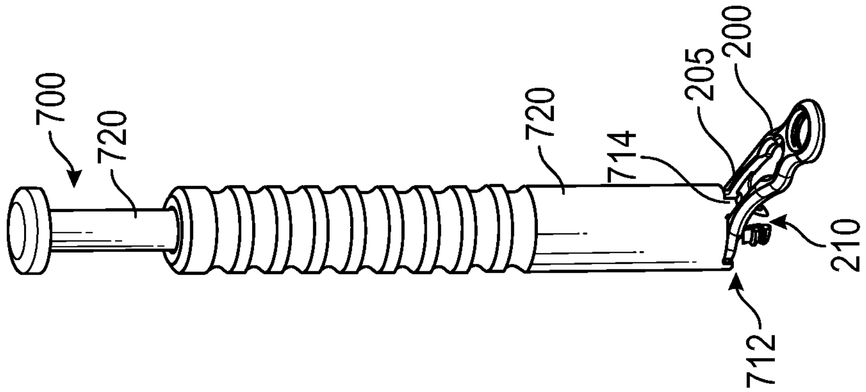
Figure 16G:
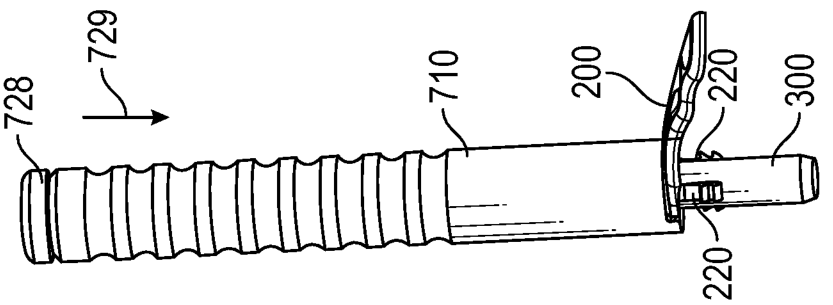

FIGS. 16A-16G depict an example post inserter 700 configured for insertion of post insert components described herein, such as the post insert component 300. The post inserter 700 includes a sleeve 710 and a shaft 720. FIGS. 16A and 16B depict the post inserter 700 in retracted and extended configurations, respectively. FIG. 16C depicts the shaft 720 alone. FIGS. 16D and 16E depict the post inserter 700 in the retracted configuration with a post insert component 300 attached thereto prior to placement, FIG. 16E being a cross-sectional view taken about the line 16E-16E in FIG. 16D. FIGS. 16F and 16G illustrate the placement of a post insert component 300 within a bone plate component 200.

The shaft 720 is slidably disposed within the sleeve 710. The shaft 720 includes a cap 728 which defines a most extended position of the shaft 720 when the cap 728 abuts the sleeve 710. Within the sleeve 710, as shown in FIG. 16E, a distal cavity 713 has a diameter sufficient to accommodate the head 310 of a post insert component 300 disposed therein. At an end opposite the cap 728, the shaft 720 includes a post engaging end 722 configured to releasably secure the post insert component 300 of FIGS. 3A-3C.

The post engaging end 722 includes resilient arms 724 having protrusions 726 located thereon. The protrusions 726 may be located at a distal end of each resilient arm 724, or may be located at an intermediate location along the resilient arm 724. When coupled to a post insert component 300, as shown in FIGS. 16D-16G, the protrusions 726 engage with the internal screw threads 322 of the post insert component 300 to secure the post insert component 300 to the post engaging end 722 of the shaft 720. In some embodiments, the protrusions 726 may be configured to engage with other features of a post insert component 300, such as grooves, a roughened interior surface, or the like. The post engaging end 722 further includes a tab 723 sized to seat within the cutaway 314 of the post inset component 300 (FIGS. 3A-3B). Thus, when the post insert component 300 is coupled to the shaft 720, the tab 723 maintains a fixed rotational orientation of the post insert component 300 relative to the shaft 720.

The sleeve 710 includes a bone plate engaging end 712 configured to align the sleeve 710 with the bone plate component 200 of FIGS. 2A-2D. Referring jointly to FIGS. 16D and 16F, the bone plate engaging end 712 includes a tab 714 configured to seat between lateral portions of the body 205 of the bone plate 200. The bone plate engaging end 712 further includes recesses 716 configured to accommodate the lateral portions of the body 205 therethrough, such that the post inserter 700 seats securely onto the bone plate component 200 in a fixed rotational orientation as shown in FIG. 16F, with the central axis of the post inserter 700 aligned with the post aperture 210 of the bone plate 200.

Referring again to the cross-sectional view of FIG. 16E, the sleeve 710 further includes a dowel 711 extending at least partially into the interior portion of the sleeve 710 occupied by the shaft 720. The shaft 720 includes a corresponding slot 721 sized and shaped to accommodate the dowel 711 therein. The slot 721 extends vertically along the shaft 720, such that the portion of the dowel 711 disposed within the slot 721 fixes the rotational orientation of the shaft 720 relative to the sleeve 710. Accordingly, the combination of the tab 714 and recesses 716 of the bone plate engaging end 712 of the sleeve 710, the tab 723 of the post engaging end 722 of the shaft 720, and the dowel 711 of the sleeve 710 within the slot 721 of the shaft 720, facilitates placement of the post insert component 300 in a specified rotational orientation relative to the bone plate component 200. This fixed rotational orientation may align the cutaway 314 of the post insert component 300 with the lengthwise dimension of the bone plate component 200 to accommodate the bridge 410 of a staple component 400 (FIGS. 4A-4C) therein.

FIGS. 16F and 16G illustrate the extension of the post inserter 700 to insert the post insert component 300 within a bone plate 200. As described elsewhere herein, the insertion of the post insert component 300 between the expandable tabs 220 of the bone plate component 200 causes a normal force between the post insert component 300 and the expandable tabs 220, preventing withdrawal of the post insert component 300 from the bone plate component 200. The resilient arms 724 are sufficiently resilient to permit the protrusions 726 to withdraw and permit the post engaging end 722 of the shaft 720 to release the post insert component 300 when the post inserter 700 is pulled away after insertion of the post insert component 300. Use of the post inserter 700 is described in greater detail with reference to FIGS. 18-20.

Figure 17A:
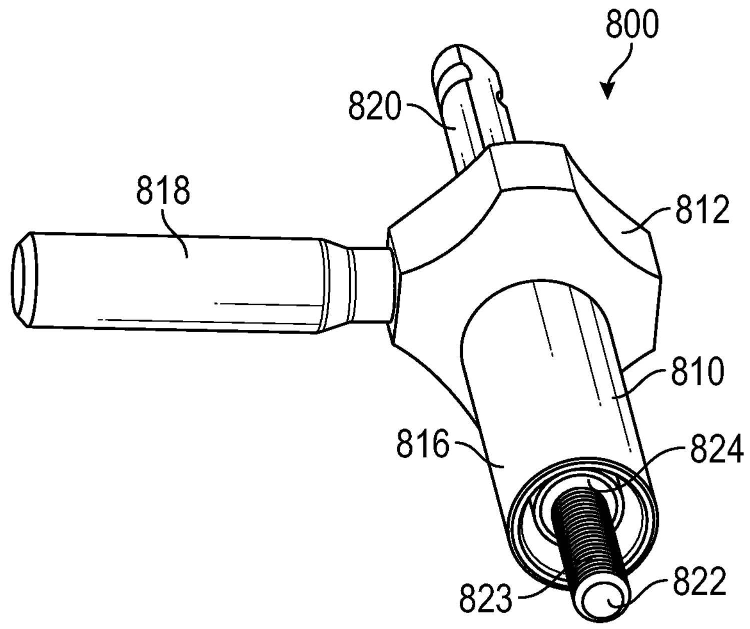
FIGS. 17A-17F depict an example extraction tool configured for removal of post insert components described herein.
Figure 17B:
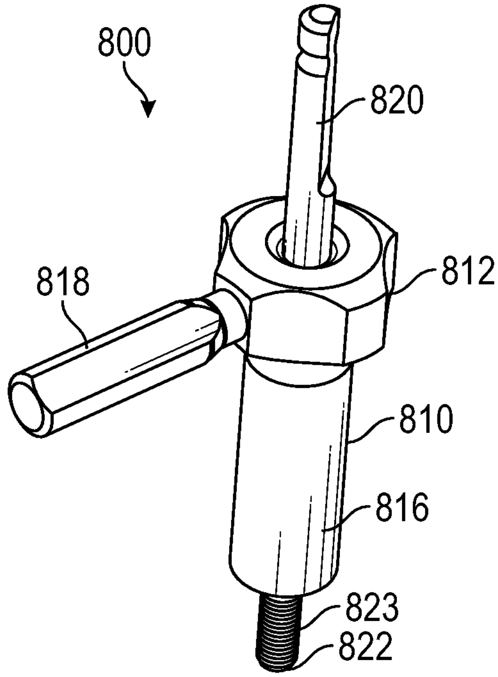
Figure 17C:
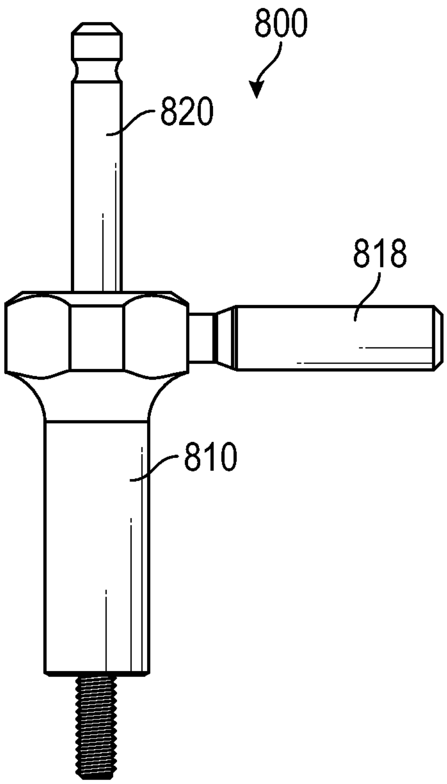
Figure 17D:
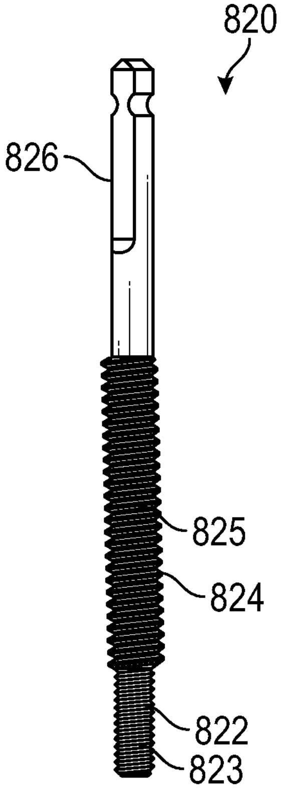
Figure 17E:
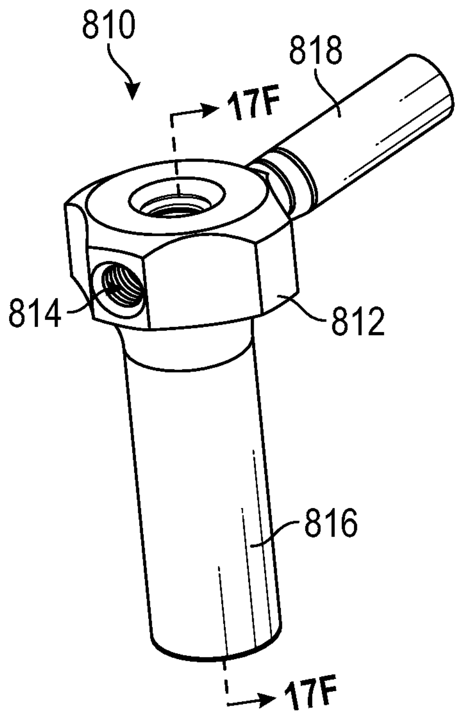
Figure 17F:
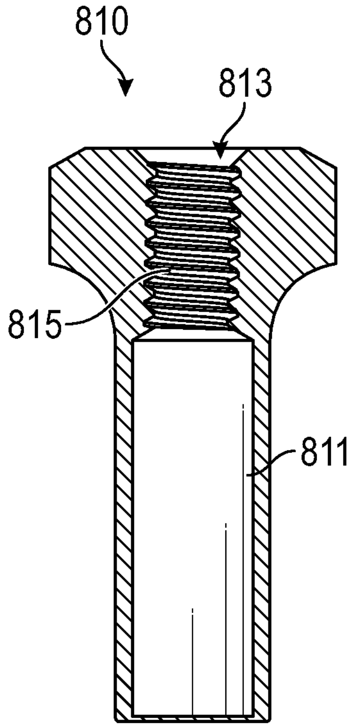

FIGS. 17A-17F depict an example extraction tool 800 configured for removal of post insert components described herein. The extraction tool 800 includes a sleeve 810 and a shaft 820. FIGS. 17A-17C depict an assembled extractor tool 800 including the sleeve 810, the shaft 820, and an optional handle 818. FIG. 17D depicts the shaft 820 alone. FIGS. 17E and 17F depict the sleeve 810, FIG. 17F being a cross-sectional view taken about the line 17F17-F in FIG. 17E.

The shaft 820 generally comprises an elongate body, including a distal portion 822, a medial portion 824, and a proximal portion 826. The distal portion 822 includes screw threads 823 compatible with the internal screw threads 322 of the post insert component. The medial portion 824 includes screw threads 825 compatible with corresponding internal screw threads 815 of the sleeve 810. The proximal portion 826 may be shaped to be compatible with any suitable type of manual or motorized rotational driver.

The sleeve 810 includes a head 812 and a body 816. The head 812 includes one or more threaded apertures 814 for receiving an optional handle 818. A threaded aperture 813 extends through the head 812 and includes internal screw threads 815 compatible with corresponding external screw threads 825 on the medial portion 824 of the shaft 820. The body 816 includes a cavity 811 having a diameter large enough to accommodate the head 310 of a post insert component 300 (FIGS. 3A-3C) therein.

As will be described in greater detail with reference to FIGS. 30-35B, the extraction tool 800 can be used to remove a post insert component 300 from an implant 100 (FIGS. 1A-1B). The shaft 820 may be coupled to the post insert component 300 by screwing the distal portion 822 into the threaded aperture 305 of the post insert component 300. The sleeve 810 may then facilitate the removal of the shaft 820 and post insert component 300 from the bone plate component 200.

Figure 18:
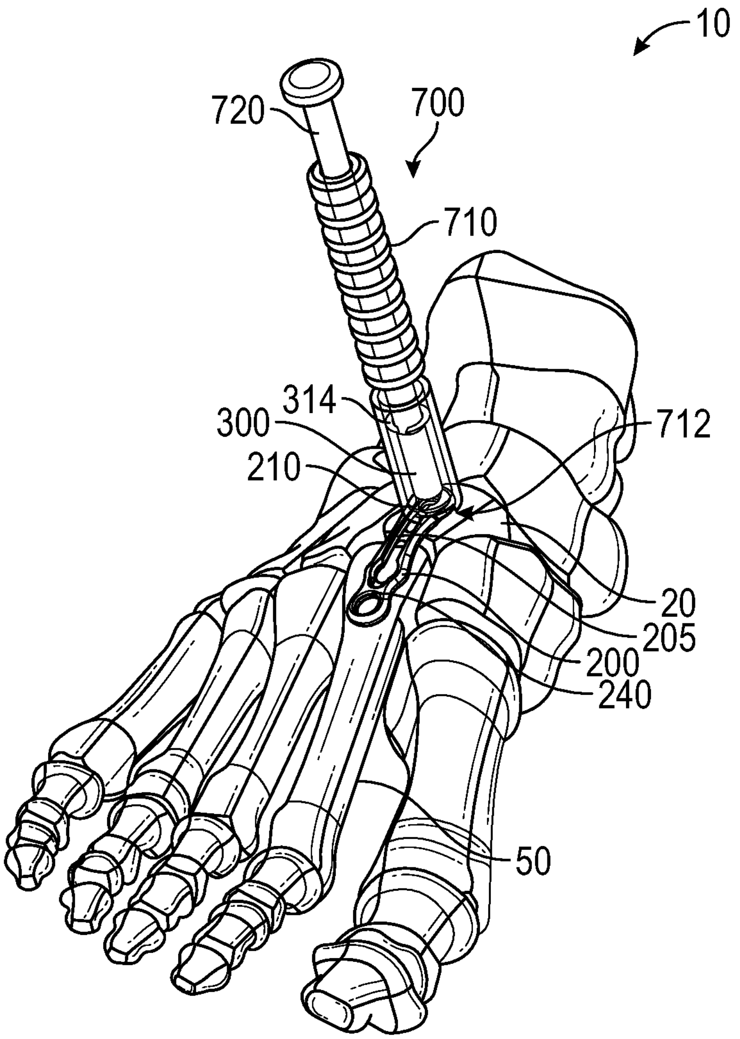
FIGS. 18-20 are perspective views of the bones of a foot, sequentially illustrating an example post insertion procedure using the example post inserter of FIGS. 16A-16G.
Figure 19:
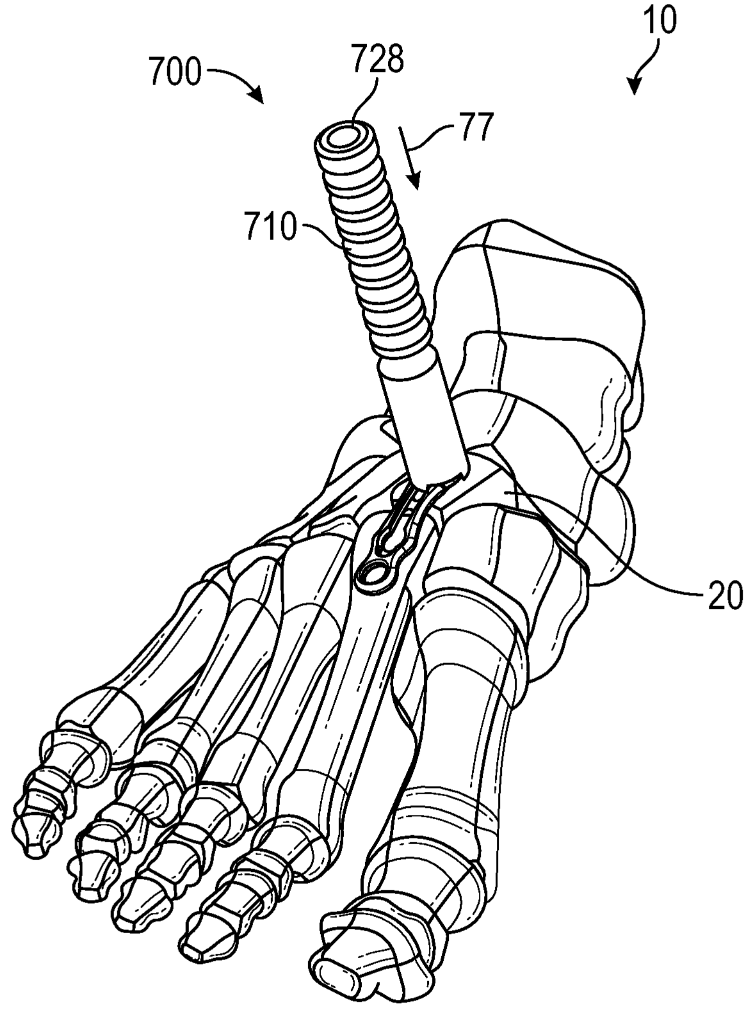
Figure 20:
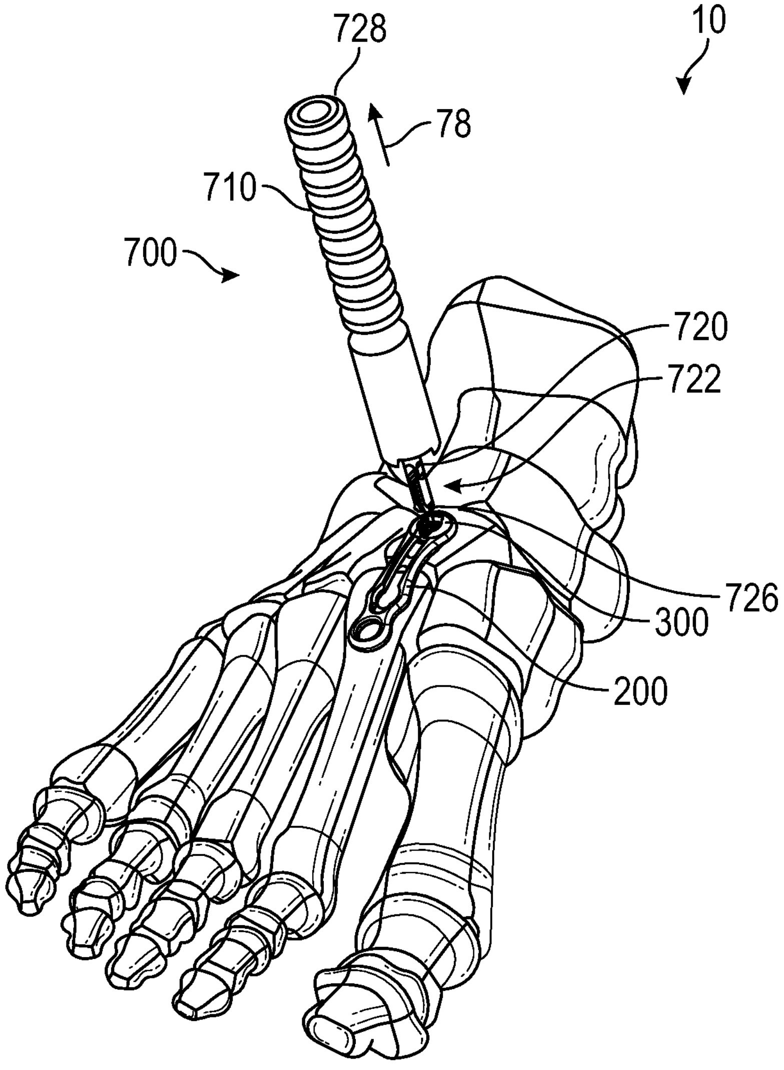

With reference to FIGS. 18-20, an example post insertion procedure using the example post inserter 700 of FIGS. 16A-16G will be described. The post insertion procedure may be performed, for example, to insert the post insert component 300 as shown between FIGS. 8 and 9 in the internal fixation procedure of FIGS. 7-15. However, it will be understood that the post insertion procedure of FIGS. 18-20 may equally be implemented in conjunction with other fixation procedures.

FIG. 18 depicts the bones 10 of an example human foot in which a bone plate component 200 has been placed with the expandable tabs 220 (FIG. 2A) disposed within a pre-drilled hole in the intermediate cuneiform bone. The configuration illustrated in FIG. 18 may be, for example, the same or similar configuration as that depicted in FIG. 8. Although FIG. 18 depicts the expandable tabs 220 of the bone plate component 200 seated within the intermediate cuneiform bone 20, any other suitable bone may be used in accordance with the present technology.

With continued reference to FIG. 18, a post inserter 700 has been loaded with a post insert component 300 and is in the retracted configuration, as shown in FIGS. 16D-16F. The sleeve 710 of the post inserter 700 is illustrated with transparency in FIG. 18 in order to show the position of the post insert component 300 secured to the shaft 720 therewithin. As described above with reference to FIGS. 16A-16G, the post inserter 700 is positioned with the features of the bone plate engaging end 712 of the shaft 710 engaging the bone plate 200, such that the cutaway 314 of the post insert component 300 will be aligned along the length of the body 205 of the bone plate component 200 when inserted into the post aperture 210.

Referring now to FIG. 19, the post inserter 700 has been transitioned to the extended configuration (e.g., as shown in FIG. 16G) to insert the post insert component 300 (not visible in FIG. 19) into the intermediate cuneiform bone 20. The post inserter 700 may be extended by moving the shaft downward along the direction indicated by arrow 77, parallel to the central axis of the implant (e.g., by manually exerting a downward force on the cap 728). The transition of the post inserter 700 from the retracted configuration to the extended configuration forces the post insert component 300, attached to the shaft 720, into the hole in the bone to a final position at least partially within the post aperture 210 of the bone plate component 200 and between the expandable tabs 220 (FIG. 16G).

Referring now to FIG. 20, the post inserter 700 is removed following insertion of the post insert component 300. The post inserter 700 may be removed by moving the sleeve 710 and the shaft 720 upward (e.g., away from the bone plate component 200) along the direction indicated by arrow 78 parallel to the central axis of the implant. The cap 728 of the shaft 720 retains the shaft 720 within the sleeve 710 as the sleeve 710 is pulled upward.

As described above with reference to FIGS. 16A-16G, the protrusions 726 retaining the post insert component 300 to the shaft 720 are resiliently mounted relative to the shaft. As the post inserter 700 is moved upward along direction 78, the frictional force between the post insert component 300 and the expandable tabs 220 (FIG. 16G) of the bone plate component 200, which tends to retain the post insert component 300 within the bone, may be stronger than that of the resiliently mounted protrusions 726 of the post inserter 700. Accordingly, when the post inserter 700 is removed from the bone, the post insert component 300 remains in its inserted position, as shown in FIG. 20 (and also as shown in FIG. 9). From the configuration of FIG. 20, the internal fixation procedure can proceed as desired (e.g., as shown in FIGS. 10-15).

With reference to FIGS. 21-29, an example screw placement procedure using the example drill guide 650 of FIGS. 6E-6H will be described. FIGS. 21-29 illustrate several advantages of the drill guide 650 when inserting multiple pins, wires, and/or screws during an internal fixation procedure, such as the internal fixation procedure of FIGS. 7-15. In some embodiments, the screw placement procedure of FIGS. 21-29 may be used in place of or in addition to the portion of the internal fixation procedure illustrated in FIGS. 10-14A. However, the screw placement procedure of FIGS. 21-29 may equally be implemented in conjunction with other internal fixation procedures.

Figure 21:
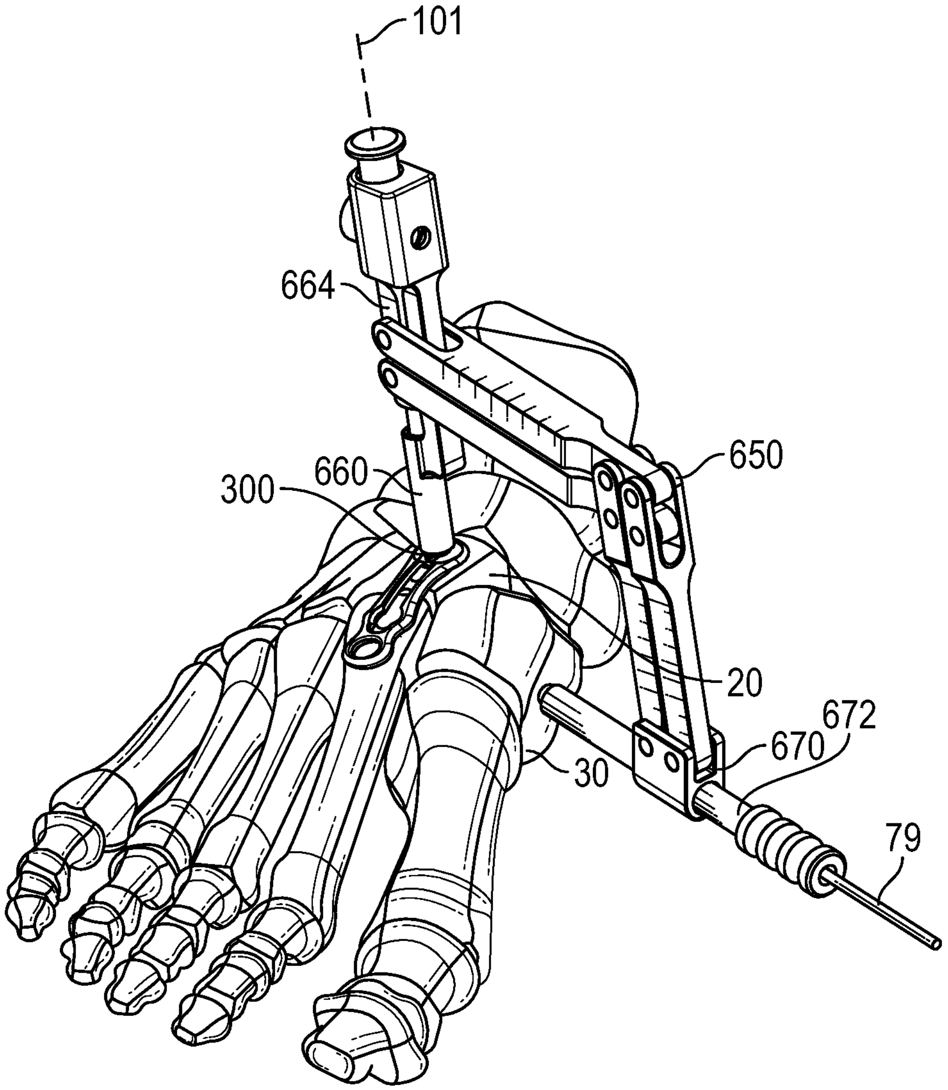
FIGS. 21-29 are perspective views of the bones of a foot, sequentially illustrating an example screw placement procedure using the example drill guide of FIGS. 6E-6H.

FIG. 21 depicts the bones 10 of an example human foot at a stage of an internal fixation procedure, such as the internal fixation procedure of FIGS. 7-15, in which the drill guide 650 has been placed and a first wire 79 (e.g., a wire, such as a K-wire, a pin, or other guide structure) has been inserted through the cannula 672 of the drill guide 650, such that the first wire 79 extends through the medial cuneiform bone 30 and into the intermediate cuneiform bone 20.

Prior to insertion of the first wire 79, the drill guide 650 can be placed by seating the tip 662 (FIG. 6E) of the anchoring arm 664 of the anchoring assembly 660 within the post insert component 300 along the central axis 101 of the implant. The anchoring arm 664 may be positioned at any desired vertical position relative to the anchoring assembly 660, so as to establish a height of the screw entry location corresponding to the first wire 79. A pilot hole may be pre-drilled for the first wire 79 prior to insertion of the first wire 79 through the cannula 672, the trajectory of the cannula 672 toward the post insert component 300 being determined by the cannula guide 670. In some embodiments, any number of other bone preparations may be used in addition to or instead of a pilot hole in order to facilitate a desired wire trajectory such as, for example, notching, burring, drilling, scraping, etc. to create a more normal and/or perpendicular surface at the entry point of the wire.

Figure 22:
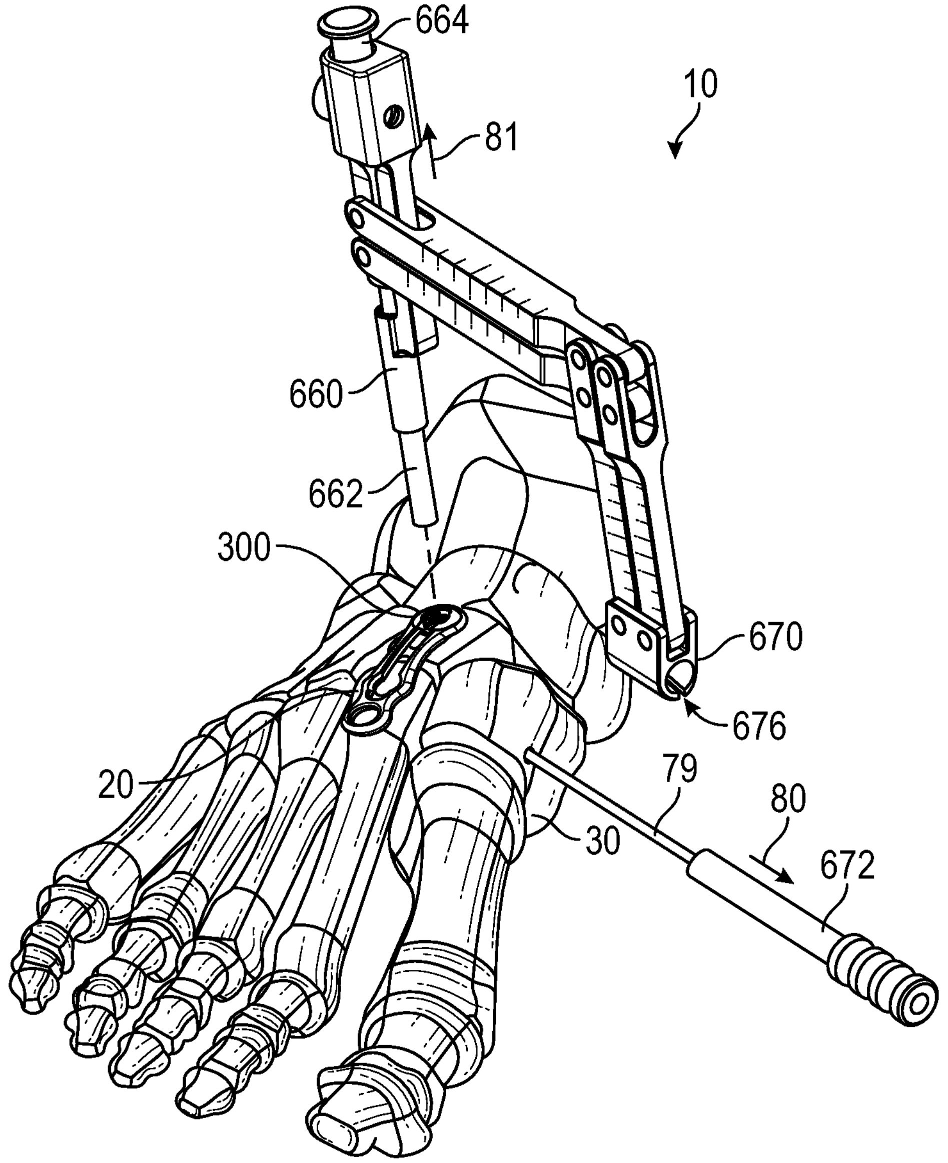

Continuing to FIG. 22, the drill guide 650 has been removed from the first wire 79. To remove the drill guide 650 from the first wire 79, the cannula 672 is removed from the cannula guide 670 by sliding the cannula 672 along the first wire 79, in the direction indicated by arrow 80. The cannula guide 670 may then be moved upward to remove the cannula guide 670 from the first wire 79, as the slot 676 is sized to accommodate the first wire 79 therethrough. Thus, the drill guide 650 can be removed after placement of the first wire 79 without requiring the removal of the drill guide 650 from the intermediate cuneiform bone 20 and translation of the cannula guide 670 along the full length of the first wire 79. In some embodiments, the drill guide 650 may be removed from the drill guide 650 by moving the anchoring arm 664 of the anchoring assembly 660 upward along the direction indicated by arrow 81, until the tip 662 of the anchoring arm 664 is removed from the post inset component 300.

Figure 23:
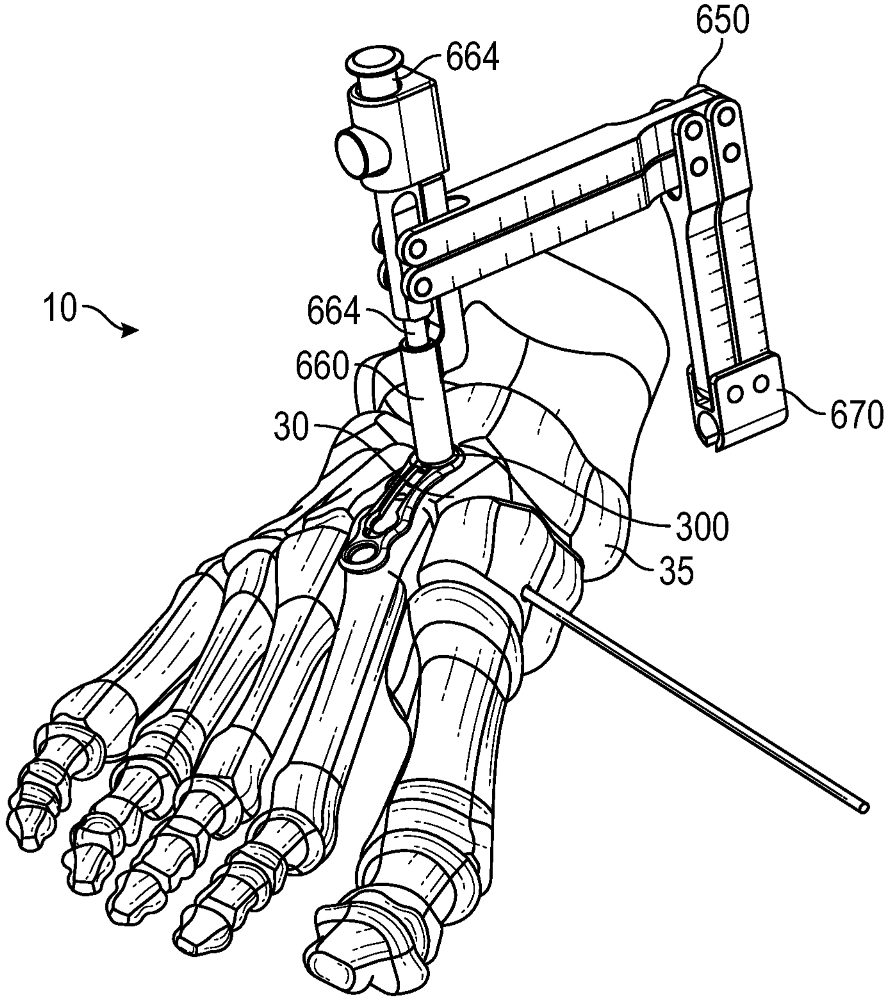

Continuing to FIG. 23, the drill guide 650 has been repositioned to a different angular orientation corresponding to a second drilling trajectory to be used for a second screw targeting the post insert component 300. For example, in the screw placement procedure of FIGS. 21-29, as the first wire 79 corresponds to a screw that will fix the medial cuneiform bone 30 to the intermediate cuneiform bone 20, the second drilling trajectory may be selected to correspond to a screw that will fix the cuboid bone 35 to the intermediate cuneiform bone 30. If the anchoring arm 664 of the anchoring assembly 660 was removed from the bone as shown in FIG. 22, it may also be reinserted into the post insert component 300 as shown in FIG. 23.

Figure 24:
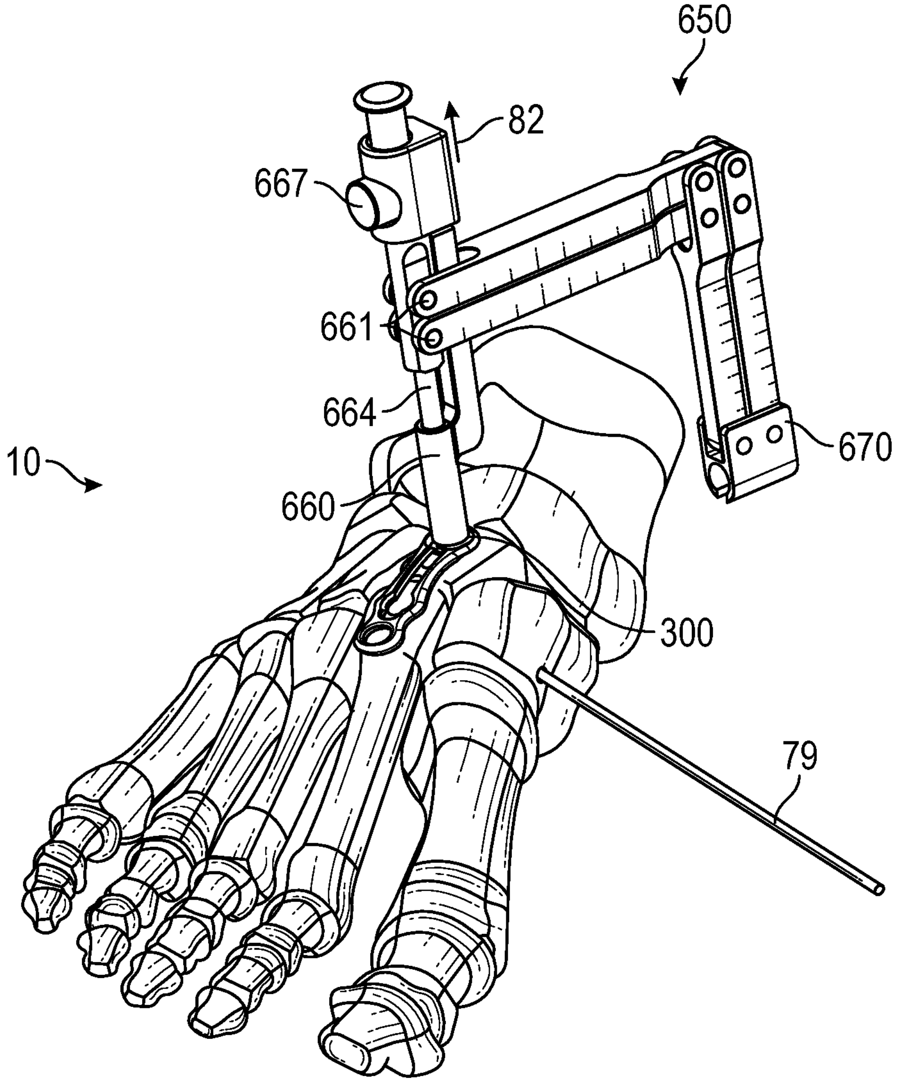

Continuing to FIG. 24, the height of the anchoring arm 664 within the anchoring assembly 660 is changed so that the second drilling trajectory will intersect the post insert component 300 at a different height relative to that of the first wire 79. The height may be adjusted by depressing button 667 and moving the anchoring arm 664 to a higher or lower position within the anchoring assembly 660. For example, in FIG. 24, the anchoring arm 664 has been moved upward along the direction indicated by arrow 82. In other implementations, the height of the anchoring arm 664 may alternatively be adjusted downward in a direction opposite arrow 82. Thus, following the adjustments shown in FIG. 24, the drill guide 650 is now positioned and configured such that the cannula guide 670 defines a second drilling trajectory so that a second wire can be inserted into the post insert component 300 at both a different angular orientation and a different height along the body of the post insert component 300, relative to the first wire 79.

Figure 25:
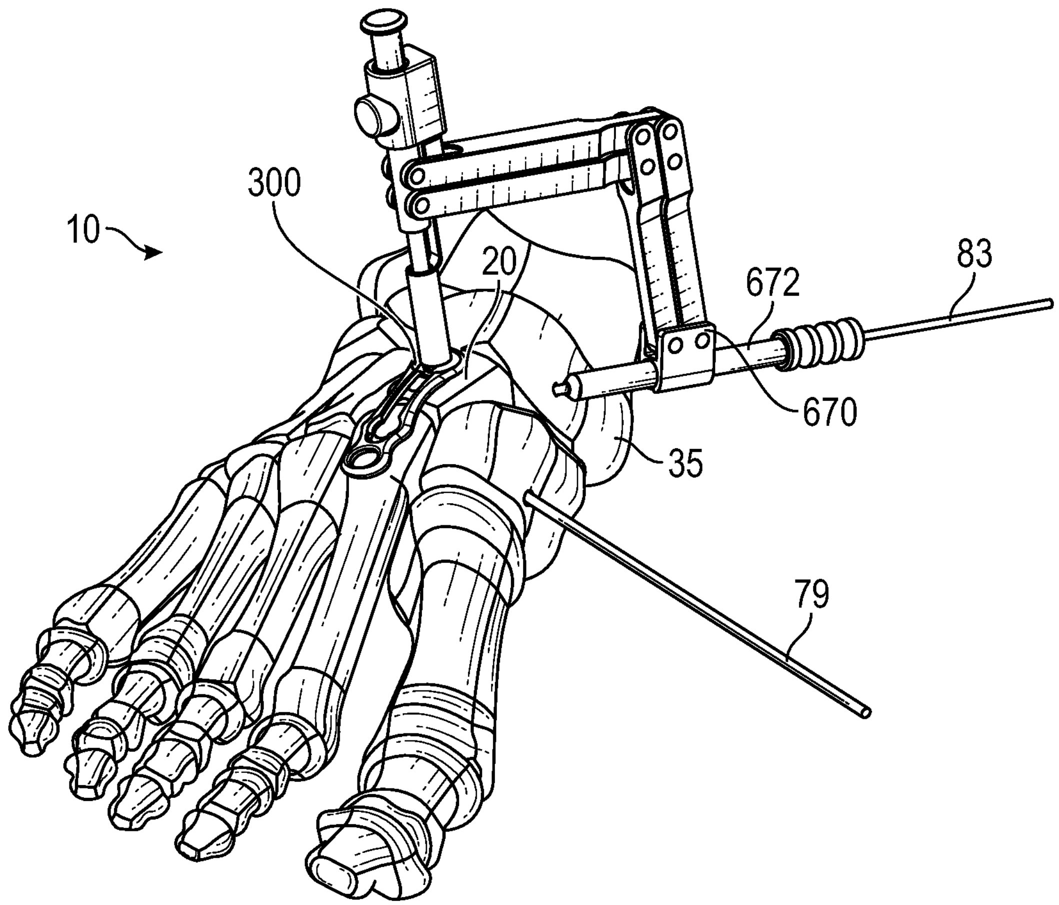

Continuing to FIG. 25, the cannula 672 (or a different cannula 672) is inserted into the cannula guide 670 and the second wire 83 is inserted through the cannula 672 along the second drilling trajectory such that the second wire 83 extends through the cuboid bone 35 and at least a portion of the intermediate cuneiform bone 20. In some embodiments, a pilot hole may be pre-drilled through the cannula 672 prior to insertion of the second wire 83. Due to the vertical offset of the first and second drilling trajectories, the first wire 79 and the second wire 83 can extend into the body of the post insert component 300 but do not intersect and the second wire 83 can be inserted without interference from the previously placed first wire 79.

Figure 26:
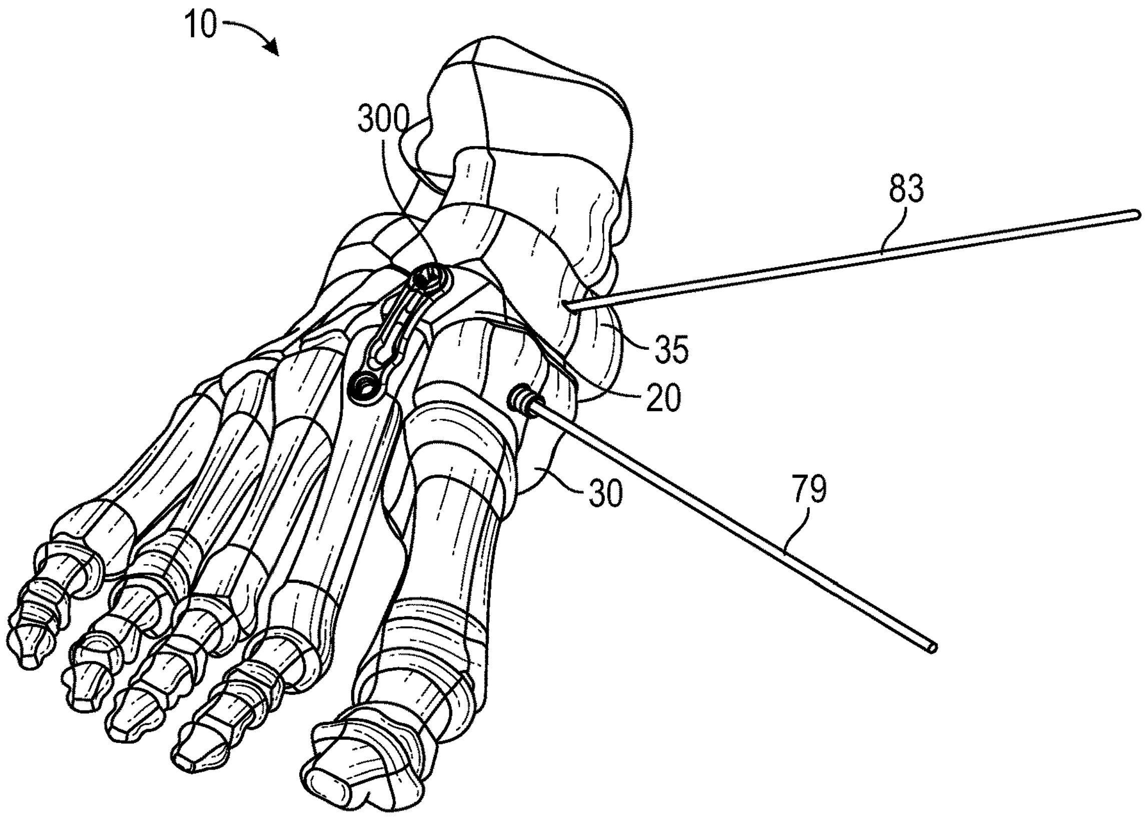
Figure 27:
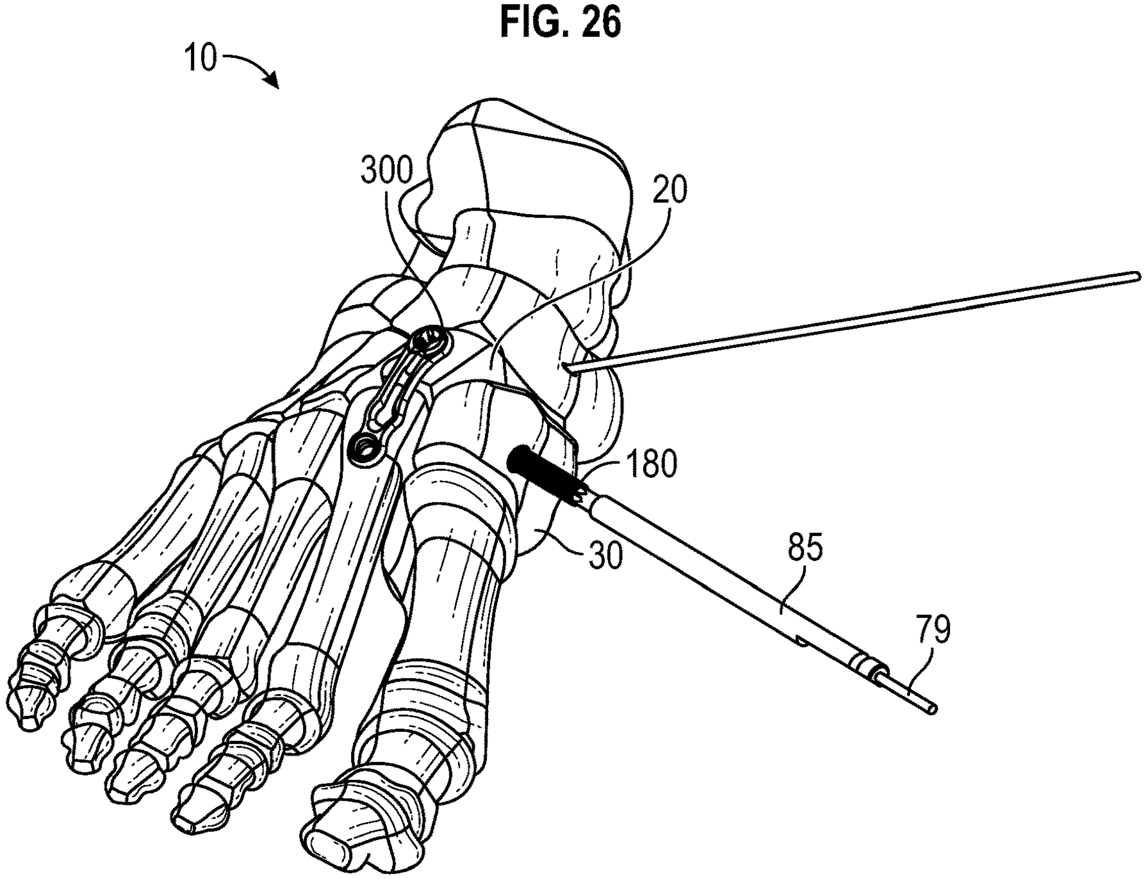
Figure 28:
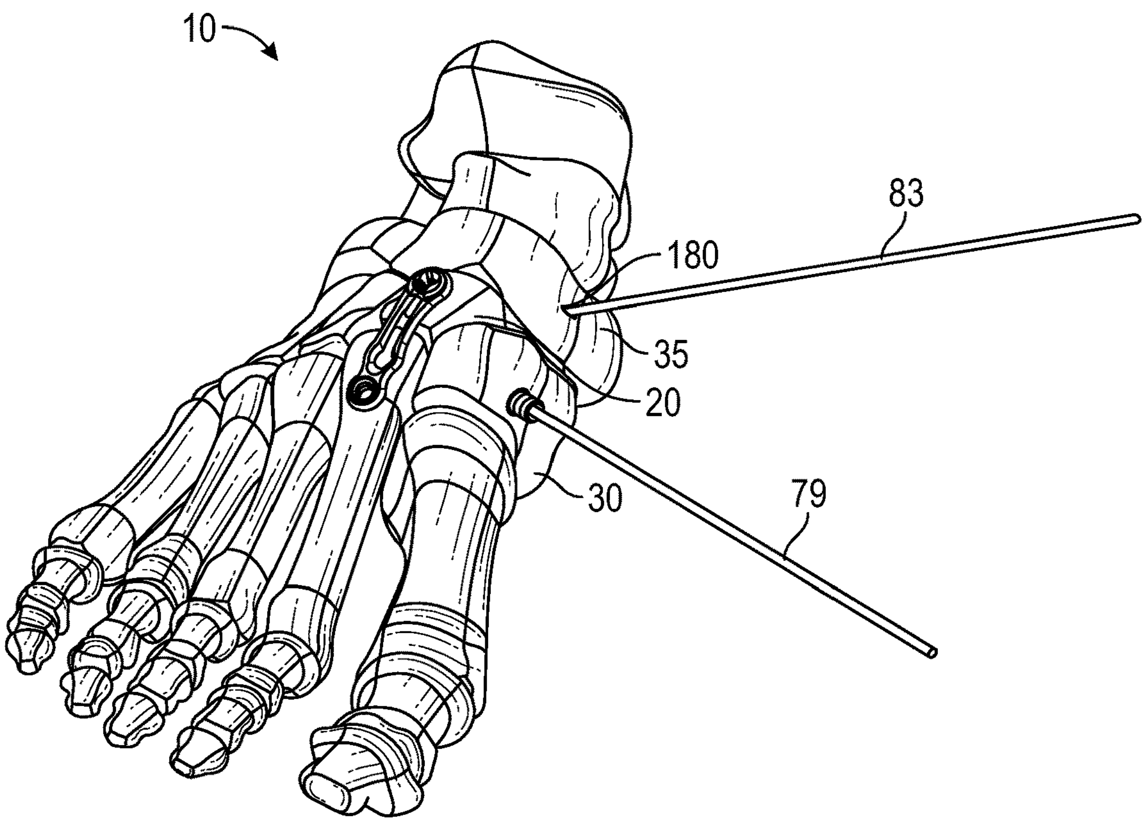
Figure 29:
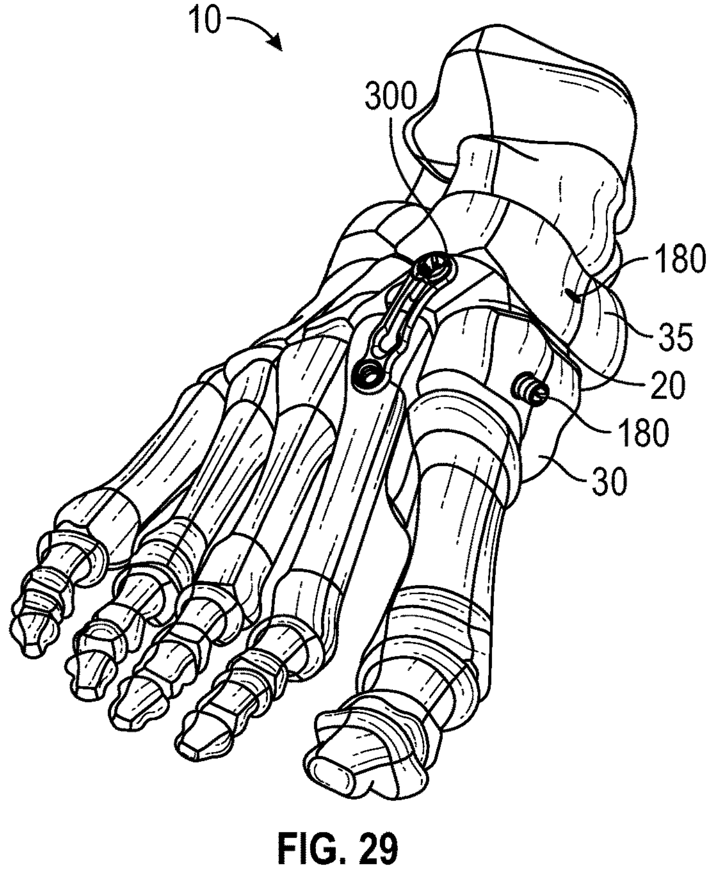

With reference to FIG. 26, the drill guide 650 can be removed from the bones 10 of the foot. Continuing to FIG. 27, a first cannulated screw 180 can be placed over the first wire 79 and driven, using a driver 85, such that the tip of the first cannulated screw 180 seats within the post insert component 300, fixing the medial cuneiform bone 30 to the intermediate cuneiform bone 20. As shown in FIG. 28, a second cannulated screw 180 can similarly be placed and driven along the second wire 83 and driven until the tip of the second cannulated screw 180 seats within the post insert component 300, fixing the cuboid bone 35 to the intermediate cuneiform bone 20. Continuing to FIG. 29, the first wire 79 and the second wire 83 may then be withdrawn from the foot. The internal fixation procedure may then proceed as desired, for example, as discussed with reference to FIGS. 7-15, such as with placement of a staple component 400 and/or a bone screw component 500 (FIG. 15).

With reference to FIGS. 30-35B, an example post removal portion of an implant removal procedure using the example extraction tool of FIGS. 17A-17F will be described. The example post removal procedure of FIGS. 30-35B may be implemented in conjunction with any of the implants described herein including a post such as the post insert component 300 disclosed herein. It may be desired to remove the various implants and/or components described herein for a variety of reasons as will be understood by those having ordinary skill in the relevant art. For example, in some implementations the implants of the present technology may be placed with the intention of being temporary rather than permanent implants, or an implant may need to be removed after placement for adjustment for adjustment or further correction, due to failure, or for any other reason.

The portions of the post removal procedure including the extraction tool 800 of FIGS. 17A-17F, illustrated in FIGS. 32A-35B, are shown in additional enlarged views for clarity. FIGS. 32A, 33A, 34A, and 35A illustrate the procedure in the context of the bones 10 of a foot. FIGS. 32B, 33B, 34B, and 35B illustrate corresponding stages of the procedure in an enlarged side view, with the bones 10 of the foot hidden for clarity of illustration.

Figure 30:
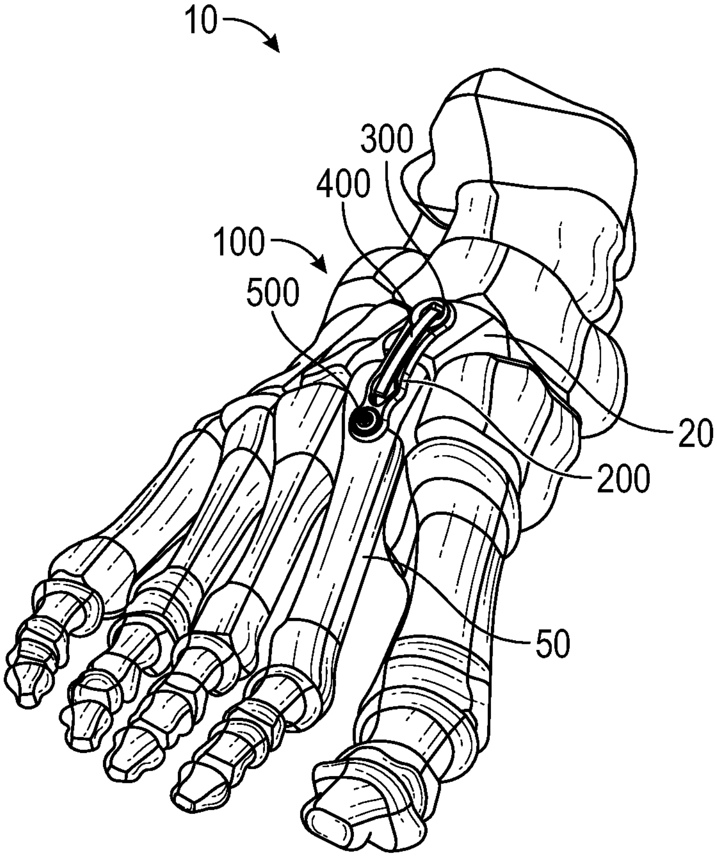
FIGS. 30-35B are perspective views of the bones of a foot, sequentially illustrating a portion of an example implant removal procedure using the example extraction tool of FIGS. 17A-17F.

FIG. 30 is a perspective view of the bones 10 of a foot having an implant 100 placed therein. The implant 100 may be, for example, the implant 100 of FIGS. 1A-1E, the post insert and collar 350 of FIGS. 3D-3F, or the implants placed in the procedures described with reference to FIGS. 7-15 or FIGS. 21-29. In the example of FIG. 30, the implant 100 includes a bone plate component 200 seated within the intermediate cuneiform bone 20 and extending across the second metatarsal 50, a post insert component 300 seated within the bone plate component 200 and the intermediate cuneiform bone 20, a staple component 400 seated within the intermediate cuneiform bone 20 and the second metatarsal 50 through the bone plate component 200, and a bone screw component 500 seated within the second metatarsal 50 through the bone plate component 200. In the initial configuration of FIG. 30, the implant 100 has been prepared for removal by removing any lateral screws that may previously have been inserted into the post insert component 300, as described elsewhere herein.

Figure 31:
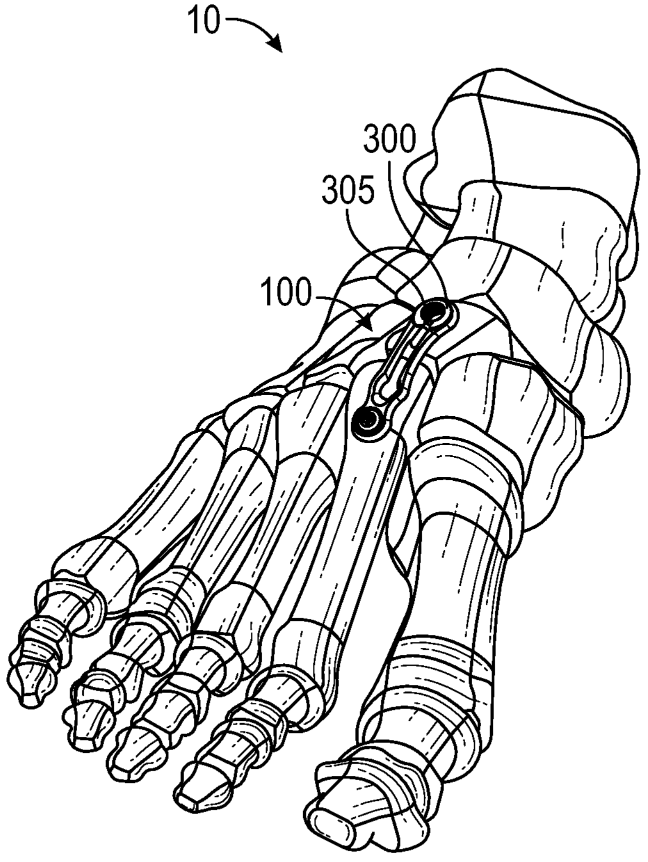

Referring now to FIG. 31, the staple component 400 is removed from the implant 100. Removal of the staple component 400 exposes the aperture 305 of the post insert component 300 such that the aperture 305 may be utilized for removal of the post insert component.

Figure 32A:
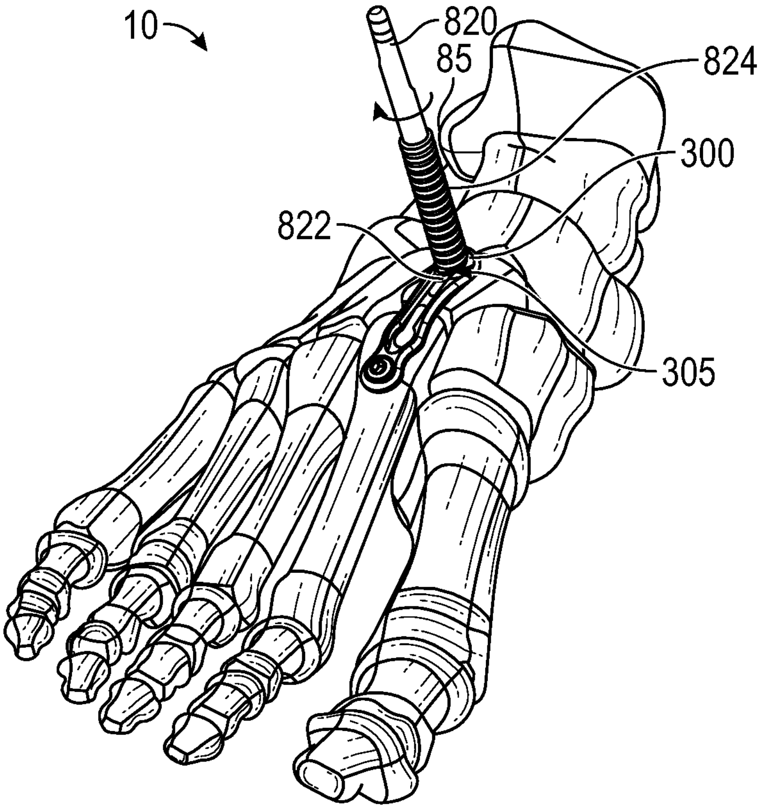
Figure 32B:
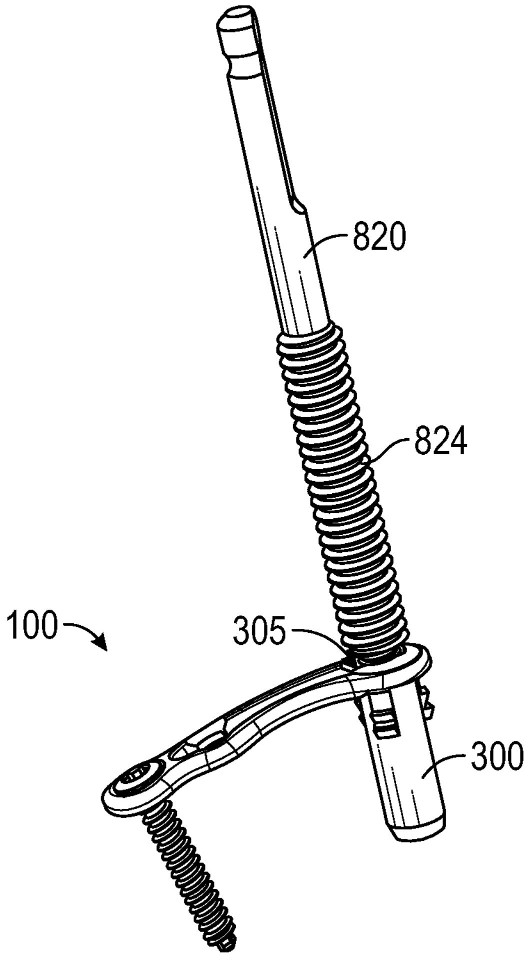

Continuing to FIGS. 32A and 32B, the shaft 820 of an extraction tool 800 (FIGS. 17A-17F) is coupled to the post insert component 300. The shaft 820 can be coupled to the post insert component 820 by engaging the screw threads 823 and of the distal portion 822 of the shaft 820 (FIG. 17D) with the internal screw threads 322 of the post insert component 300 (FIGS. 3A-3C) and rotating the shaft 820 as indicated by arrow 85, until the distal portion 822 of the shaft 820 is firmly seated within the post insert component 300.

Figure 33A:
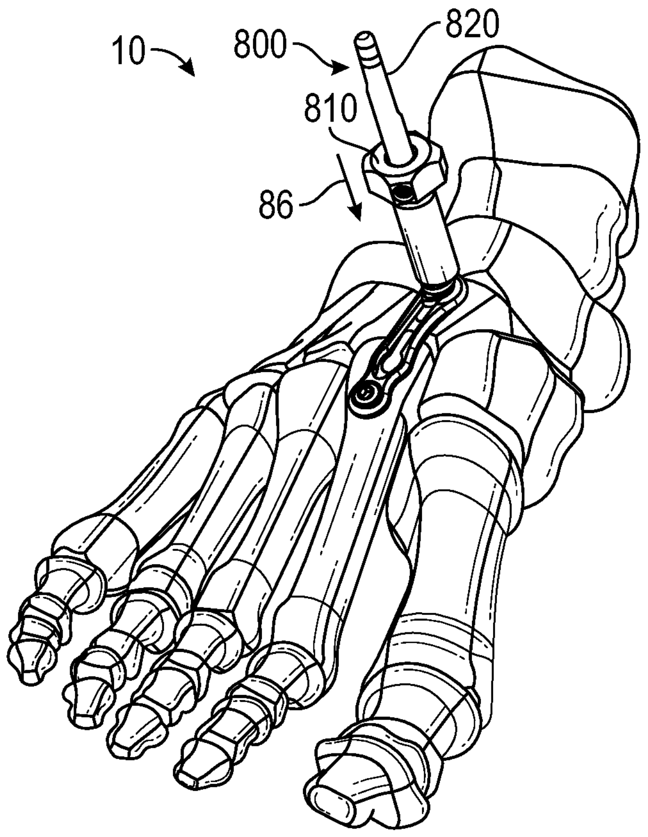
Figure 33B:
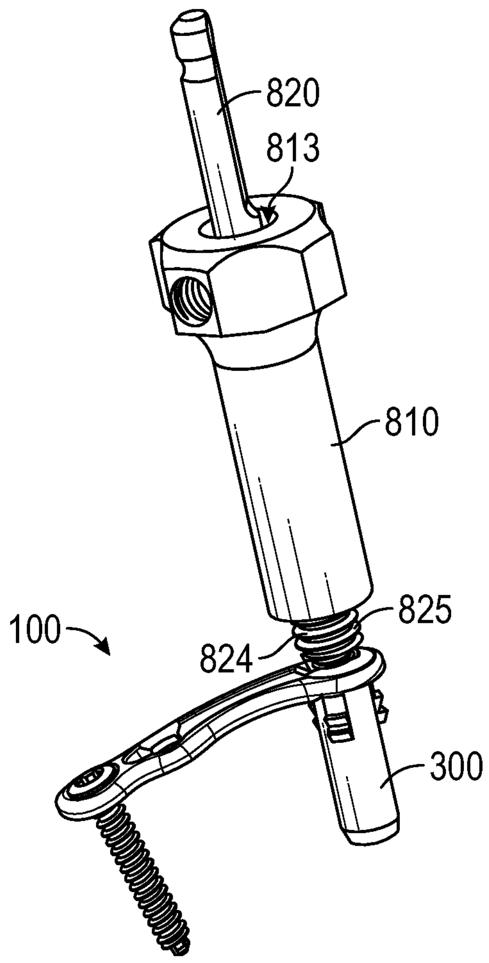

Continuing to FIGS. 33A and 33B, the sleeve 810 of the extraction tool 800 may be placed over the shaft 820 along a downward direction indicated by arrow 86. The sleeve 810 may be placed such that the shaft 820 extends through the threaded aperture 813 of the sleeve 810 and the internal screw threads 815 (FIG. 17F) begin to engage with the corresponding external screw threads 825 on the medial portion 824 of the shaft 820.

Figure 34A:
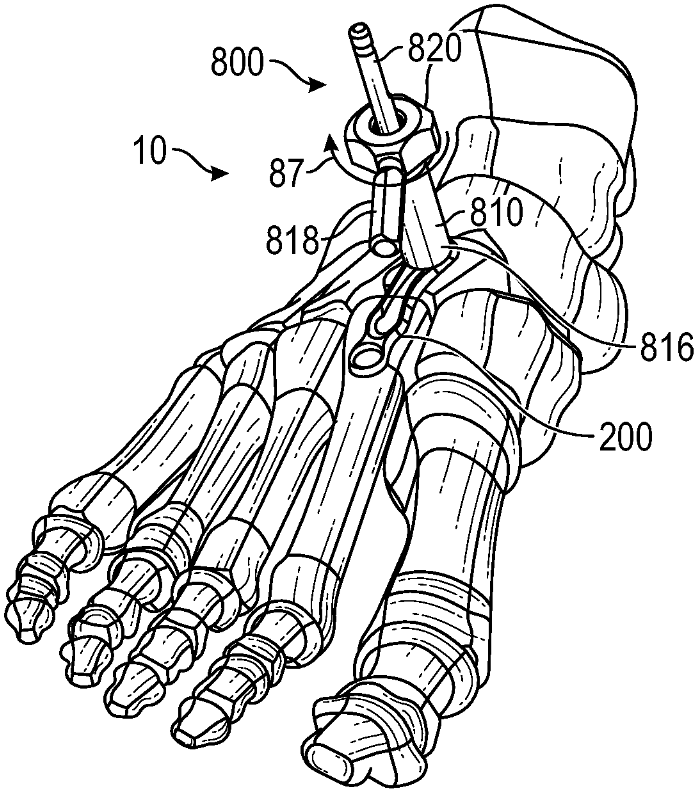
Figure 34B:
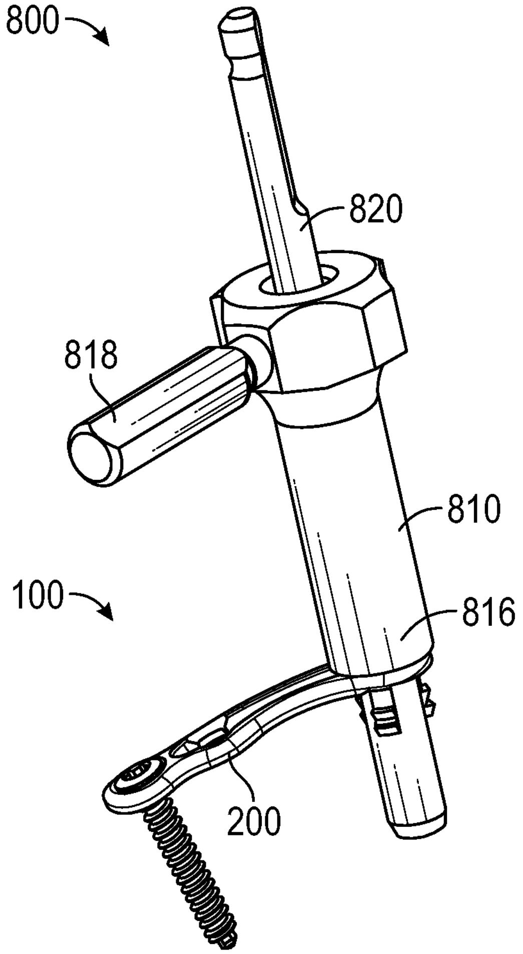

Continuing to FIGS. 34A and 34B, the sleeve 810 can be rotated as indicated by arrow 87 such that the internal screw threads 815 of the sleeve 810 engage with the external screw threads 825 of the medial portion 824 of the shaft 820. The sleeve 810 may be rotated until the body 816 of the sleeve 810 abuts the bone plate component 200. An optional handle 818 may be attached to a threaded aperture 814 in the head 812 of the sleeve 810 (FIG. 17E) to facilitate manipulation of the extraction tool 800.

Figure 35A:
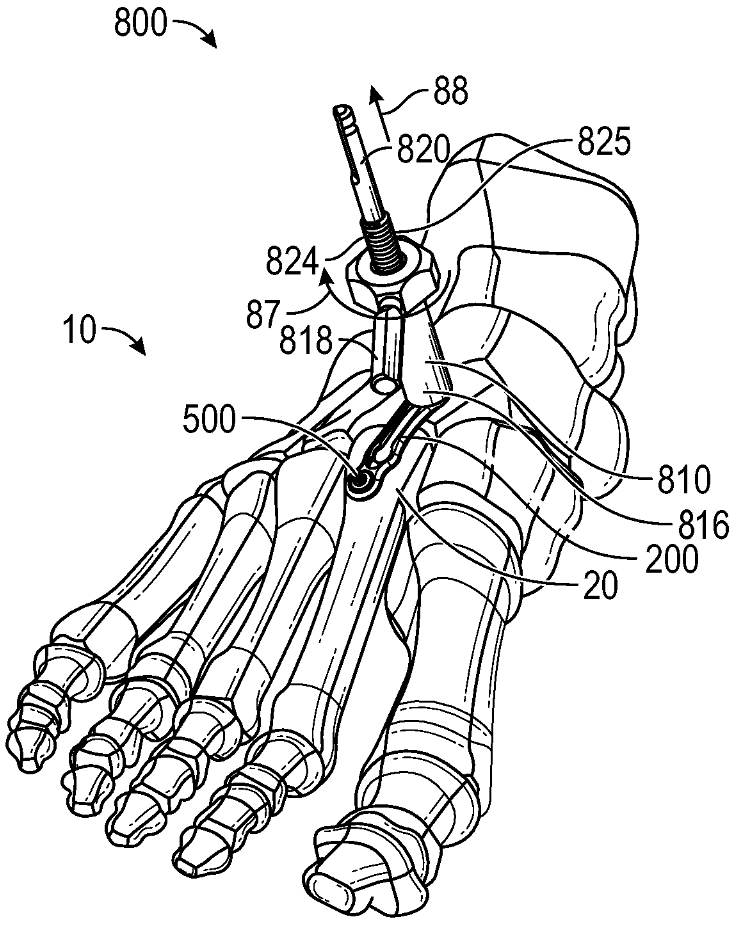
Figure 35B:
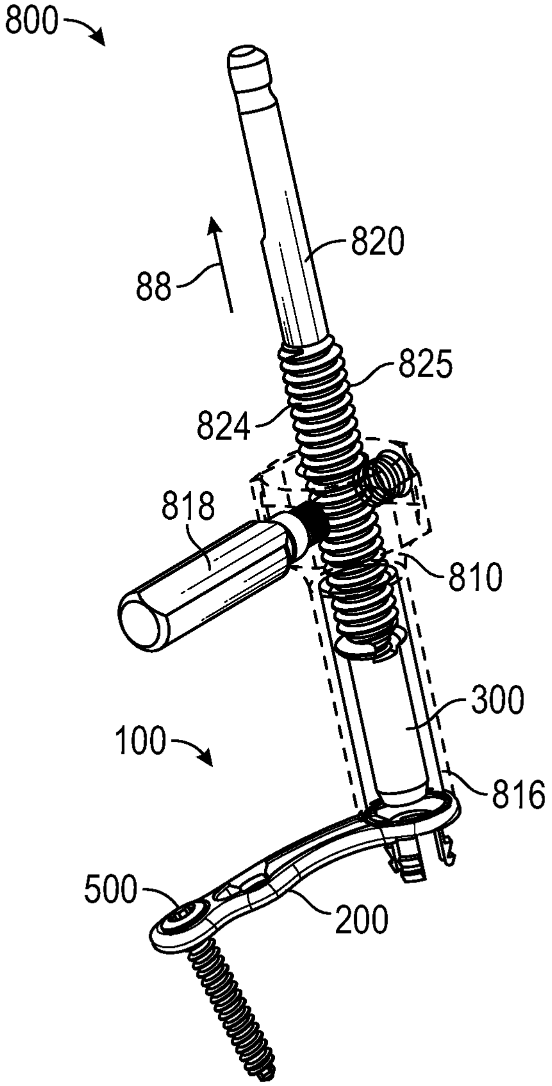

Continuing to FIGS. 35A and 35B, the extraction tool 800 removes the post insert component 300 from the implant 100. Once the body 816 of the sleeve 810 has contacted the bone plate component 200, the bone plate component prevents further downward motion of the sleeve 810 relative to the implant 100. Thus, continued rotation along the direction indicated by arrow 87 causes the shaft 820, as well as the post insert component 300 attached thereto, to be drawn upward along the direction indicated by arrow 88, due to the engagement of the screw threads of the sleeve 810 and the intermediate portion 824 of the shaft 820. The sleeve 810 may continue to be rotated until the post insert component 300 is partially or completely withdrawn from the bone plate component 200. The post insert component 300 and extraction tool 800 may then be removed from the bone plate component 200. Alternatively, in some embodiments, the post insert component 300 may be removed by gripping the extraction tool 800 and pulling upward rather than by continuing to rotate the sleeve 810. In some embodiments, the bone screw component 500 and the bone plate component 200 may further be removed from the bones 10 if complete removal of the implant 100 is desired.

The embodiments described herein are exemplary. Modifications, rearrangements, substitute processes, etc. may be made to these embodiments and still be encompassed within the teachings set forth herein. Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently rather than sequentially.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A in conjunction with a second processor configured to carry out recitations B and C.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A modular bone fixation system comprising:

a bone plate comprising:

a first end having a post aperture extending therethrough;

a plurality of tabs adjacent to and circumferentially spaced about the post aperture, each of the plurality of tabs extending from a bottom surface of the bone plate and having one or more bone engaging features thereon, wherein the plurality of tabs are configured to extend into a first hole within a first bone;

a second end having a screw aperture extending therethrough; and a staple aperture extending through the bone plate at an intermediate location between the first end and the second end;

a post insert comprising a body sized and shaped to fit within the post aperture and a head configured to seat against the bone plate around at least a portion of the post aperture, wherein when positioned within the post aperture, the body of the post insert forces the plurality of tabs outward such that the one or more bone engaging features are configured to grip the first bone;

a staple comprising a bridge, a bone engaging member extending from a first end of the bridge, and a post engaging member extending from a second end of the bridge opposite the first end, the bone engaging member configured to extend through the staple aperture and seat within a second hole within a second bone to exert a compressive force between the first bone and the second bone; and a bone screw configured to extend through the screw aperture and seat within the second bone.

2. The modular bone fixation system of claim 1, further comprising at least one lateral screw configured to seat at least partially within a third bone and the first bone, at least a portion of the at least one lateral screw being configured to seat within the post insert to fix the third bone relative to the post insert.

3. The modular bone fixation system of claim 1, wherein the body of the post insert comprises a polymeric material penetrable by a screw.

4. The modular bone fixation system of claim 1, wherein the post insert further comprises an axial aperture extending through the head and at least a portion of the body, and the post engaging member is configured to seat within the axial aperture of the post insert.

5. The modular bone fixation system of claim 1, wherein the head of the post insert comprises a cutaway sized and shaped to receive at least a portion of the bridge of the staple component therein.

6. The modular bone fixation system of claim 1, wherein the first and second bones each comprise one of a cuneiform bone, a metatarsal, a cuboid bone, or a navicular bone.

* * * * *